United States Patent
Liu et al.

(10) Patent No.: US 10,543,284 B2
(45) Date of Patent: Jan. 28, 2020

(54) ANTI-C-MET ANTIBODY AND ANTI-C-MET ANTIBODY-CYTOTOXIC DRUG CONJUGATE AND PHARMACEUTICAL USE THEREOF

(71) Applicants: Suzhou Suncadia Biopharmaceuticals Co., Ltd., Suzhou, Jiangsu (CN); Jiangsu Hengrui Medicine Co., Ltd., Lianyungang, Jiangsu (CN); Shanghai Hengrui Pharmaceutical Co., Ltd., Shanghai (CN)

(72) Inventors: Jiajian Liu, Shanghai (CN); Lianshan Zhang, Shanghai (CN); Weikang Tao, Shanghai (CN); Yayuan Fu, Shanghai (CN); Ling Zhang, Shanghai (CN); Dong Ma, Shanghai (CN); Dongbing Cui, Shanghai (CN); Yali Wang, Shanghai (CN); Jianyan Xu, Shanghai (CN); Jindong Liang, Shanghai (CN); Ying Zhang, Shanghai (CN); Guiyang Jiang, Shanghai (CN); Junzhuan Qiu, Shanghai (CN); Ziyong Sun, Shanghai (CN); Jiping Zha, Shanghai (CN); Jingping Wei, Shanghai (CN)

(73) Assignees: Suzhou Suncadia Biopharmaceuticals Co., Ltd., Suzhou, JIangsu (CN); Jiangsu Hengrui Medicine Co., Ltd., Lianyungang, Jiangsu (CN); Shanghai Hengrui Pharmaceutical Co., Ltd., Shanghai (CN)

( * ) Notice: Subject to any disclaimer, the term of this patent is extended or adjusted under 35 U.S.C. 154(b) by 112 days.

(21) Appl. No.: 15/565,928

(22) PCT Filed: Apr. 7, 2016

(86) PCT No.: PCT/CN2016/078699
§ 371 (c)(1),
(2) Date: Oct. 12, 2017

(87) PCT Pub. No.: WO2016/165580
PCT Pub. Date: Oct. 20, 2016

(65) Prior Publication Data
US 2018/0110875 A1 Apr. 26, 2018

(30) Foreign Application Priority Data

Apr. 17, 2015 (CN) .......................... 2015 1 0185602
Jun. 4, 2015 (CN) .......................... 2015 1 0300885

(51) Int. Cl.
| | | |
|---|---|---|
| A61K 39/395 | (2006.01) | |
| A61K 47/68 | (2017.01) | |
| A61K 31/4745 | (2006.01) | |
| A61K 31/537 | (2006.01) | |
| A61P 35/00 | (2006.01) | |
| A61K 38/08 | (2019.01) | |
| C07K 16/28 | (2006.01) | |
| C07K 16/30 | (2006.01) | |

(Continued)

(52) U.S. Cl.
CPC ...... *A61K 47/6849* (2017.08); *A61K 31/4745* (2013.01); *A61K 31/537* (2013.01); *A61K 38/08* (2013.01); *A61K 47/6817* (2017.08); *A61K 47/6851* (2017.08); *A61K 47/6857* (2017.08); *A61K 47/6859* (2017.08); *A61K 47/6861* (2017.08); *A61K 47/6863* (2017.08); *A61K 47/6889* (2017.08); *A61P 35/00* (2018.01); *C07K 16/2863* (2013.01); *C07K 16/30* (2013.01); *C07K 16/303* (2013.01); *C07K 16/3023* (2013.01); *C07K 16/3038* (2013.01); *C07K 16/3046* (2013.01); *C07K 16/464* (2013.01); *A61K 2039/505* (2013.01); *C07K 2317/24* (2013.01); *C07K 2317/56* (2013.01); *C07K 2317/565* (2013.01); *C07K 2317/567* (2013.01); *C07K 2317/73* (2013.01); *C07K 2317/77* (2013.01); *C07K 2317/94* (2013.01)

(58) Field of Classification Search
CPC .................................................. A61K 47/6849
See application file for complete search history.

(56) References Cited

U.S. PATENT DOCUMENTS

| 7,750,116 B1 | 7/2010 | Doronina et al. |
|---|---|---|
| 2005/0238649 A1 | 10/2005 | Doronina et al. |

FOREIGN PATENT DOCUMENTS

| CN | 101035808 A | 9/2007 |
|---|---|---|
| CN | 103394083 A | 11/2013 |

(Continued)

OTHER PUBLICATIONS

Brown et al J. Immunol. May 1996; 156(9):3285-3291 (Year: 1996).*

(Continued)

*Primary Examiner* — Sheela J. Huff
(74) *Attorney, Agent, or Firm* — Panitch Schwarze Belisario & Nadel LLP

(57) ABSTRACT

Provided are an anti-c-Met antibody or an antigen binding fragment thereof, and an anti-c-Met antibody-cytotoxic drug conjugate, wherein the antibody or antigen binding fragment thereof is a chimeric antibody or a humanized antibody. Also provided are pharmaceutical compositions containing the humanized anti-c-Met antibody or antigen binding fragment thereof, the antibody-cytotoxic drug conjugate, or pharmaceutically acceptable salts or solvents thereof, that are used in the treatment of cancer.

36 Claims, 1 Drawing Sheet
Specification includes a Sequence Listing.

(51) Int. Cl.
    *C07K 16/46* (2006.01)
    *A61K 39/00* (2006.01)

(56) References Cited

FOREIGN PATENT DOCUMENTS

WO    2004010957 A2    2/2004
WO    2005081711 A2    9/2005

OTHER PUBLICATIONS

Vajdos et al (J. Mol. Biol. Jul. 5, 2002;320(2); 415-428 (Year: 2002).*
Int'l Search Report dated Jul. 12, 2016 in Int'l Application No. PCT/CN2016/078699.
Written Opinion dated Jul. 12, 2016 in Int'l Application No. PCT/CN2016/078699.
SciFinder, CAS Registry No. 139504-50-0, American Chemical Society (ACS) (2017).
SciFinder, CAS Registry No. 796073-69-3, American Chemical Society (ACS) (2017).
SciFinder, CAS Registry No. 796073-54-6, American Chemical Society (ACS) (2017).
Yasukawa et al, "Enzymatic Synthesis of Chiral Phenylalanine Derivatives by a Dynamic Kinetic Resolution of Corresponding Amide and Nitrile Substrates With a Multi-Enzyme System," Advanced Synthesis & Catalysis, vol. 354, No. 17, pp. 3327-3332 (2012).
Pettit et al, "Antineoplastic Agents 365. Dolastatin 10 SAR Probes," Anti-Cancer Drug Design, vol. 13, pp. 243-277 (1998).
Pettit et al, "Specific Activities of Dolastatin 10 and Peptide Derivatives Against Cryptococcus Neoformans," Antimicrobial Agents and Chemotherapy, vol. 42, No. 11, pp. 2961-2965 (1998).
Woyke et al, "In Vitro Activities and Postantifungal Effects of the Potent Dolastatin 10 Derivative Auristatin PHE," Antimicrobial Agents and Chemotherapy, vol. 45, No. 12, pp. 3580-3584 (2001).
Doronina et al, "Enhanced Activity of Monomethylauristatin F Through Monoclonal Antibody Delivery: Effects of Linker Technology on Efficacy and Toxicity," Bioconjugate Chem., vol. 17, No. 1, pp. 114-124 (2006).
Chari et al, "Immunoconjugates Containing Novel Maytansinoids: Promising Anticancer Drugs," Cancer Research, vol. 52, pp. 127-131 (1992).
Pettit et al, "Dolastatins 24. Synthesis of (−) Dolastatin 10. X-Ray Molecular Structure of N,N-Dimethylvalyl-Valyl-Dolaisoleuine Tert-Butyl Ester," J. Chem. Soc. Perkin Trans,, vol. 1, pp. 859-863 (1996).
Doronina et al, "Development of Potent Monoclonal Antibody Auristatin Conjugates for Cancer Therapy," Nature Biotechnology, vol. 21, No. 7, pp. 778-754 (2003).
Geoghegan et al, "Site-Directed Conjugation of Nonpeptide Groups to Peptides and Proteins Via Periodate of a 2-Amino Alcohol. Application to Modification At N-Terminal Serine," Bioconjugate Chem., vol. 3, pp. 138-146 (1992).
Keil et al, "IUPAC-IUB Commission on Biochemical Nomenclature a One-Letter Notation for Amino Acid Sequences Tentative Rules," The Journal of Biological Chemistry, vol. 243, No. 13, pp. 3557-3559 (1968).
Jones et al, "Replacing the Complementarity-Determining Regions in a Human Antibody With Those From a Mouse," Nature, vol. 321, pp. 522-525 (1986).
Widdison et al, "Semisynthetic Maytansine Analogues for the Targeted Treatment of Cancer," Journal of Medicinal Chemistry, vol. 49, No. 14, pp. 4392-4408 (2006).
Pettit et al, "The Absolute Configuration and Synthesis of Natural (−)-Dolastatin 101," J. Am. Chem. Soc., vol. 111, No. 14, pp. 5463-5465 (1989).
Pettit et al, "The Dolastatins; 18: Stereospecific Synthesis of Dolaproine," Synthesis, pp. 719-725 (1996).
Yu et al, "The Biosynthetic Gene Cluster of the Maytansinoid Antitumor Agent Ansamitocin From Actinosynnema Pretiosum," PNAS, vol. 99, No. 12, pp. 7968-7973 (2002).
Co et al, "Humanized Antibodies for Antiviral Therapy," PNAS, vol. 88, pp. 2869-2873 (1991).
Riechmann et al, "Reshaping Human Antibodies for Therapy," Nature, vol. 332, pp. 323-327 (1988).
Vitetta et al, "Redesigning Nature's Poisons to Create Anti-Tumor Reagents," Science, vol. 238, pp. 1098-1104 (1987).
Verhoeyen et al, "Reshaping Human Antibodies: Grafting an Antilysozyme Activity," Science, vol. 239, No. 4847, pp. 1534-1536 (1988).

* cited by examiner

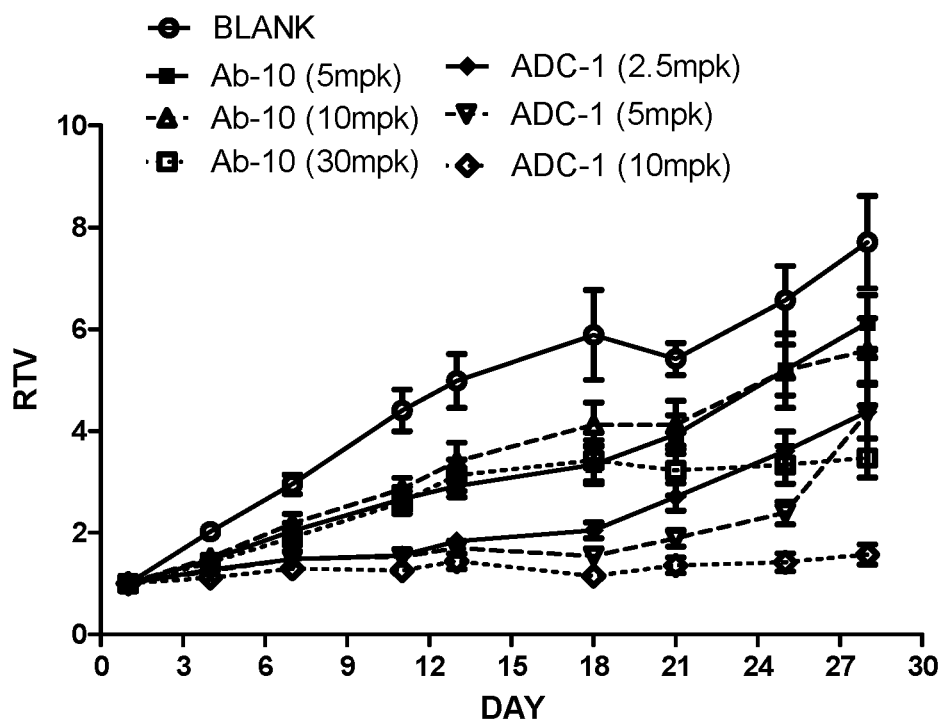

ANTI-C-MET ANTIBODY AND ANTI-C-MET ANTIBODY-CYTOTOXIC DRUG CONJUGATE AND PHARMACEUTICAL USE THEREOF

CROSS-REFERENCE TO RELATED APPLICATIONS

This application is a Section 371 of International Application No. PCT/CN2016/078699, filed Apr. 7, 2016, which was published in the Chinese language on Oct. 20, 2016, under International Publication No. WO 2016/165580 A1 and the disclosure of which is incorporated herein by reference.

REFERENCE TO SEQUENCE LISTING SUBMITTED ELECTRONICALLY

This application contains a sequence listing, which is submitted electronically via EFS-Web as an ASCII formatted sequence listing with a file name "688452.55 Sequence Listing" and a creation date of Oct. 11, 2017, and having a size of 47.8 KB. The sequence listing submitted via EFS-Web is part of the specification and is herein incorporated by reference in its entirety.

FIELD OF THE INVENTION

The present invention relates to a c-Met antibody or an antigen binding fragment thereof, chimeric or humanized antibodies comprising CDR regions of the c-Met antibody, conjugates of the c-Met antibody to cytotoxic drugs or pharmaceutically acceptable salts or solvates thereof; pharmaceutical compositions comprising the same; and their use as anti-cancer agents. In particular, the present invention relates to a humanized c-Met antibody and a c-Met antibody-cytotoxic drug conjugate or a pharmaceutically acceptable salt or solvate thereof, and their use in the preparation of a medicament for the treatment of c-Met-mediated diseases or conditions.

BACKGROUND OF THE INVENTION

In recent years, molecular biology and tumor pharmacology studies have shown that tyrosine kinase (Protein Tyrosine Kinases, PTKs)-related cell signal transduction pathways play an extremely important role in tumor formation and development, and that more than 50% of proto-oncogenes and oncogene products have tyrosine kinase activity. The c-Met proto-oncogene belongs to the Ron subfamily of the PTKs family, and the encoded c-Met protein is a high affinity receptor for the Hepatocyte Growth Factor/Scatter Factor, HGF/SF. The HGF/c-Met signaling pathway is closely related to the process of angiogenesis and tumor growth. Its sustained activation is an important cause of carcinogenesis, cancer cell proliferation, or hyperplasia of cancer cells. Inhibition of this pathway has become a new method of targeted tumor therapy.

The c-Met proto-oncogene, which is more than 120 kb in size is located on the long arm of human chromosome 7 (7q31), and it encodes a c-Met protein precursor with a molecular weight of about 150 kD, which undergoes local glycosylation to form a 170 kD glycoprotein. The glycoprotein is further cleaved into an alpha subunit (50 kDa) and a beta subunit (140 kDa), which are linked by disulfide bonds to form a mature c-Met protein receptor. The heterodimer contains two strands, the beta chain has an extracellular domain, a transmembrane region (also called a membrane stretch fragment), and an intracellular domain (comprising an intracellular tyrosine kinase binding site). The alpha chain has only an extracellular portion, but it is highly glycosylated and is attached to the beta chain by disulfide bonds. The extracellular region of the two subunits is the recognition site of the corresponding ligand, and the intracellular domain has tyrosine kinase activity.

C-Met activation occurs through three types of mechanisms: one type is dependent on the activation mechanism of HGF, the second type is not dependent on the HGF activation mechanism, and the third type occurs through other membrane pathways, such as through the hyaluronic acid surface receptor CD44, adhesin and RON signal transduction pathways, and so on. One of the most common mechanism of c-Met activation is that dependent on the activation mechanism of HGF. The N-terminus of HGF binds to c-Met to promote the dimerization and autophosphorylation of Tyr1234 and Tyr1235 on the beta chain, and phosphorylation of Tyr1349 and Tyr1356 near the C-terminus produces a binding site for multiple linker proteins which in turn induce P13K/Akt, Ras/Mapk, c-Src and STAT3/5-mediated activation of downstream signaling, and trigger different cellular responses, such as cell survival and activity (closely related to P13K/Akt pathway) and tumor metastasis and cell proliferation (mainly mediated by Ras/Mapk). In addition, the cross-talk of c-Met with other membrane receptors has been known to promote tumor formation and metastasis. Since c-Met is the intersection of many pathways leading to tumor formation and metastasis, simultaneous interference with many pathways can be achieved relatively easily by targeting c-Met, and c-Met has become a promising target for antitumor formation and metastasis therapy.

An antibody drug conjugate (ADC) is formed by linking a monoclonal antibody or antibody fragment to a biologically active cytotoxin with a stable chemical linker, which fully utilizes the specific binding activity of the antibody to a tumor cell or a highly expressed antigen, combined with the high efficiency of the cytotoxin, to avoid toxic side effects to normal cells. This means that antibody drug conjugates can bind tumor cells specifically and reduce their effects on normal cells, compared to conventional chemotherapeutic agents.

ADCs consist of three parts: antibodies (targeting), linkers and toxins. Among them, a good target (antibody portion), which includes not only specific targeting binding, but also effective endocytosis, determines the specificity of the ADC drug.

There are three main types of inhibitors for c-Met kinase: HGF and c-Met biological antagonists, HGF and c-Met antibodies, and small molecule c-Met inhibitors. The existing clinical studies show that the antibodies directly targeting HGF or c-Met, or c-Met small molecule inhibitors is not ideal. An ADC for c-Met may be the most effective method for treating a tumor. Presently, there is no c-Met ADC drug in clinical studies.

The present invention firstly discloses an anti-c-Met ADC, which not only retains the antibody-dependent cell proliferation inhibitory effect of the anti-c-Met antibody of the present invention, but also increases the effect of the potential cytotoxic drug. Because of the targeted release of toxin into tumor cells, toxic drug side effects do not increase with the increase in efficacy. The present invention provides a humanized antibody and a chimeric antibody that specifically bind human c-Met, and the humanized antibody and chimeric antibody are characterized by high affinity, high efficacy, endocytosis, good stability and absence of c-Met agonist activity, etc. On the basis of these desirable properties, the present invention also provides an antibody-cytotoxic drug conjugate that specifically binds to human c-Met, or a pharmaceutically acceptable salt or solvate compound thereof, that retains the antibody-dependent inhibition of cell proliferation while increasing the potential effect of the conjugated cytotoxic drugs and the broad spectrum of diseases that can be treated by the conjugate. Because the toxin is releases into targeted tumor cells upon endocytosis of the anti-c-Met antibody of the present invention, the toxic drug side effects do not increase along with the increase in efficacy.

SUMMARY OF THE INVENTION

The present invention provides an antibody or antigen-binding fragment thereof that specifically binds to c-Met, comprising at least one CDR selected from the following sequences or mutant sequences thereof:

heavy chain variable region HCDR sequence: SEQ ID NO: 6, SEQ ID NO:7 or SEQ ID NO:8;
and
light chain variable region HCDR sequence: SEQ ID NO: 9, SEQ ID NO: 10 or SEQ ID NO: 11.

In a preferred embodiment of the present invention, provided is a c-Met antibody or antigen-binding fragment thereof described above, wherein the antibody heavy chain variable region comprises at least one HCDR region sequence selected from the following sequences or a mutant sequence thereof: SEQ ID NO: 6, SEQ ID NO: 7 and SEQ ID NO: 8.

In a preferred embodiment of the present invention, provided is a c-Met antibody or antigen-binding fragment thereof described above, wherein the antibody light chain variable region comprises at least one LCDR region sequence selected from the following sequences or a mutant sequence thereof: SEQ ID NO: 9, SEQ ID NO: 10 and SEQ ID NO: 11.

In a preferred embodiment of the present invention, provided is a c-Met antibody or antigen-binding fragment thereof described above, wherein the antibody comprises a heavy chain variable region sequence selected from the group consisting of SEQ ID NO: 6 (HCDR1), SEQ ID NO: 7 (HCDR2) and SEQ ID NO: 8 (HCDR3), or a mutant sequence thereof, and a light chain variable region sequence selected from the group consisting of SEQ ID NO:9 (LCDR1), SEQ ID NO: 10 (LCDR2) and SEQ ID NO: 11 (LCDR3), or a mutant sequence thereof.

In a preferred embodiment of the present invention, provided is a c-Met antibody or antigen-binding fragment thereof described above, wherein the mutant sequences of CDR regions are sequences having 1-3 amino acid mutations that optimize antibody activity, wherein the mutant sequence of LCDR1 is preferably SEQ ID NO: 12.

In a preferred embodiment of the present invention, provided is a c-Met antibody or antigen-binding fragment thereof described above, wherein the c-Met antibody or the antigen-binding fragment thereof is a murine antibody or fragment thereof.

In a preferred embodiment of the present invention, provided is a c-Met antibody or antigen-binding fragment thereof described above, wherein the heavy chain variable region sequence of the murine antibody is shown as SEQ ID NO: 4.

In a preferred embodiment of the present invention, provided is a c-Met antibody or antigen-binding fragment thereof described above, wherein the light chain variable region sequence of the murine antibody is shown as SEQ ID NO: 5.

In a preferred embodiment of the present invention, provided is a c-Met antibody or antigen-binding fragment thereof described above, wherein the heavy chain variable region of the murine antibody is shown as SEQ ID NO: 4, and the light chain variable region of the murine antibody is shown as SEQ ID NO: 5.

In a preferred embodiment of the present invention, provided is a murine antibody or fragment thereof described above, wherein the heavy chain variable region of the antibody further comprises a heavy chain FR region derived from murine IgG1, or a variant thereof, murine IgG2, or a variant thereof, murine IgG3, or a variant thereof, or murine IgG4, or a variant thereof.

In a preferred embodiment of the present invention, provided is a murine antibody or fragment thereof described above, which further comprises a heavy chain constant region derived from murine IgG1, or a variant thereof, murine IgG2, or a variant thereof, murine IgG3, or a variant thereof, or murine IgG4, or a variant thereof.

In a preferred embodiment of the present invention, provided is a murine antibody or fragment thereof described above, wherein the light chain variable region of the antibody further comprises a light chain FR region derived from murine κ chain, or a variant thereof, or murine λ chain, or a variant thereof.

In a preferred embodiment of the present invention, provided is a murine antibody or fragment thereof described above, which further comprises a light chain constant region derived from murine κ chain, or a variant thereof, or murine λ chain, or a variant thereof.

In a preferred embodiment of the present invention, provided is a c-Met antibody or antigen-binding fragment thereof described above, which is a chimeric or humanized antibody or a fragment thereof.

In a preferred embodiment of the present invention, provided is a c-Met antibody or antigen-binding fragment thereof described above, wherein the humanized antibody heavy chain variable region further comprises a heavy chain FR region derived from human IgG1, or a variant thereof, IgG2, or a variant thereof, IgG3, or a variant thereof, or IgG4, or a variant thereof.

In a preferred embodiment of the present invention, provided is a c-Met antibody or antigen-binding fragment thereof described above, wherein the humanized antibody heavy chain variable region comprises heavy chain FR sequence derived from human germline heavy chain, preferably human germline heavy chain IGHV 3-33*01, comprising the framework sequence of the FR1, FR2, FR3 and FR4 regions of human germline heavy chain IGHV 3-33*01, or a mutant sequence thereof, preferably, the mutant sequence comprises 0-10 amino acid back-mutation(s).

In a preferred embodiment of the present invention, provided is a c-Met antibody or antigen-binding fragment thereof described above, wherein the humanized antibody comprises a heavy chain variable region sequence shown as SEQ ID NO: 13-15, or a variant thereof.

In a preferred embodiment of the present invention, provided is a c-Met antibody or antigen-binding fragment thereof described above, wherein the humanized antibody light chain variable region comprises a light chain FR region derived from a human germline light chain, preferably human germline light chain IGKV085 or IGKV4-1*01, including a framework sequence of FR1, FR2, FR3 and FR4 regions of the human germline light chain IGKV085 or IGKV4-1*01, or a mutant sequence thereof, preferably, the mutant sequence comprises 0-10 amino acid back-mutation(s).

In a preferred embodiment of the present invention, provided is a c-Met antibody or antigen-binding fragment thereof described above, wherein the humanized antibody comprises a light chain variable region sequence selected from SEQ ID NO: 16-18, or a variant thereof.

In a preferred embodiment of the present invention, provided is a c-Met antibody or antigen-binding fragment thereof described above, wherein the humanized antibody comprises a heavy chain variable region sequence selected from SEQ ID NO: 13-15 and a light chain variable region sequence selected from SEQ ID NO: 16-18.

In a preferred embodiment of the present invention, provided is a c-Met antibody or antigen-binding fragment thereof described above, which comprises a combination of a heavy chain variable region sequence and a light chain variable region sequence selected from any one of a) to c):
 a) Heavy chain variable region sequence of SEQ ID NO: 13, and light chain variable region sequence of SEQ ID NO: 16;
 b) Heavy chain variable region sequence of SEQ ID NO: 14, and light chain variable region sequence of SEQ ID NO: 17; or
 c) Heavy chain variable region sequence of SEQ ID NO: 15, and light chain variable region sequence of SEQ ID NO: 18.

In a preferred embodiment of the present invention, provided is a c-Met antibody or antigen-binding fragment thereof described above, wherein the heavy chain constant region of humanized antibody comprises a constant region derived from human IgG1, or a variant thereof, human IgG2, or a variant thereof, human IgG3, or a variant thereof, or human IgG4, or a variant thereof, preferably a constant region derived from human IgG1, or a variant thereof, human IgG2, or a variant thereof or human IgG4, or a variant thereof, most preferably a constant region derived from human IgG2, or a variant thereof.

In a preferred embodiment of the present invention, provided is a c-Met antibody or antigen-binding fragment thereof described above, which comprises a full length heavy chain sequence selected from SEQ ID NO: 23-25 or sequences with at least 90% identity to SEQ ID NO: 23-25.

In a preferred embodiment of the present invention, provided is a c-Met antibody or antigen-binding fragment thereof described above, wherein the light chain variable region of humanized antibody further comprises a light chain FR region selected from human κ or λ chain, or a variant thereof.

In a preferred embodiment of the present invention, provided is a c-Met antibody or antigen-binding fragment thereof described above, wherein the light chain constant region of humanized antibody comprises a constant region selected from human κ or λ chain, or a variant thereof.

In a preferred embodiment of the present invention, provided is a c-Met antibody or antigen-binding fragment thereof described above, which comprises a full-length light chain sequence selected from SEQ ID NO: 26-28 or sequences with at least 90% identity to SEQ ID NO: 26-28.

In a preferred embodiment of the present invention, provided is a c-Met antibody or antigen-binding fragment thereof described above, which comprises a full length heavy chain sequence selected from SEQ ID NO: 23-25 and a full-length light chain sequence selected from SEQ ID NO: 26-28.

In a preferred embodiment of the present invention, provided is a c-Met antibody or antigen-binding fragment thereof described above, wherein the humanized antibody comprises a combination of a full-length light chain sequence and a full-length heavy chain selected from any one of (a) to (c):
 (a) Ab-9: The heavy chain sequence of SEQ ID NO: 23 and the light chain sequence of SEQ ID NO: 26;
 (b) Ab-10: The heavy chain sequence of SEQ ID NO: 24 and the light chain sequence of SEQ ID NO: 27; or
 (c) Ab-11: The heavy chain sequence of SEQ ID NO: 25 and the light chain sequence of SEQ ID NO: 28.

In a preferred embodiment of the present invention, provided is a c-Met antibody or antigen-binding fragment thereof described above, wherein the antigen-binding fragment is Fab, Fv, scFv or F(ab')2.

The present invention further provides a DNA molecule encoding a c-Met antibody or the antigen-binding fragment thereof described above, and expressing a precursor product.

The present invention further provides an expression vector comprising a DNA molecule as described above.

The present invention further provides a host cell transformed with an expression vector as described above.

In one preferred embodiment of present invention, provided is a host cell as described above, wherein said host cell is preferably a mammalian cell, more preferably CHO cells.

The present invention further provides a pharmaceutical composition, comprising a c-Met antibody or antigen-binding fragment thereof as described above; and one or more pharmaceutically acceptable excipient, diluent or carrier.

The present invention further provides use of a c-Met antibody or antigen-binding fragment thereof according to the present invention, or a pharmaceutical composition according to the present invention in the preparation of a medicament for the treatment of a c-Met-mediated disease or condition, wherein the disease or condition is preferably cancer, more preferably a cancer that expresses c-Met, most preferably a cancer selected from gastric cancer, pancreatic cancer, lung cancer, intestinal cancer, kidney cancer, melanoma, and non-small cell lung cancer, and most preferably gastric cancer or non-small cell lung cancer.

The present invention further provides a method for treating or preventing a c-Met-mediated disease or condition, the method comprising: administering a therapeutically effective amount of a c-Met antibody or antigen-binding fragment thereof according to the present invention, or a pharmaceutical composition according to the invention, to a patient in need thereof, wherein the disease or condition is preferably cancer, more preferably a cancer that expresses c-Met, most preferably a cancer selected from gastric cancer, pancreatic cancer, lung cancer, intestinal cancer, kidney cancer, melanoma, and non-small cell lung cancer, and most preferably gastric cancer or non-small cell lung cancer.

The present invention further provides an antibody-cytotoxic drug conjugate of formula (I) or a pharmaceutically acceptable salt or solvate thereof:

$$Ab-[(L_2)t-L_1-D)]y \qquad (I)$$

wherein:
D is a drug unit;
$L_1$ and $L_2$ are linker units;
t is 0 or 1, preferably 1;
y ranges from 1-8, preferably 2-5, and y can be a decimal; and
Ab is an antibody or antigen-binding fragment thereof that specifically binds to c-Met as described above.

In a preferred embodiment of the present invention, provided is an antibody-cytotoxic drug conjugate of formula (I) or a pharmaceutically acceptable salt or solvate thereof according to the invention, wherein -$L_2$- is the compound shown as formula (-$L_2$-):

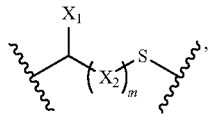

wherein:

$X^1$ is selected from the group consisting of hydrogen, halogen, hydroxyl, cyano, alkyl, alkoxy and cycloalkyl;

$X^2$ is selected from the group consisting of alkyl, cycloalkyl and heterocyclyl;

m is 0-5, preferably 1-3; and

S is a sulfur atom.

In a preferred embodiment of the present invention, provided is an antibody-cytotoxic drug conjugate of formula (I) or a pharmaceutically acceptable salt or solvate thereof according to the invention, wherein the drug unit of D is a cytotoxic agent selected from toxins, chemotherapeutic agents, antibiotics, radioisotopes and nucleolytic enzymes.

In a preferred embodiment of the present invention, provided is an antibody-cytotoxic drug conjugate of formula (I) or a pharmaceutically acceptable salt or solvate thereof according to the invention, wherein the drug unit of D has a structure of formula (D):

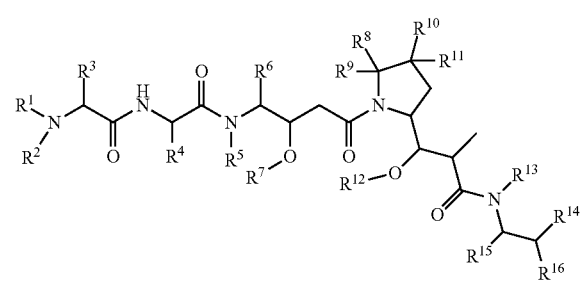

or a tautomer, mesomer, racemate, enantiomer, or diastereomer thereof, or mixtures thereof, or a pharmaceutically acceptable salt thereof:

wherein:

$R^1$-$R^7$ is each selected from the group consisting of hydrogen, halogen, hydroxyl, cyano, alkyl, alkoxy and cycloalkyl;

$R^8$-$R^{11}$ is each optionally selected from the group consisting of hydrogen, halogen, alkenyl, alkyl, alkoxy and cycloalkyl; preferably, at least one of $R^8$-$R^{11}$ is selected from the group consisting of halogen, alkenyl, alkyl and cycloalkyl, and the rest of $R^8$-$R^{11}$ are hydrogen, or any two of $R^8$-$R^{11}$ form a cycloalkyl, and the rest two are each selected from the group consisting of hydrogen, alkyl and cycloalkyl;

$R^{12}$-$R^{13}$ is each selected from the group consisting of hydrogen, alkyl and halogen;

$R^{14}$ is selected from aryl and heteroaryl, wherein the aryl or heteroaryl is optionally further substituted by a substituent group selected from the group consisting of hydrogen, halogen, hydroxy, alkyl, alkoxy and cycloalkyl;

$R^{15}$ is selected from halogen, alkenyl, alkyl, cycloalkyl and COOR$^{17}$;

$R^{16}$ is selected from hydrogen, halogen, hydroxy, cyano, alkyl, alkoxy and cycloalkyl; and $R^{17}$ is selected from hydrogen, alkyl and alkoxy.

In a preferred embodiment of the present invention, provided is an antibody-cytotoxic drug conjugate of formula (I) or a pharmaceutically acceptable salt or solvate thereof according to the invention, wherein $L_2$ is a linker selected from Val-Cit, MC, PAB and MC-PAB, preferably MC.

In a preferred embodiment of the present invention, provided is an antibody-cytotoxic drug conjugate of formula (I) or a pharmaceutically acceptable salt or solvate thereof according to the invention, wherein D is maytansinoid alkaloid; preferably selected from DM1, DM3 and DM4; more preferably DM1.

In a preferred embodiment of the present invention, provided is an antibody-cytotoxic drug conjugate of formula (I) or a pharmaceutically acceptable salt or solvate thereof according to the invention, wherein $L_2$ is selected from the group consisting of N-succinimidyl 4-(2-pyridylthio) valerate (SPP), N-succinimidyl 4-(N-maleimidomethyl)-cyclohexane-1-carboxylic acid esters (SMCC), and N-succinimidyl (4-iodo-acetyl) aminobenzoate (SIAB); preferably SPP or SMCC.

In a preferred embodiment of the present invention, provided is an antibody-cytotoxic drug conjugate of formula (I) or a pharmaceutically acceptable salt or solvate thereof according to the invention, wherein D is a camptothecin alkaloid; preferably selected from CPT, 10-hydroxy-CPT, CPT-11 (Irinotecan), SN-38 and topotecan, more preferably SN-38.

In a preferred embodiment of the present invention, provided is an antibody-cytotoxic drug conjugate of formula (I) or a pharmaceutically acceptable salt or solvate thereof according to the invention, wherein said linker $L_2$ is selected from the structure of Val-Cit, MC, PAB and MC-PAB; preferably MC or MC-vc-PAB.

In a preferred embodiment of the present invention, provided is an antibody-cytotoxic drug conjugate of formula (I) or a pharmaceutically acceptable salt or solvate thereof according to the invention, which is a conjugated drug of formula (II) or a pharmaceutically acceptable salt or solvate thereof:

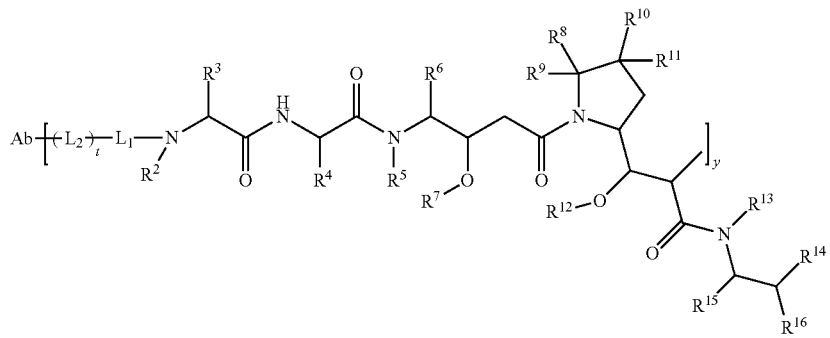

(II)

wherein:
$R^2$-$R^{16}$ are as defined in formula (D); and
Ab, t, y, $L_1$, $L_2$ are as defined in formula (I).

In a preferred embodiment of the present invention, provided is an antibody-cytotoxic drug conjugate of formula (I) or a pharmaceutically acceptable salt or solvate thereof according to the invention, which is a conjugated drug of formula (III) or a pharmaceutically acceptable salt or solvate thereof:

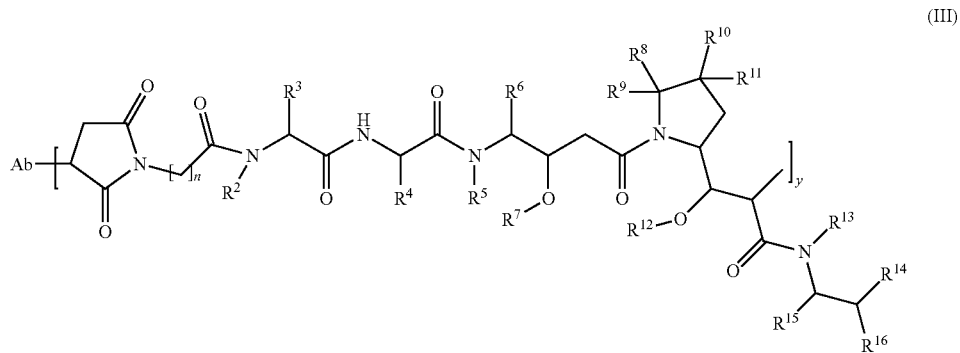

(III)

wherein:
$R^2$-$R^{16}$ are as defined in formula (D);
Ab, t, y, $L_1$, $L_2$ are as defined in formula (I); and
n is 3-6, preferably 5.

In a preferred embodiment of the present invention, provided is an antibody-cytotoxic drug conjugate of formula (I) or a pharmaceutically acceptable salt or solvate thereof according to the invention, which is a conjugated drug of formula (IV) or a pharmaceutically acceptable salt or solvate thereof:

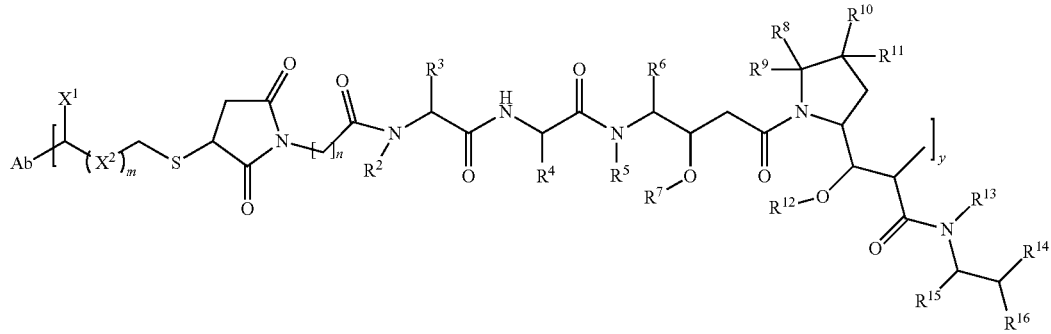

(IV)

wherein:

R²-R¹⁶ are as defined in formula (D);

Ab, y are as defined in formula (I);

n is as defined in formula (III); and

X¹, X², m are as defined in formula L2.

In a preferred embodiment of the present invention, provided is an antibody-cytotoxic drug conjugate of formula (I) or a pharmaceutically acceptable salt or solvate thereof according to the invention, which is a conjugated drug of formula (V) or a pharmaceutically acceptable salt or solvate thereof:

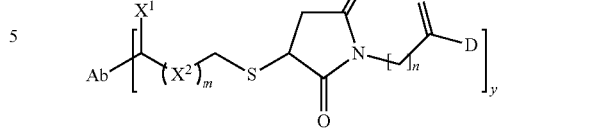

(V)

wherein:
Ab, D, y are as defined in formula (I);
n is as defined in formula (III); and
X¹, X², m are as defined in formula L2.

Structures of antibody-cytotoxic drug conjugates or pharmaceutically acceptable salts or solvates thereof according to the invention include but are not limited to:

| No. | Structure and denomination |
|---|---|
| Example 13 | ADC-1<br>Anti-c-Met antibody Ab-10-toxin MC-MMAF conjugate |
| Example 14 | ADC-2<br>Anti-c-Met antibody Ab-10-toxin MC-VC-PAB-MMAF conjugate |
| Example 15 | ADC-3<br>Anti-c-Met antibody Ab-10-toxin MC-VC-PAB-MMAF conjugate |
| Example 16 | ADC-4<br>Anti-c-Met antibody Ab-10-toxin MC-MMAE conjugate |

| No. | Structure and denomination |
|---|---|
| Example 17 | ADC-5<br>Anti-c-Met antibody Ab-9-toxin MC-MMAE conjugate |
| Example 18 | ADC-6<br>Anti-c-Met antibody Ab-9-toxin MC-MMAF conjugate |
| Example 19 | ADC-7<br>Anti-c-Met antibody Ab-9-toxin MC-VC-PAB-MMAF conjugate |
| Example 20 | ADC-8<br>Anti-c-Met antibody Ab-9-toxin MC-VC-PA13-MMAE conjugate |
| Example 21 | ADC-9<br>Anti-c-Met antibody Ab-10-toxin SMCC-DM1 conjugate |

| No. | Structure and denomination |
|---|---|
| Example 22 | 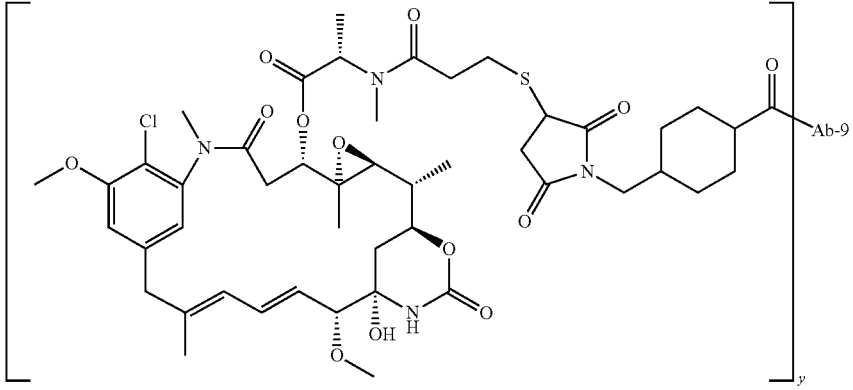
ADC-10
Anti-c-Met antibody Ab-9-toxin SMCC-DM1 conjugate |
| Example 23 | 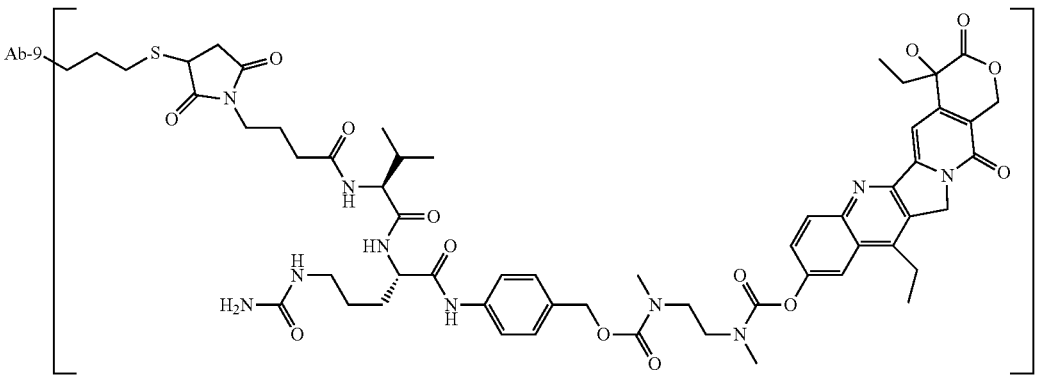
ADC-11
Anti-c-Met antibody Ab-9-toxin -SN-38 conjugate |
| Example 24 | 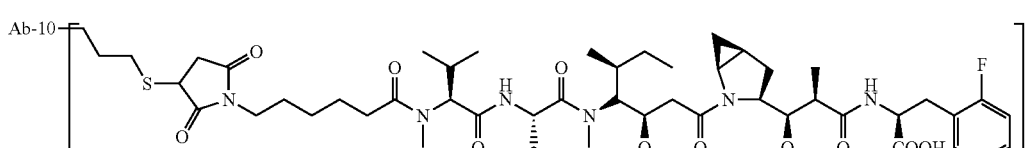
ADC-12
Anti-c-Met antibody Ab-10-toxin conjugate |
| Example 25 | 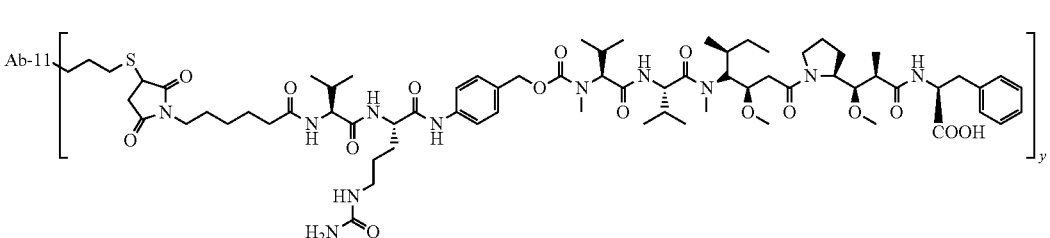
ADC-13
Anti-c-Met antibody Ab-11-toxin MC-VC-PAB-MMAF conjugate |

-continued

| No. | Structure and denomination |
|---|---|
| Example 26 | 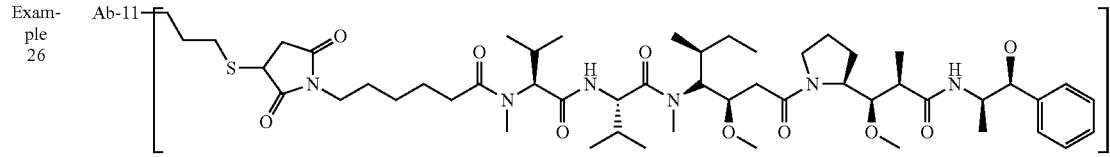<br>ADC-14<br>Anti-c-Met antibody Ab-11-toxin MC-MMAE conjugate |
| Example 27 | 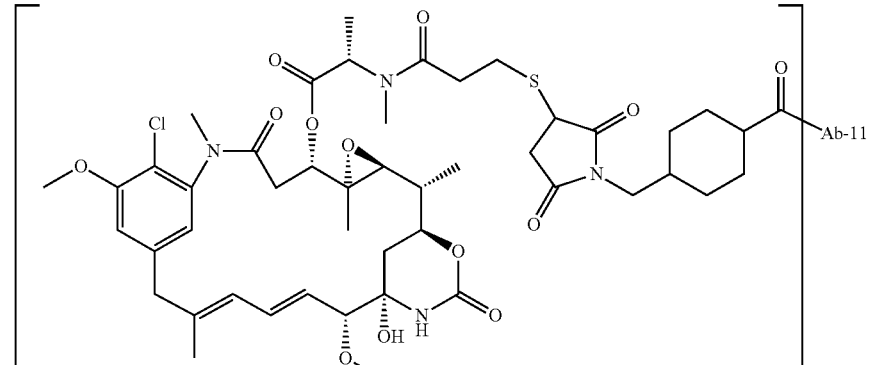<br>ADC-15<br>Anti-c-Met antibody Ab-11-toxin SMCC-DM1 conjugate | wherein Ab-9, Ab-10, Ab-11 are c-Met antibodies as defined above, y is 1-8, preferably 2-5.

Wherein, y ranges from 1-8; preferably 1-4.

The present invention further provides a process of preparing an antibody-cytotoxic drug conjugate of formula (V), comprising a step of:

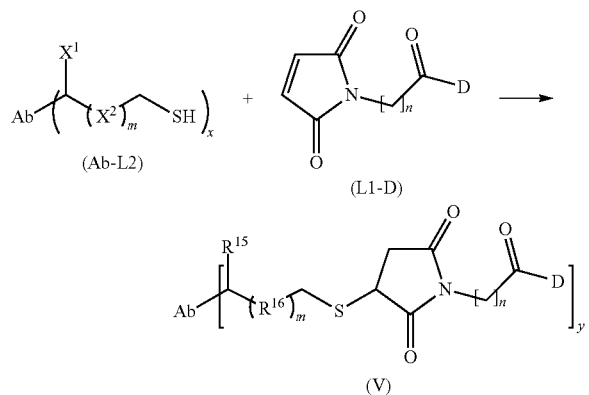

a compound of the general formula (Ab-L2) is reacted with a compound of the general formula (L1-D) in an organic solvent to obtain a compound of the general formula (V); wherein the organic solvent is preferably acetonitrile or ethanol;

wherein:

Ab is an antibody or antigen-binding fragment thereof that specifically binds to a c-Met receptor according to the present invention;

$X^1$ is selected from the group consisting of hydrogen, halogen, hydroxyl, cyano, alkyl, alkoxy and cycloalkyl;

$X^2$ is selected from the group consisting of alkyl, cycloalkyl and heterocyclyl;

x is 0-5, preferably 1-3; and m is 0-5, preferably 1-3.

In a preferred embodiment of the present invention, provided is an antibody-cytotoxic drug conjugate or a pharmaceutically acceptable salt or solvate thereof according to the invention, which has cytotoxic activity in vitro or in vivo.

The present invention further relates to a pharmaceutical composition comprising a therapeutically effective amount of a c-Met antibody or antigen-binding fragment thereof, or an antibody-cytotoxic drug conjugate or a pharmaceutically acceptable salt or solvate thereof, according the present invention, and pharmaceutically acceptable carrier, diluent or excipient.

The present invention further relates to a use of a c-Met antibody or antigen-binding fragment thereof according to the present invention, or an antibody-cytotoxic drug conjugate or a pharmaceutically acceptable salt or solvate thereof according the present invention, or a pharmaceutical composition comprising the same according to the present invention, in the preparation of a medicament for the treatment of a c-Met-mediated disease or condition, wherein the disease or condition is preferably cancer, more preferably a cancer that expresses c-Met, most preferably a cancer selected from gastric cancer, pancreatic cancer, lung cancer, intestinal cancer, kidney cancer, melanoma, and non-small cell lung cancer, and most preferably gastric cancer, pancreatic cancer, non-small cell lung cancer or kidney cancer.

The present invention further relates to a method for treating or preventing a c-Met-mediated disease or condition, the method comprises administering a therapeutically effective amount of a c-Met antibody or antigen-binding fragment thereof, or an antibody-cytotoxic drug conjugate or a pharmaceutically acceptable salt or solvate thereof, or a pharmaceutical composition comprising the same, according to the invention, to a patient in need thereof, wherein the disease or condition is preferably cancer, more preferably a cancer that expresses c-Met, most preferably a cancer selected from gastric cancer, pancreatic cancer, lung cancer, intestinal cancer, kidney cancer, melanoma, and non-small cell lung cancer, and most preferably gastric cancer, pancreatic cancer, non-small cell lung cancer or kidney cancer.

BRIEF DESCRIPTION OF THE DRAWINGS

FIG. 1 shows the tumor inhibition effect of an anti-c-Met antibody and an ADC molecule of the invention, and the result show that the new ADC can achieve complete inhibition of a tumor by the conjugated toxin, whereas the antibody alone can not achieve such complete inhibition. The results also show that coupling of toxins does not affect $T_{1/2}$ of the ADC molecule in this invention, and the ADC drug of the present invention does not show in vivo toxicity in mice.

DETAILED DESCRIPTION OF THE INVENTION

1. Terms

In order to make the invention more readily understood, certain technical and scientific terms are specifically defined below. Unless specifically defined elsewhere in this document, all other technical and scientific terms used herein have the meaning commonly understood by one of ordinary skill in the art to which this invention belongs.

As used herein, the single-letter code and the three-letter code for amino acids are as described in *J. Biol. Chem*, 243, (1968) p 3558.

The term "c-Met" or "c-Met polypeptide" or "c-Met receptor" refers to a receptor tyrosine kinase that binds to a cell growth factor (HGF). In the present invention, unless specified specifically, such as murine c-Met (m-c-Met) or monkey c-Met (cyno-c-Met), the term c-Met usually refers to human c-Met (h-c-Met). The human, mouse and cynomolgus monkey c-Met used in the present invention are encoded by nucleotide sequences, or have polypeptide sequences, provided by GenBank, for example, the human peptide is encoded by the nucleotide sequence provided in GenBank Accession No. NM_000245, or the human protein or its extracellular domain have the polypeptide sequence provided in GenBank Accession No. NP_000236. The original single-stranded precursor proteins are cleaved after translation to produce alpha and beta subunits, which are linked by disulfide bonds to form mature receptors. The receptor tyrosine kinase c-Met is involved in cell processes including, for example, the process of migration, invasion and morphogenesis of tissue regeneration associated with embryogenesis.

The term "c-Met-related disorder or condition" refers to any disease, condition or disorder originating from adverse or lack of c-Met expression, adverse regulation or lack of regulation, or deleterious activity or lack of activity, or refers to any disease, condition or disorder which could be regulated, treated or cured by modulating c-Met expression or activity. The activation of the HGF/c-Met pathway can be expected, for example, in most cancer patients, or in patients whose disease is indeed driven by changes associated with the c-Met pathway. For example, upregulation is due to different mechanisms, such as overexpression of HGF and/or c-Met, or by constitutive activation of c-Met mutations. C-Met-related disorders or conditions include, but are not limited to, proliferative diseases and disorders and inflammatory diseases and disorders. Proliferative diseases include, but are not limited to, for example, cancer, including, for example, gastric cancer, esophageal cancer, kidney cancer including papillary renal cell carcinoma, lung cancer, glioma, head and neck cancer, epithelial cancer, skin cancer, leukemia, lymphoma, myeloma, brain cancer, pancreatic cancer, colorectal cancer, gastrointestinal cancer, intestinal cancer, genital cancer, urinary cancer, melanoma, prostate cancer, and other tumors known to those skilled in the art. Inflammatory diseases include, but are not limited to bacterial infections, including infections caused by *Listeria* bacteria.

"Antibody" in this invention refers to immunoglobulin, a four-peptide chain structure formed by two identical heavy chains and two identical light chains connected by interchain disulfide bonds. Different immunoglobulin heavy chain constant regions have different amino acid compositions and sequences, and thus present different kinds of antigenicity. Accordingly, immunoglobulins can be divided into five categories, also referred as immunoglobulin isotypes, namely IgM, IgD, IgG, IgA and IgE; the corresponding heavy chains thereof are μ chain, δ chain, γ chain, α chain, and ε chain, respectively. According to the amino acid composition of the hinge region and the number and location of heavy chain disulfide bonds, immunoglobulins can be divided into different sub-categories, for example, IgG can be divided into IgG1, IgG2, IgG3, and IgG4. Light chains can be divided into κ or λ chains, based on different constant regions. Each category of Ig among IgM, IgD, IgG, IgA and IgE involves a κ or λ chain.

At the N-terminal of the antibody heavy and light chains, about 110 amino acids vary largely, and this region is known as the variable region (V region); the amino acid sequence at the C-terminus is relatively stable, and this region is known as the constant region (C region). The variable region comprises three hypervariable regions (HVR) and four FR regions (FR) with relatively conserved sequences. Three hypervariable regions determine the specificity of the antibody, also known as complementarity determining region (CDR). Each light chain variable region (LCVR) and each heavy chain variable region (HCVR) is composed of three CDRs and four FRs, arranged from the amino terminal to the carboxyl terminal as: FR1, CDR1, FR2, CDR2, FR3, CDR3, and FR4. The three light chain CDRs are referred to as LCDR1, LCDR2, and LCDR3; and the three heavy chain CDR regions are referred to as HCDR1, HCDR2 and HCDR3. The number and location of the CDR amino acid residues in the LCVRs and HCVRs of the antibody or antigen binding fragment herein correspond with known Kabat numbering criteria (LCDR1-3, HCDE2-3), or correspond with kabat and chothia numbering criteria (HCDR1).

The term "murine antibody" in the present invention refers to an anti-human c-Met monoclonal antibody prepared from mouse according to the knowledge and skills of the field. During the preparation, a test object was injected with c-Met antigen, and then a hybridoma expressing an antibody possessing the desired sequence or functional characteristics was isolated. In a preferred embodiment of the present invention, the murine c-Met antibody or antigen binding fragment thereof, further comprises a light chain constant region of murine κ or λ chain, or a variant thereof, or further comprises a heavy chain constant region of murine IgG1, IgG2, IgG3 or IgG4, or a variant thereof.

The term "chimeric antibody" refers to an antibody that is obtained by fusing the variable region of a murine antibody to the constant region of a human antibody, wherein the chimeric antibody can alleviate the murine antibody-induced immune response. To establish a chimeric antibody, a hybridoma secreting a specific murine monoclonal antibody is firstly established, the variable region gene is cloned from the murine hybridoma, and then cloned into the constant region gene of a human antibody for recombinant expression.

The term "humanized antibody", also known as humanized CDR-grafted antibody, refers to an antibody generated by grafting murine CDR sequences onto the framework of a human antibody variable region, comprising different types of sequences of a human germline antibody framework. Humanized antibodies avoid the strong antibody immune response induced by chimeric antibodies that carry a large number of murine components. The framework sequences can be obtained from public DNA databases covering germline antibody gene sequences or from published references. For example, germline DNA sequences of human heavy and light chain variable region genes can be found in the "VBase" human germline sequence database (available on website: www.mrccpe.com.ac.uk/vbase), as well as found in Kabat, E A, et al, 1991 *Sequences of Proteins of Immunological Interest,* 5th Ed. In a preferred embodiment of the invention, the murine CDR sequences of c-Met humanized antibody are selected from SEQ ID NOs: 6, 7, 8, 9, 10, and 11. Human antibody variable region frameworks were designed and selected, wherein the light chain FR region sequences of said antibody light chain variable regions were derived from human germline light chain sequences, preferably selected from human germine light chain IGKV085 or IGKV 4-1*01, comprising FR1, FR2, FR3 and FR4 regions of human germline light chain IGKV085 and IGKV 4-1*01; the heavy chain FR region sequence of said antibody heavy chain variable region is derived from human germline heavy chain sequences, preferably selected from human germline heavy chain IGHV 3-33*01, comprising FR1, FR2, FR3 and FR4 regions of human germline heavy chain IGHV 3-33*01. To avoid decrease of activity caused by decrease of immunogenicity, a minimum of back mutation(s) could be introduced into a human antibody variable region to maintain the activity.

There are multiple methods available in the art to generate humanized antibodies. For example, humanized antibodies can be produced by obtaining nucleic acid sequences encoding the HCVR and LCVR of a parent antibody (e.g., a murine antibody or antibody produced by a hybridoma) that specifically binds c-Met, and grafting such nucleic acid sequences onto selected human framework-encoding nucleic acid sequences. Optionally, a CDR region can be optimized by mutagenesis randomly or at particular locations in order to substitute one or more amino acids in the CDR with a different amino acid prior to grafting the CDR onto the framework region. Alternatively, a CDR can be optimized subsequent to insertion into the human framework region using methods available to one of skilled in the art. Preferably, a "humanized antibody" has CDRs that originate from or are derived from a parent antibody (i.e., a non-human antibody, preferably a mouse monoclonal antibody), while framework and constant regions, to the extent they are present, (or a significant or substantial portion thereof, i.e., at least about 90%, 92%, 94%, 95%, 96%, 97%, 98% or 99%) are encoded by nucleic acids that occur in the human germline immunoglobulin region (see, e.g., the International ImMunoGeneTics Database) or in recombined or mutated forms thereof, regardless of whether said antibodies are produced in a human cell. Preferably, at least two, three, four, five or six CDRs of a humanized antibody are optimized from the CDRs of a non-human parent antibody from which the humanized antibody was derived, to generate a desired property, e.g., improved specificity, affinity or neutralization, which can be identified by a screening assay, e.g., an ELISA assay. Preferably, an optimized CDR in an antibody of the invention comprises at least one amino acid substitution when compared with that present in the parent antibody. When compared with CDRs of parent antibodies, certain amino acid substitutions in the CDRs of humanized antibodies of the invention (see example 6 herein) decrease the likelihood of instability of the antibody (e.g., removal of Asn residues from CDRs) or decrease the likelihood of immunogenicity of the antibody when administered to a human subject (e.g., as predicted by IMMUNOFILTER™ Technology).

After the CDR-encoding sequences are grafted onto the selected human framework encoding sequences, the resultant DNA sequences encoding the humanized variable heavy and variable light chain sequences are then expressed to produce a humanized antibody that binds c-Met. The humanized HCVR and LCVR can be expressed as part of a whole anti-c-Met antibody molecule, i.e., as a fusion protein with human constant domain sequences. However, the HCVR and LCVR sequences can also be expressed in the absence of constant sequences to produce a humanized anti-c-Met scFv.

References further describing methods involved in humanization of a mouse antibody that can be used include e.g., Queen et al., *Proc. Natl. Acad. Sci. USA* 88: 2869, 1991 and the method of Winter and co-workers [Jones et al., *Nature,* 321:522 (1986); Riechmann et al., *Nature,* 332:323-327 (1988); Verhoeyen et al., *Science,* 239:1534 (1988)].

"Antigen-binding fragment" in the present invention refers to a Fab fragment, a Fab' fragment, a F(ab')$_2$ fragment having antigen-binding activity, as well as an Fv fragment or an scFv fragment, binding with human c-Met. It comprises one or more CDRs of antibodies described in the present invention, selected from the group consisting of SEQ ID NOs: 3-8. An Fv fragment is a minimum antibody fragment comprising a heavy chain variable region, a light chain variable region, and all antigen-binding sites, without a constant region. Generally, an Fv antibody further comprises a polypeptide linker between the VH and VL domains, and is capable of forming a structure necessary for antigen binding. Also, different linkers can be used to connect the variable regions of two antibodies to form a polypeptide chain, referred to as a single chain antibody or a single chain Fv (scFv). An scFv can also be used with other antibodies such as an anti-EGFR antibody to construct a bispecific antibody. The term "binding with c-Met" in this invention means being capable of interacting with human c-Met. The term "antigen-binding sites" in the present invention refers to discontinuous, three-dimensional sites on the antigen, recognized by the antibody or the antigen-binding fragment of the present invention. As used herein, the term "ADCC", namely antibody-dependent cell-mediated cytotoxicity, means that the cells expressing Fc receptors directly kill the target cells coated by an antibody by recognizing the Fc segment of the antibody. ADCC effector function of the antibody can be reduced or eliminated by modifying the Fc segment in IgG. The modification refers to mutations on the antibody heavy chain constant region, such as mutations selected from N297A, L234A, L235A in IgG1; IgG2/4 chimera; F235E, or L234A/E235A mutations in IgG4.

As used herein, a fusion protein described in the present invention is a protein product obtained by co-expressing two genes via recombinant DNA technology. A recombinant c-Met extracellular domain Fc fusion protein is obtained by co-expressing a c-Met extracellular domain and a human antibody Fc fragment via recombinant DNA technology. The c-Met extracellular domain refers to the moiety of c-Met outside the cytomembrane.

The engineered antibody or antigen-binding fragment of the present invention can be prepared and purified using conventional methods. For example, cDNA sequences encoding a heavy chain (SEQ ID NO: 4) and a light chain (SEQ ID NO: 5) can be cloned and recombined into pEE6.4 expression vector (Lonza Biologics). The recombined immunoglobulin expression vector can then stably transfect CHO cells. As a more recommended method well known in the art, mammalian expression system will make antibodies glycosylated, typically at the highly conserved N-terminus in the FC region. Stable clones can be obtained through expression of an antibody specifically binding to human c-Met. Positive clones can be expanded in a serum-free culture medium for antibody production in bioreactors. Culture medium, into which an antibody has been secreted, can be purified by conventional techniques. For example, the medium can be conveniently applied to a Protein A or G Sepharose FF column that has been equilibrated with a compatible buffer. The column is washed to remove non-specific binding components. The bound antibody is eluted by PH gradient and the antibody fragments are detected by SDS-PAGE, and then collected. The antibody can be filtered and concentrated using common techniques. Soluble aggregate and multimers can be effectively removed by common techniques, including size exclusion or ion exchange. The obtained product can be immediately frozen, for example at −70° C., or can be lyophilized.

The term "antibody," in this invention refers to a monoclonal antibody. As used herein, the term "monoclonal antibody" or "mAb" refers to an antibody secreted by a clone derived from a single cell strain. The cell strain is not limited to eukaryotic, prokaryotic, or phage clonal cell lines. Monoclonal antibodies or antigen-binding fragments can be obtained by recombinantion, for example, hybridoma techniques, recombinant techniques, phage display techniques, synthetic techniques (such as CDR-grafting), or other techniques readily known in the art.

"Administration" and "treatment," as they apply to an animal, human, experimental subject, cell, tissue, organ, or biological fluid, refer to contacting an exogenous pharmaceutical, therapeutic, diagnostic agent, or composition with the animal, human, subject, cell, tissue, organ, or biological fluid. "Administration" and "treatment" can refer, e.g., to therapeutic, pharmacokinetic, diagnostic, research, and experimental methods. Treatment of a cell encompasses contacting an agent with the cell, as well as contacting an agent with a fluid, where the fluid is in contact with the cell.

"Treat" means to administer a therapeutic agent, such as a composition comprising any of the binding compounds of the present invention, internally or externally to a patient having one or more disease symptoms for which the agent has known therapeutic activity. Typically, the therapeutic agent is administered in an amount effective to alleviate one or more disease symptoms in the treated patient or population, by inducing the regression of or inhibiting the progression of such symptom(s) to any clinically measurable degree. The amount of a therapeutic agent that is effective to alleviate any particular disease symptom (also referred to as "therapeutically effective amount") can vary according to factors such as the disease state, age, and weight of the patient, and the ability of the drug to elicit a desired response in the patient. Whether a disease symptom has been alleviated can be assessed by any clinical measurement typically used by physicians or other skilled healthcare providers to assess the severity or progression status of that symptom. While an embodiment of the present invention (e.g., a treatment method or article of manufacture) may not be effective in alleviating the disease symptom(s) of interest in every patient, it should alleviate the target disease symptom (s) of interest in a statistically significant number of patients as determined by any statistical test known in the art such as the Student's t-test, the chi-square test, the U-test according to Mann and Whitney, the Kruskal-Wallis test (H-test), Jonckheere-Terpstra-test and the Wilcoxon-test.

"Conservative modification" or "conservative replacement or substitution" refers to substitutions of amino acids in a protein with other amino acids having similar characteristics (e.g. charge, side-chain size, hydrophobicity/hydrophilicity, backbone conformation and rigidity, etc.), such that the changes can frequently be made without altering the biological activity of the protein. Those skilled in this art recognize that, in general, single amino acid substitutions in non-essential regions of a polypeptide do not substantially alter biological activity (see, e.g., Watson et al. (1987) Molecular Biology of the Gene, The Benjamin/Cummings Pub. Co., p. 224 (4.th Ed.)). In addition, substitutions of structurally or functionally similar amino acids are less likely to disrupt biological activity.

The term "consisting essentially of" or variations thereof as used throughout the specification and claims, indicates the inclusion of any recited elements or group of elements, and optionally inclusion of other elements, of similar or different nature than the recited elements, which do not materially change the basic or novel properties of the specified dosage regimen, method, or composition. As a nonlimiting example, a binding compound which consists essentially of a recited amino acid sequence can also include one or more amino acids that do not materially affect the properties of the binding compound.

"Effective amount" encompasses an amount sufficient to ameliorate or prevent a symptom or sign of a medical condition. Effective amount also means an amount sufficient to allow or facilitate diagnosis. An effective amount for a particular patient or veterinary subject can vary depending on factors such as the condition being treated, the general health of the patient, the route and dose of administration and the severity of side effects. An effective amount can be the maximal dose or dosing regimen that avoids significant side effects or toxic effects.

"Exogenous" refers to substances that are produced outside an organism, cell, or human body, depending on the context. "Endogenous" refers to substances that are produced within a cell, organism, or human body, depending on the context.

"Homology" refers to sequence similarity between two polynucleotide sequences or between two polypeptides. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared and then multiplied by 100. For example, if 6 of 10 positions in two sequences are matched or homologous when the sequences are optimally aligned, then the two sequences are 60% homologous. Generally, the comparison is made when two sequences are aligned to give maximum percent homology.

"Optional" or "optionally" means that the event or situation that follows can but does not necessarily occur, and the description includes the instances in which the event or situation does or does not occur. For example, "optionally comprises 1-3 antibody heavy chain variable regions" means that the antibody heavy chain variable region with specific sequence can be, but is not necessarily, present.

"Pharmaceutical composition" refers to a mixture comprising one or more compounds according to the present invention or a physiologically/pharmaceutically acceptable salt or prodrug thereof with other chemical components, as well as additional components such as physiologically/pharmaceutically acceptable carriers and excipients. The pharmaceutical composition aims at promoting the administration to an organism, facilitating the absorption of the active ingredient and thereby exerting a biological effect.

Preparation of Conventional Pharmaceutical Compositions can be Found in Chinese Pharmacopoeia.

The term "carrier" is applied for the drug of the present invention, and refers to a system that can change the manner in which a drug enters the human body, and change the in vivo distribution of the drug, control the release rate of the drug, and delivery of the drug to the target organ. Drug carrier release and targeting systems are capable of reducing drug degradation and loss, decreasing side effects, and improving bioavailability. For example, a macromolecular surfactant used as a carrier can self-assemble to form aggregates in various forms because of its unique amphiphilic structure, and preferred examples include micelles, emulsions, gels, liquid crystals, vesicles, etc. These aggregates not only have the ability to entrap drug molecules, but also display good membrane permeability, and can be used as excellent drug carriers.

The term "diluent" is also referred to as filler, and its main purpose is to increase the tablet weight and volume. The addition of diluent is not only to ensure a certain volume, but also to reduce the dose deviation of the main components and to improve the compression moldability of the drug. When pharmaceutical tablets contain an oily component, an absorbent must be added to absorb the oil material, and maintain the "dry" state, which facilitates tablet formation.

The term "pharmaceutically acceptable salt" refers to a salt form of a ligand-cytotoxic drug conjugate of the present invention, wherein the salt is safe and effective, and has the desired biological activity in mammals in vivo. The antibody-drug conjugate compound of the present invention comprises at least one amino group, by which the antibody-drug conjugate compound can form a salt with acid.

The term "solvate" refers to a pharmaceutically acceptable solvate formed by a ligand-drug conjugate of the present invention with one or more solvent molecule(s).

The term "ligand" is a macromolecular compound which is able to recognize and bind to the target cell-associated antigens or receptors. The role of the ligand is to deliver the drug to the target cell population bound to the ligand. The ligand includes, but is not limited to, proteinaceous hormones, lectins, growth factors, antibodies and other molecules capable of binding to cells.

The therapeutic agent is a molecule or atom that is administered separately, simultaneously or successively with a binding moiety, such as an antibody or antibody fragment, or a sub-fragment thereof, and is useful for the treatment of the disease. Examples of therapeutic agents include, but are not limited to, antibodies, antibody fragments, conjugates, drugs, cytotoxic agents, apoptotic agents, toxins, nucleases (including DNase and RNase), hormones, immunomodulators, chelating agents, Boron compounds, photosensitizers or dyes, radioisotopes or radionuclides, oligonucleotides, interfering RNAs, peptides, antiangiogenic agents, chemotherapeutic agents, cytokines, chemokines, prodrugs, enzymes, binding proteins or peptides, or a combination thereof.

The conjugate is an antibody component or other targeting moiety conjugated to a therapeutic agent as described above. As used herein, the terms "conjugate" and "immunoconjugate" are used interchangeably.

The term "cytotoxic agent" as used herein refers to a substance that inhibits or prevents the function of the cell and/or causes cell death or destruction.

"Toxin" refers to any substance capable of adversely affecting cell growth or proliferation.

"Chemotherapeutic agent" refers to a chemical compound that can be used to treat cancer. The definition also includes anti-hormonal agents that regulate, reduce, block or inhibit the effects of hormones that promote cancer growth, and chemotherapeutic agents are often in the form of systemic treatment that themselves can be hormones.

Auristatins are completely synthetic drugs with a relatively easily formed chemical structure that facilitates the optimization of physical properties and druggability. Auristatin derivatives used for antibody conjugation include monomethyl auristatin E (MMAE) and monomethyl auristatin F (MMAF). MMAE is a synthetic pentapeptide derived from the natural tubulin polymerase inhibitor dolastatin-10, synthesized by adding 2-amino-1-phenylpropyl-1-ol at the C-terminus. The MMAE inhibitory activities against a variety of human tumor cell lines are less than one nanomolar. In order to reduce the cytotoxic activity of MMAE itself, a phenylalanine is introduced at the C-terminus of dolastatin-10 in the case of MMAF. Due to the introduction of a carboxyl group in the structure, MMAF has a poor capacity in passing through the membrane, and therefore the biological activity against cells is significantly decreased, but the inhibitory activity against cells after conjugation to an antibody is increased substantially (U.S. Pat. No. 7,750,116).

The term "tubulin inhibitor" refers to a class of compounds that exert an anti-tumor effect by inhibiting or promoting polymerization of tublin, and consequently interfering with the cell mitosis process. Non-limiting examples include maytansinoids, calicheamicins, taxanes, vincristines, colchicines, and Dolastatins/Auristatins, preferably maytansinoids or Dolastatins/Auristatins; more preferably compounds of formula $D_1$ or $D_M$.

CPT is an acronym for camptothecin, and in this application CPT is used to refer to camptothecin itself or analogs or derivatives of camptothecin. The structures of camptothecin having the indicated number and the rings labeled with the letters A-E and some analogs thereof are provided in the following formula.

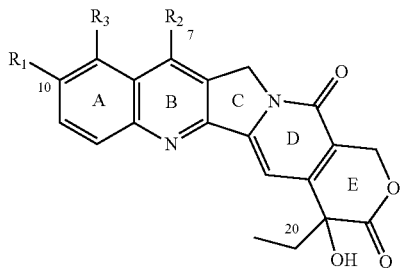

CPT: R1=R2=R3=H
10-hydroxy-CPT:R1=OH; R2=R3=H
Irinotecan (CPT-11)

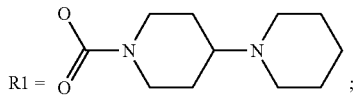

R2-ethyl; R3=H
SN-38: R1=OH; R2=ethyl; R3=H
Topotecan: R1=OH; R2=H; R3=CH—N(CH$_3$)$_2$ The term "intracellular metabolite" refers to a compound produced by intracellular metabolic processes or reactions of antibody-drug conjugates (ADCs). The metabolic process or reaction can be an enzymatic process, such as proteolytic cleavage of a peptide linker of an ADC, or hydrolysis of a functional group such as a hydrazone, ester or amide. Intracellular metabolites include, but are not limited to, antibodies and free drugs that undergo intracellular cleavage after entering, diffusing, ingesting or transporting into cells.

The terms "of intracellular cleavage" and "intracellular cleavage" refer to intracellular metabolic processes or reactions of antibody-drug conjugates (ADCs), wherein the covalent attachment between drug moiety (D) and antibody (Ab) is cleaved (i.e. the linker is cleaved), resulting in intracellular dissociation of free drug from the antibody. The module cleaved from ADC is thus an intracellular metabolite.

The term "bioavailability" refers to the systemic availability (i.e., blood/plasma level) of a given amount of drug administered to a patient. Bioavailability is an absolute term that indicates the time (rate) and the total amount (degree) required by the drug to achieve systemic circulation from the administered dose.

The term "cytotoxic activity" refers to cell killing, cytostatic, or growth inhibitory effects of intracellular metabolites of antibody-drug conjugates or antibody-drug conjugates. Cytotoxic activity can be expressed as the IC50 value, that is, the concentration (molar or mass) per unit volume when half of cells survive.

The term "alkyl" refers to a saturated aliphatic hydrocarbyl group, which is a linear or branched chain including $C_1$-$C_{20}$, preferably an alkyl having 1 to 12 carbon atoms, more preferably an alkyl having 1 to 10 carbon atoms, most preferably an alkyl having 1 to 6 carbon atoms. Representative examples include, but are not limited to, methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 2,2-diethylhexyl, and various branched isomers thereof. The alkyl group can be substituted or unsubstituted. When substituted, the substituent group(s) can substitute at any available connection point, and the substituent group(s) is preferably one or more groups independently selected from the group consisting of alkyl, alkenyl, alkynyl, alkyloxyl, alkylthiol, alkylamino, halogen, thiol, hydroxy, nitro, cyano, cycloalkyl, heterocyclic alkyl, aryl, heteroaryl, cycloalkoxy, heterocyclic alkoxy, cycloalkylthio, heterocycloalkylthio, and oxo.

The term "Cycloalkyl" refers to a saturated or partially unsaturated monocyclic or polycyclic hydrocarbyl group. Cycloalkyl has 3 to 20 carbon atoms, preferably 3 to 12 carbon atoms, more preferably 3 to 10 carbon atoms, most preferably 3 to 8 carbon atoms. Representative examples of monocyclic cycloalkyl include, but are not limited to, cyclopropyl, cyclobutyl, cyclopentyl, cyclopentenyl, cyclohexyl, cyclohexenyl, cyclohexadienyl, cycloheptyl, cycloheptatrienyl, cyclooctyl, etc. Polycyclic cycloalkyl includes cycloalkyl having a spiro ring, fused ring or bridged ring.

The term "Heterocyclyl" refers to a saturated or partially unsaturated monocyclic or polycyclic hydrocarbon substituent having 3 to 20 cyclic atoms, wherein one or more cyclic atoms are heteroatoms selected from the group consisting of N, O, and S(O). (wherein m is an integer between 0 and 2), but excluding —O—O—, —O—S— or —S—S— in the ring, and the remaining cyclic atoms are C atoms. 3 to 12 cyclic atoms are preferred, wherein 1 to 4 atoms are heteroatoms; 3 to 10 cyclic atoms are more preferred. Representative examples of monocyclic heterocyclyl include, but are not limited to, pyrrolidinyl, piperidyl, piperazinyl, morpholinyl, thiomorpholinyl, homopiperazinyl, and the like. Polycyclic heterocyclyl includes the heterocyclyl having a spiro ring, fused ring or bridged ring.

The ring of said heterocyclyl can be fused to the ring of an aryl, heteroaryl or cycloalkyl, wherein the ring bound to the parent structure is heterocyclyl. Representative examples include, but are not limited to the following groups:

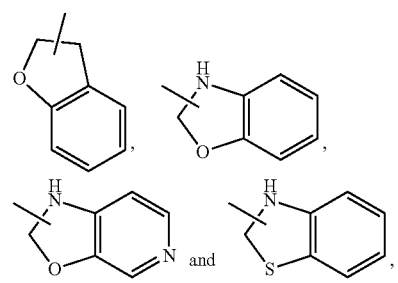

etc.

The heterocyclyl can be optionally substituted or unsubstituted. When substituted, the substituent group(s) is preferably one or more group(s) independently selected from the group consisting of alkyl, alkenyl, alkynyl, alkoxy, alkylsulfo, alkylamino, halogen, thiol, hydroxy, nitro, cyano, cycloalkyl, heterocyclic alkyl, aryl, heteroaryl, cycloalkoxy, heterocylic alkoxy, cycloalkylthio, heterocylic alkylthio, and oxo group.

The term "aryl" refers to a 6- to 14-membered all-carbon monocyclic ring or fused polycyclic ring (that is, the rings share the adjacent carbon atom pair), which has a conjugated π-electron system. The aryl is preferably 6- to 10-membered, such as phenyl and naphthyl, preferably phenyl. The aryl ring can be fused to the ring of a heteroaryl, heterocyclyl or cycloalkyl, wherein the ring bound to the parent structure is the ring of aryl. Representative examples include, but are not limited to, the following groups:

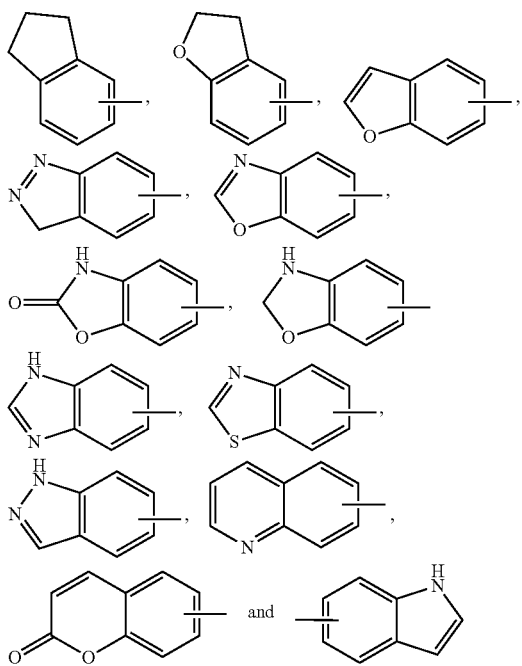

The aryl group can be substituted or unsubstituted. When substituted, the substituent group(s) is preferably one or more groups independently selected from the group consisting of alkyl, alkenyl, alkynyl, alkoxy, alkylthiol, alkylamino, halogen, thiol, hydroxy, nitro, cyano, cycloalkyl, heterocycloalkyl, aryl, heteroaryl, cycloalkoxy, heterocycloalkoxy, cycloalkylthio, and heterocycloalkylthio.

The term "heteroaryl" refers to a heteroaromatic system having 1 to 4 heteroatoms and 5 to 14 cyclic atoms, wherein the heteroatoms are selected from the group consisting of O, S, and N. The heteroaryl is preferably 5- to 10-membered, more preferably 5- or 6-membered, such as furyl, thienyl, pyridinyl, pyrrolyl, N-alkyl pyrrolyl, pyrimidinyl, pyrazinyl, imidazolyl, tetrazolyl, and the like. The ring of heteroaryl can be fused with the ring of an aryl, heterocyclyl or cycloalkyl, wherein the ring bound to the parent structure is the ring of heteroaryl. Representative examples include, but are not limited to, the following groups:

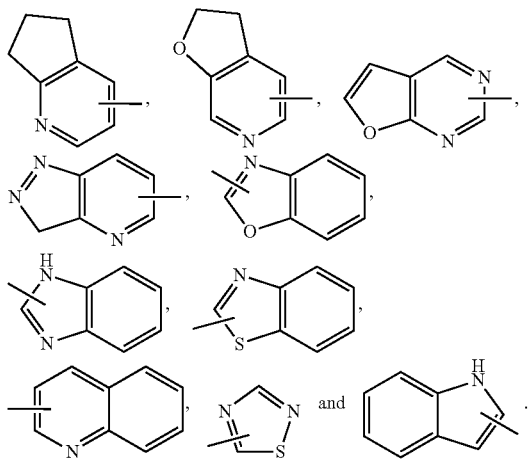

The heteroaryl group can be optionally substituted or unsubstituted. When substituted, the substituent group(s) is preferably one or more groups independently selected from the group consisting of alkyl, alkenyl, alkynyl, alkoxy, alkylthiol, alkylamino, halogen, thiol, hydroxy, nitro, cyano, cycloalkyl, heterocycloalkyl, aryl, heteroaryl, cycloalkoxy, heterocycloalkoxy, cycloalkylthio, and heterocycloalkylthio.

The term "alkoxy" refers to both an —O-(alkyl) and an —O-(unsubstituted cycloalkyl) group, wherein the alkyl is as defined above. Representative examples of alkoxy include, but are not limited to, methoxy, ethoxy, propoxy, butoxy, cyclopropyloxy, cyclobutyloxy, cyclopentyloxy, and cyclohexyloxy. The alkoxy can be optionally substituted or unsubstituted. When substituted, the substituent is preferably one or more groups independently selected from the group consisting of alkyl, alkenyl, alkynyl, alkoxy, alkylsulfo, alkylamino, halogen, thiol, hydroxy, nitro, cyano, cycloalkyl, heterocycloalkyl, aryl, heteroaryl, cycloalkoxy, heterocyclic alkoxy, cycloalkylthio, and heterocyclic alkylthio.

The term "bond" refers to a covalent bond presented as "-."

The term "Hydroxy" refers to an —OH group.

The term "Halogen" refers to fluoro, chloro, bromo or iodo atoms.

The term "Amino" refers to an —NH$_2$ group.

The term "Cyano" refers to a —CN group.

The term "Nitro" refers to a —NO$_2$ group.

The term "Oxo group" refers to a=O group.

The term "optional" or "optionally" means that the event or circumstance described subsequently can but does not necessarily occur, and the description includes the instances in which the event or circumstance does or does not occur. For example, "the heterocyclic group optionally substituted with an alkyl" means that an alkyl group can be, but is not necessarily, present, and the description includes a case wherein the heterocyclic group is substituted with an alkyl and a case wherein the heterocyclic group is not substituted with an alkyl.

"Substituted" refers to one or more hydrogen atoms in the group, preferably up to 5, more preferably 1 to 3 hydrogen atoms, each independently substituted with the corresponding number of substituents. It is clear that the substituents only exist in their possible chemical position. The person skilled in the art is able to determine if the substitution is possible or impossible without paying excessive efforts by experiment or theory. For example, the conjugation between amino or hydroxy group having free hydrogen and carbon atoms having unsaturated bonds (such as alkene) may be unstable.

"Linker" refers to a chemical module comprising a covalent or atomic chain that covalently attaches the antibody to the drug module. In various embodiments, the linker includes: divalent radicals such as alkyldiyl, arylene, heteroarylene, such as unit like —(CR2)nO(CR2)n-, hydrocarbyloxy repeat units (e.g., polyethyleneamino, PEG, polymethyleneoxy) and aminoalkyl (e.g., polyvinylamino, Jeffamine™), and so on; and diesters and amides including succinic acid esters, succinamides, bis Glycolate, malonate and caproamide.

Abbreviations

Linker Units:
MC=6-maleimido-caproyl

Val-Cit or "vc"=Valine-citrulline (an exemplary dipeptide of a protease cleavable linker)

Citrulline=2-Amino-5-ureido pentanoic acid

PAB=P-aminobenzyloxycarbonyl (examples of "self-immolative" linker unit)

Me-Val-Cit=N-Methyl-valine-citrulline (wherein the linker peptide bond has been modified to prevent its cleavage by cathepsin B)

MC(PEG)6-OH=maleimido-caproyl-polyethylene glycol (which can be attached to antibody cysteine)

SPP=N-Succinimidyl 4-(2-pyridylthio) valerate

SPDP=N-Succinimidyl 3-(2-pyridyldithio) propionate

SMCC=Succinimidyl-4-(N-maleimidomethyl) cyclohexane-1-carboxylate

IT=imino sulfane

Cytotoxic Drugs:

MMAE=Monomethyl aurantatin E (MW 718)

MMAF=variant of aurantatin E (MMAE), which has phenylalanine at the C-terminus of the drug (MW731.5)

MMAF-DMAEA=DMAEA (dimethylaminoethylamine) linked to the phenylalanine at C-terminal of MMAF(MW 801.5) by amide MMAF-TEG=phenylalanine of MMAF is esterified by tetraethylene glycol MMAF-NtBu=N-tert-butyl as an amide attached to the C-terminus of the MMAF DM1=N(2')-deacetyl-N(2')-(3-mercapto-1-oxopropyl)-maytian DM3=N(2')-deacetyl-N2-(4-mercapto-1-oxopentyl)-maytian DM4=N(2')-deacetyl-N2-(4-mercapto-4-methyl-1-oxopentyl)-maytian The present invention also provides an antibody-cytotoxic drug conjugate comprising any anti-c-Met antibody of the invention or other c-Met antibody showing endocytosis activity (eg, LY-2875358) conjugated to one or more cytotoxic agents, or a pharmaceutically acceptable salt or solvate compound thereof (interchangeable as "antibody-drug conjugate" or "ADC"), wherein the cytotoxic agents include examples of chemotherapeutic agents, drugs, growth inhibitors, toxins (e.g., bacterial, fungal, plant or animal-derived enzyme-active toxins or fragments thereof) or radioisotopes (i.e., radioluminescent conjugates).

In certain embodiments, the antibody-cytotoxic drug conjugate or a pharmaceutically acceptable salt or solvate compound thereof comprises an anti-c-Met antibody and a chemotherapeutic agent or other toxin. A chemotherapeutic agent that can be used to produce an antibody-cytotoxic drug conjugate or a pharmaceutically acceptable salt or solvate compound thereof has been described herein. Enzyme-active toxins and fragments thereof are also used, which are described herein.

In certain embodiments, the antibody-cytotoxic drug conjugate or a pharmaceutically acceptable salt or solvate compound thereof comprises an anti-c-Met antibody and one or more small molecule toxins including, but not limited to small molecule drugs such as camptothecin derivatives, calicheamicin, maytansinoids, dolastatin, oricotine, trichothecene and CC1065, and cytotoxic fragments of these drugs.

Exemplary L$_2$ linkers include 6-maleimidocaproyl ("MC"), maleimidopropionyl ("MP"), valine-citrulline ("val-cit" or "vc"), alanine-phenylalanine (ala-phe), p-aminobenzyloxycarbonyl ("PAB"), N-succinimidyl 4-(2-pyridylthio) pentanoate "SPP"), N-succinimidyl 4-(N-maleimidomethyl) cyclohexane-1 carboxylate ("SMCC"), and N-succinimidyl (4-iodo-acetyl) aminobenzoate ("SIAB"). A variety of linkers are known in the art and are described below.

The linker can be a "cleavable linker" that facilitates the release of the drug in the cell. For example, an acid labile linker (e.g., hydrazone), a protease-sensitive (e.g., peptidase-sensitive) linker, a light-labile linker, a dimethyl linker, or a disulfide-containing linker (Chari et al, Cancer Research 52: 127-131 (1992); U.S. Pat. No. 5,208,020).

In some embodiments, the linker can be a "stretcher unit" that connects the antibody to another linker or drug module. Exemplary stretcher units are shown below (where the wavy line indicates the site to which the antibody is covalently attached):

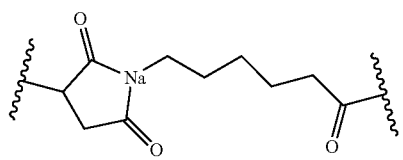
MC

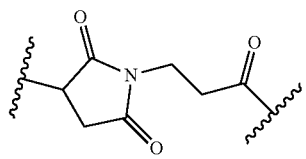
MP

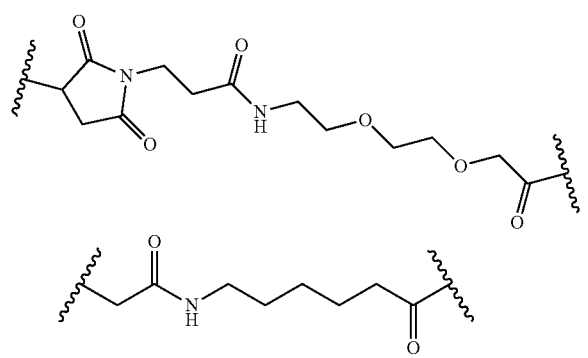
MPEG

In some embodiments, the linker unit can be an amino acid unit. In one such embodiment, the amino acid unit allows the protease to cleave the linker, thereby facilitating release of the drug from the antibody-cytotoxic drug conjugate or its pharmaceutically acceptable salt or solvate compound thereof after exposure to intracellular proteases, such as lysosomal enzymes. See the example in Doronina et al (2003) Nat. Biotechnol. 21: 778-784. Exemplary amino acid units include, but are not limited to, dipeptides, tripeptides, tetrapeptides, and pentapeptides. Exemplary dipeptides include: valine-citrulline (VC or val-cit); alanine-phenylalanine (AF or ala-phe); phenylalanine-lysine (FK or phe-lys); or N-Methyl-valine-citrulline (Me-val-cit). Exemplary tripeptides include glycine-valine-citrulline (gly-val-cit) and glycine-glycine-glycine (gly-gly-gly). The amino acid units can comprise naturally occurring amino acid residues, as well as minor amino acids and non-naturally occurring amino acid analogs, such as citrulline. Amino acid units can be designed and optimized for their selectivity to enzymatic cleavage of specific enzymes, such as tumor-associated proteases, cathepsin B, C or D, or plasma proteases.

In some embodiments, the linker can be a "spacer" unit that connects the antibody (either directly or through the extension unit and/or the amino acid unit) to the drug module. The spacer unit can be "self-immolative" or "non-self immolative". The "non-self immolative" spacer unit refers to a portion or the whole of the spacer unit that remains the spacer unit bound to the drug module after enzymatic (protein hydrolysis) cleavage of the ADC. Examples of non-self immolative spacer units include, but are not limited to, glycine spacer units and glycine-glycine spacer units. Other combinations of peptide spacers susceptible to sequence-specific enzymatic cleavage are also contemplated. For example, enzymatic cleavage of glycine-glycine spacer unit-containing ADC by tumor-cell-associated protease will result in the release of the glycine-glycine-drug module from the remainder of the ADC. In one such embodiment, the glycine-glycine-drug module is then subjected to a separate hydrolysis step in the tumor cells, thereby cleaving the glycine-glycine spacer unit from the drug module.

The "self-immolative" spacer unit allows the release of the drug module without separate hydrolysis steps. In certain embodiments, the spacer unit of the linker comprises a p-aminobenzyl unit. In one such embodiment, p-aminobenzyl alcohol is attached to the amino acid unit via an amide bond, thereby forming a carbamate, methyl carbamate, or carbonate between benzyl alcohol and the cytotoxic agent. See, for example, in Hamann et al, (2005) Expert Opin. Ther. Patents (2005) 15: 1087-1103. In one embodiment, the spacer units are p-aminobenzyloxycarbonyl (PAB).

Exemplary linker unit in the present invention are as follows:

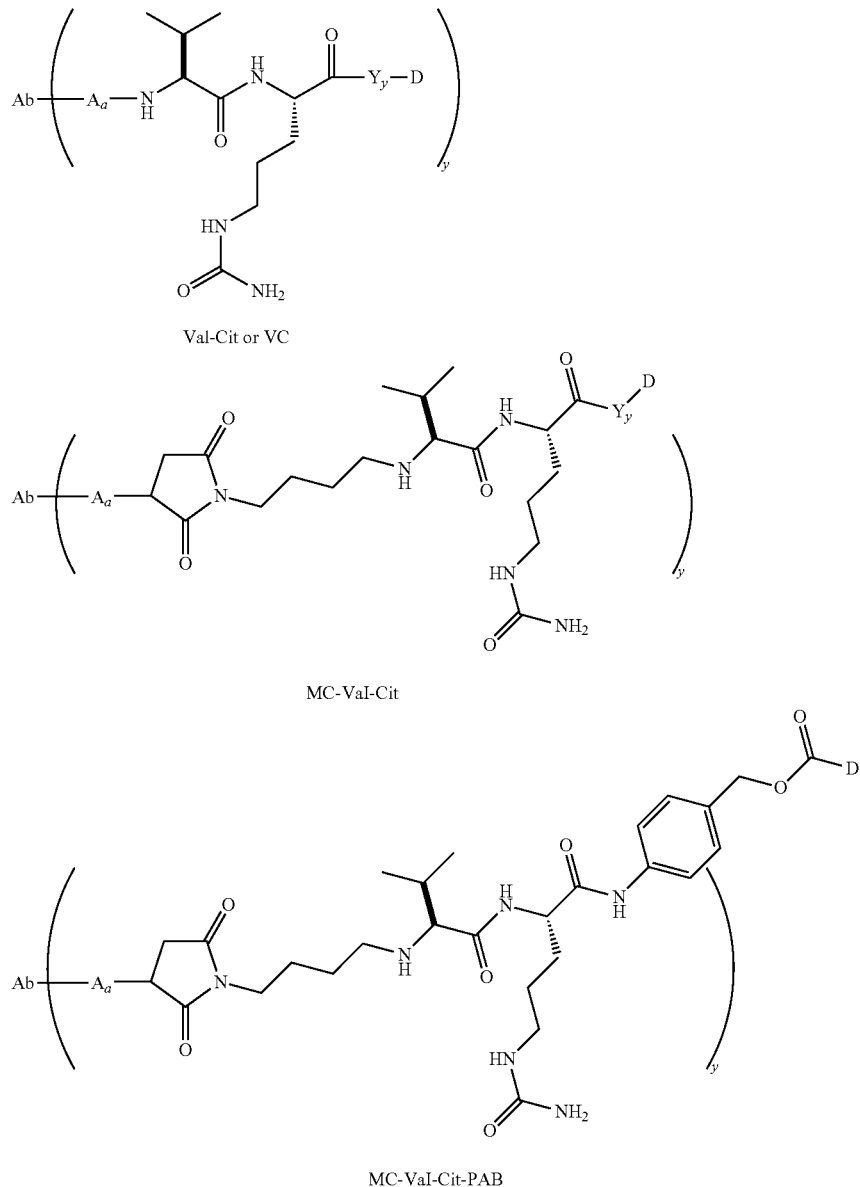

The linker, including the extension, the spacer, and the amino acid unit, can be synthesized by methods known in the art, such as those described in US 2005-0238649 A1.

Exemplary Drug Modules:
Maytansine and Maytansinoid Alkaloids

In some embodiments, the antibody-cytotoxic drug conjugate or a pharmaceutically acceptable salt or solvate compound thereof comprises an antibody of the invention conjugated to one or more maytansinoid molecules. The maytansinoid is a mitotic inhibitor that acts by inhibiting tubulin multimerization. Maytansine was originally isolated from the Maytian tree (*Maytenus serrata*) from the East African shrubs (U.S. Pat. No. 3,896,111). It was subsequently found that certain microorganisms also generate maytansinoid alkaloids such as maytansinol and C-3 adefovir (U.S. Pat. No. 4,151,042).

The maytansinoid drug modules are attractive drug modules in antibody-drug conjugates because they are: (i) relatively easy to be chemically modified or derivatized from fermentation or fermentation products; (ii) readily derivatized with a functional group suitable for coupling to an antibody through a non-disulfide linker; (iii) stable in plasma; and (iv) effective for a variety of tumor cell lines.

Maytansine compounds suitable for use as the maytansinoid alkaloid drug modules are well known in the art and can be isolated from natural sources according to known methods or produced using genetic engineering techniques (See Yu et al (2002) PNAS 99: 7968-7973). The maytansinol and maytansinol analogs can also be prepared according to known methods.

Exemplary embodiments of the maytansinoid alkaloid drug module include: DM1, DM3 and DM4, as disclosed herein.

Auristatin and Dolastatin

In some embodiments, the antibody-cytotoxic drug conjugate or a pharmaceutically acceptable salt or solvate compound thereof comprises an antibody of the invention conjugated to dolastatin or dolastatin peptide analogue or derivative (e.g., auristatin) (U.S. Pat. Nos. 5,635,483; 5,780,588). Dolastatin and auristatin have been shown to interfere with microtubule kinetics, GTP hydrolysis, and nuclear and cell division (Woyke et al. (2001) Antimicrob. Agents and Chemother. 45 (12): 3580-3584), and to have anti-cancer activity (U.S. Pat. No. 5,663,149) and antifungal activity (Pettit et al. (1998) Antimicrob. Agents Chemother. 42: 2961-2965). Dolastatin or auristatin drug modules may be attached to the antibody via the N (amino) terminus or the C (carboxy) terminus of the peptide drug module (WO02/088172).

Exemplary administration regimens of auristatin include N-terminal linked monomethyl auristatin drug modules DE and DF, which are disclosed by Senter et al, Proceedings of the American Association for CancerResearch, volume 45, abstract number 623, Mar. 28, 2004, the disclosure of which is expressly incorporated herein by reference in its entirety. The peptide drug module can be selected from the general formulas $D_E$ and $D_F$ as below:

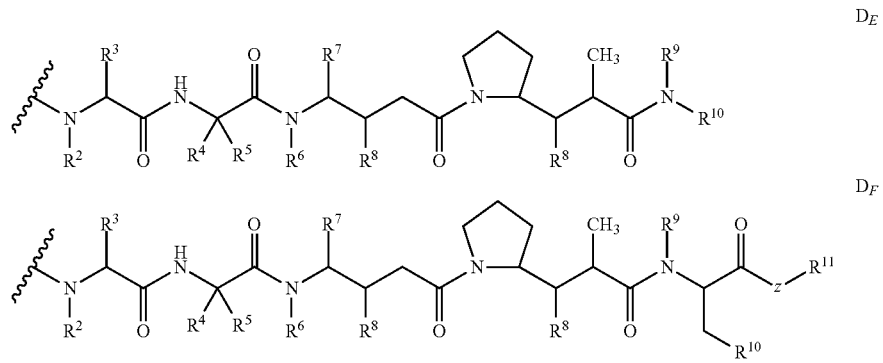

wherein the wavy lines of the $D_E$ and $D_F$ indicate the covalent attachment sites of the antibody or antibody-linker, and each site is independent from one another:

$R^2$ is selected from H and C1-C8 hydrocarbyl;

$R^3$ is selected from the group consisting of H, C1-C8 hydrocarbyl, C3-C8 carbocycle, aryl, C1-C8 hydrocarbyl-aryl, C1-C8 hydrocarbyl-(C3-C8 carbocycle), C3-C8 heterocycle and C1-C8 hydrocarbyl-(C3-C8 heterocycle);

$R^4$ is selected from the group consisting of H, C1-C8 hydrocarbyl, C3-C8 carbocycle, aryl, C1-C8 hydrocarbyl-aryl, C1-C8 hydrocarbyl-(C3-C8 carbocycle), C3-C8 heterocycle and C1-C8 hydrocarbyl-(C3-C8 heterocycle);

$R^5$ is selected from H and methyl;

or $R^4$ and $R^5$ form a carbocycle of formula —(CRaRb)n-, wherein $R^a$ and $R^b$ are each independently selected from the group consisting of H, C1-C8 hydrocarbyl and C3-C8 carbocycle, and n is selected from 2, 3, 4, 5 and 6;

$R^6$ is selected from H and C1-C8 hydrocarbyl;

$R^7$ is selected from the group consisting of H, C1-C8 hydrocarbyl, C3-C8 carbocycle, aryl, C1-C8 hydrocarbyl-aryl, C1-C8 hydrocarbyl-(C3-C8 carbocycle), C3-C8 heterocycle and C1-C8 hydrocarbyl-(C3-C8 heterocycle);

each R is independently selected from the group consisting of H, OH, C1-C8 hydrocarbyl, C3-C8 carbocycle and O—(C1-C8 hydrocarbyl);

$R^9$ is selected from H and C1-C8 hydrocarbyl;

$R^0$ is selected from aryl and C3-C8 heterocycle;

Z is selected from O, S, NH and $NR^{12}$—, wherein $R^{12}$ is C1-C8 hydrocarbyl;

$R^{11}$ is selected from the group consisting of H, C1-C20 hydrocarbyl, aryl, C3-C8 heterocycle, —$(R^{13}O)m-R^{14}$ and —$(R^{13}O)m-CH(R^{15})_2$;

m is an integer from 1-1000;

$R^{13}$ is C2-C8 hydrocarbyl;

$R^{14}$ is H or C1-C8 hydrocarbyl;

$R^{15}$ is each independently selected from the group consisting of H, COOH, —$(CH_2)n-N(R16)_2$, —$(CH_2)n-SO_3H$ and —$(CH_2)n-SO_3$—C1-C8 hydrocarbyl;

$R^{16}$ is each independently selected from the group consisting of H, C1-C8 hydrocarbyl and —$(CH_2)n-COOH$;

$R^{18}$ is selected from —$C(R8)_2-C(R8)_2$-aryl, —$C(R8)_2-C(R8)_2$-(C3-C8 heterocycle) and —$C(R8)_2-C(R8)_2$-(C3-C8 carbocycle); and n is an integer selected from 0 to 6.

An exemplary auristatin of the formula $D_E$ is MMAE, wherein the wavy line indicates a linker (L) covalently attached to the antibody-drug conjugate:

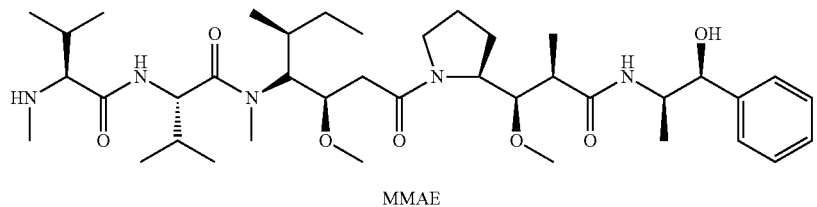

MMAE

An exemplary auristatin of the formula $D_F$ is MMAF, wherein the wavy line indicates a linker (L) covalently attached to the antibody-drug conjugate (see US2005/0238649 and Doronina et al (2006) Bioconjugate Chem. 17: 114-124):

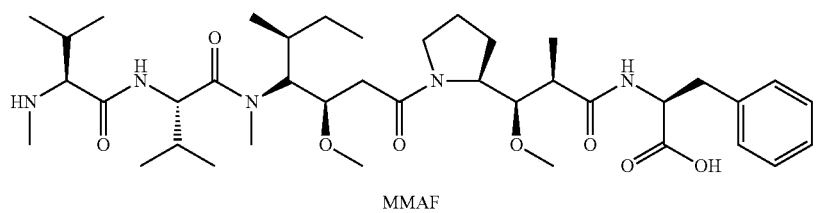

MMAF

The other drug modules comprise a MMAF derivative selected from the following, wherein the wavy line indicates a linker (L) covalently attached to the antibody-drug conjugate:

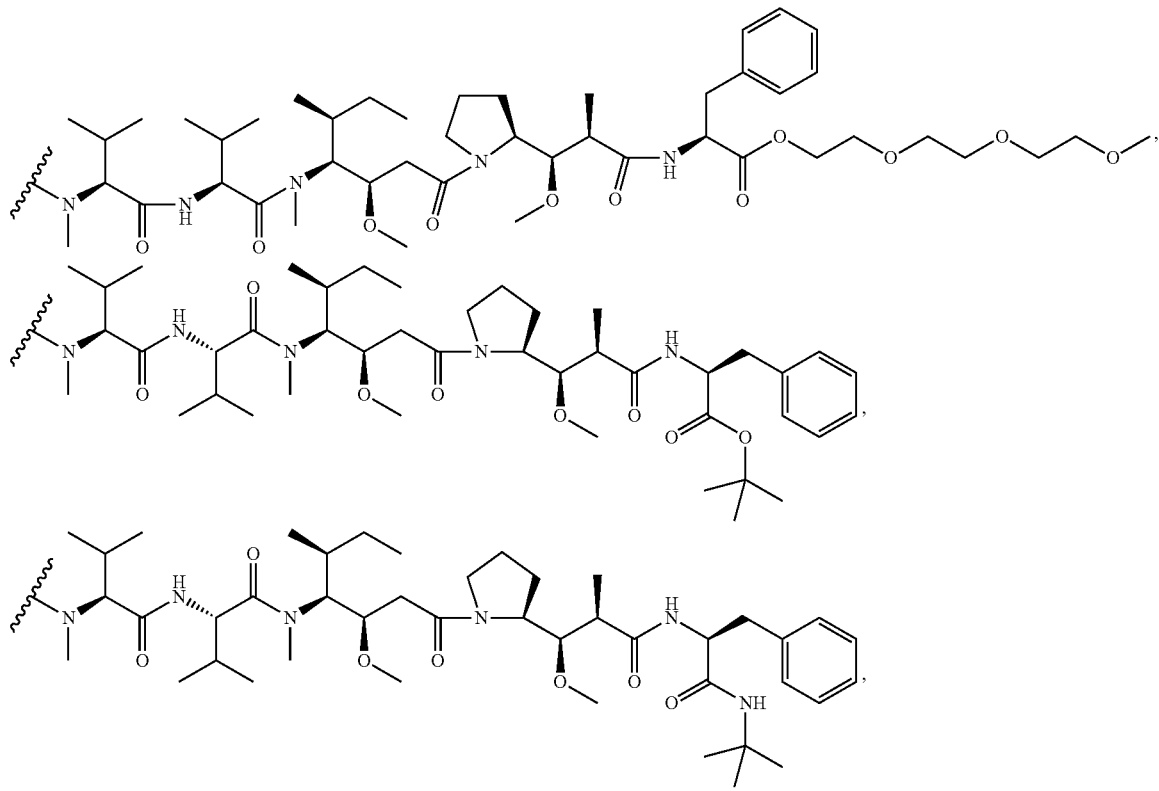

-continued
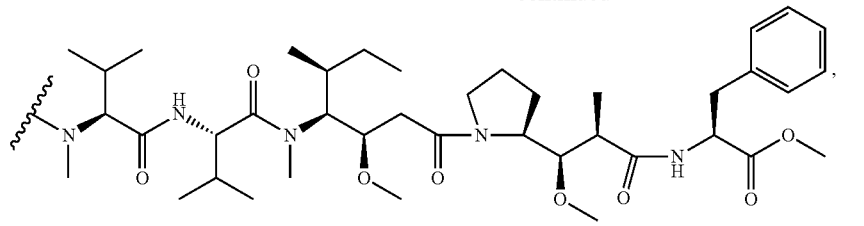
,
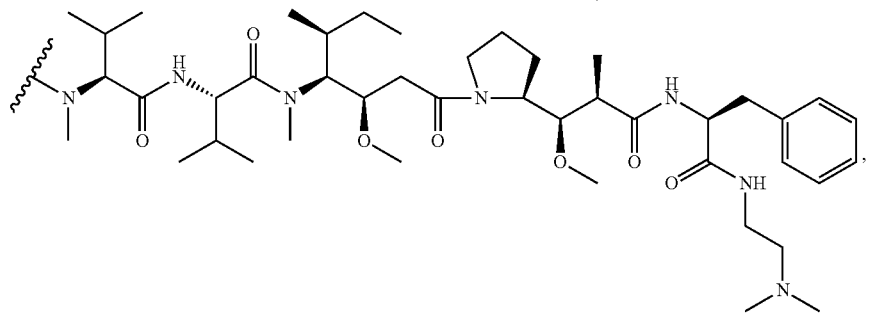
,
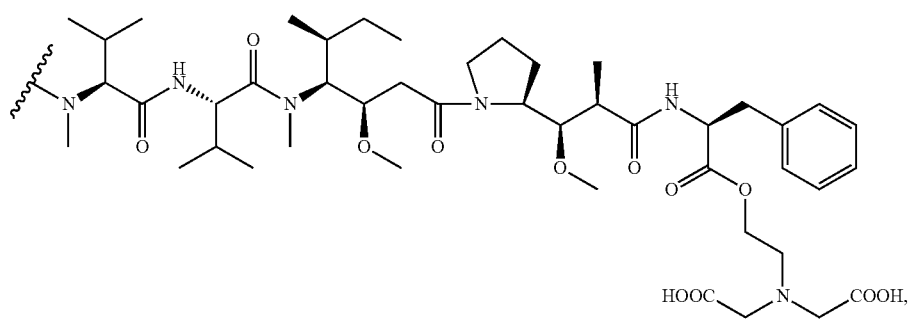
,
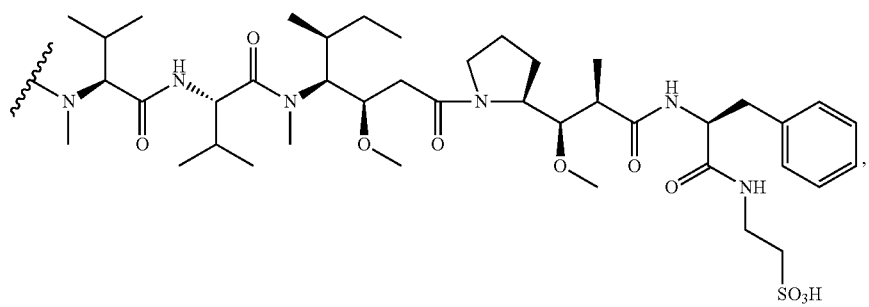
,
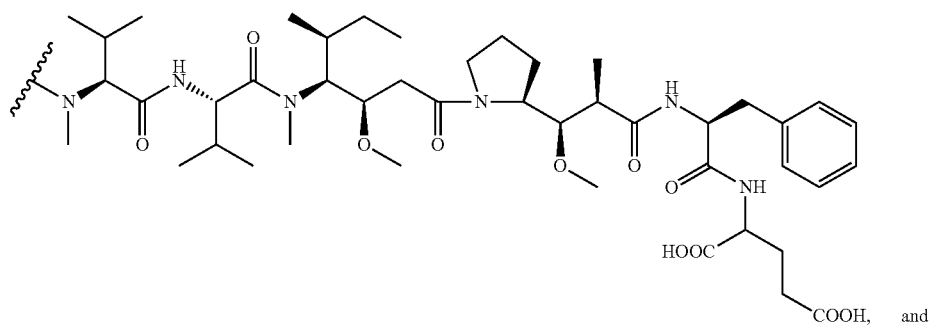
and

-continued

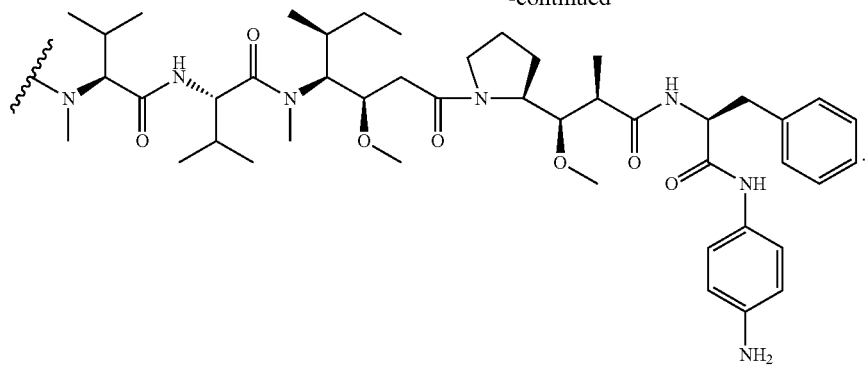

In one aspect, a hydrophilic group can be attached to a drug module at $R^{11}$, wherein said hydrophilic group includes, but is not limited to, triethylene glycol ester (TEG), as described above. Without being limited to any particular theory, the hydrophilic groups contribute to the internalization and non-agglomeration of the drug modules. Exemplary embodiments of ADC of general formula (I) that comprise auristatin/dolastatin or a derivative thereof are described in US2005-0238649A1 and Doronina et al (2006) Bioconjugate Chem. 17:114-124, which is expressly incorporated herein by reference. Exemplary embodiments of ADCs of general formula (I) comprising MMAE or MMAF and various linkers have the following structure and abbreviations (wherein "Ab" is antibody; p ranges from 1 to about 8; "Val-Cit" is Valine-citrulline dipeptide; and "S" is sulfur atom):

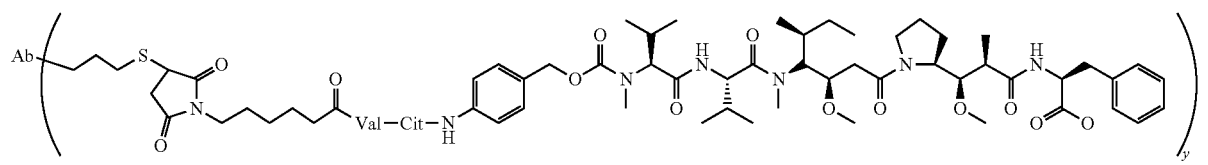

Ab-linker 1-MC-vc-PAB-MMAF

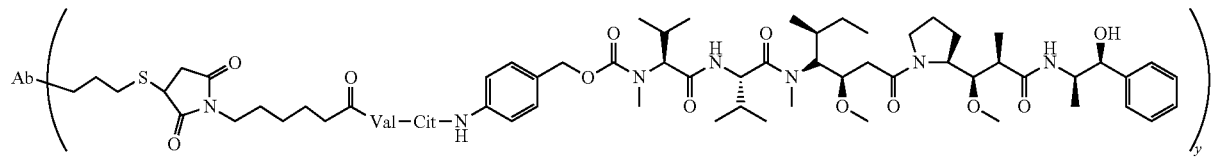

Ab-linker 1-MC-vc-PAB-MMAE

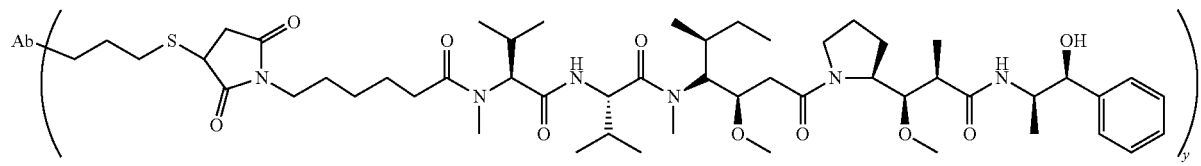

Ab-linker 1-MC-MMAE

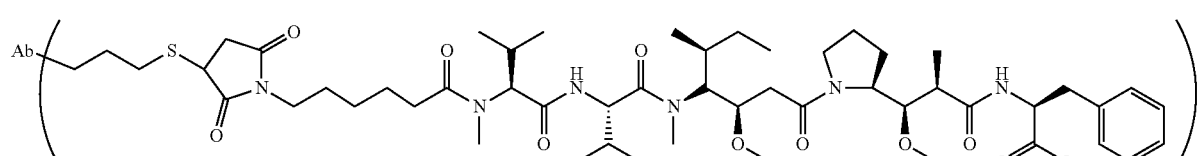

Ab-linker 1-MC-MMAF

Typically, peptide-based drug modules can be prepared by forming peptide bonds between two or more amino acids and/or peptide fragments. Such peptide bonds can be prepared according to, for example, liquid phase synthesis methods well known in the art of peptide chemistry (see E. Schroder and K. Lübke, The Peptides, volume 1, pp 76-136, 1965, Academic Press). The auristatin/dolastatin drug modules can be prepared according to the methods described in the following literatures: US2005-0238649A1; U.S. Pat. Nos. 5,635,483; 5,780,588; Pettit et al (1989) J. Am. Chem. Soc. 111: 5463-5465; Pettit et al (1998) Anti-Cancer Drug Design 13: 243-277; Pettit, G. R. et al, Synthesis, 1996, 719-725; Pettit et al (1996) J. Chem. Soc. Perkin Trans. 15: 859-863; and Doronina (2003) Nat. Biotechnol. 21(7): 778-784.

In particular, the auristatin/dolastatin drug modules of the general formula DF, such as MMAF and derivatives thereof, can be prepared using the methods described in US2005-0238649A1 and Doronina et al. (2006) Bioconjugate Chem. 17: 114-124. The auristatin/dolastatin drug modules of the general formula DE, such as MMAE and derivatives thereof, can be prepared by the method described in Doronina et al. (2003) Nat. Biotech. 21: 778-784. The drug-linker modules of MC-MMAF, MC-MMAE, MC-vc-PAB-MMAF and MC-vc-PAB-MMAE can be conveniently synthesized by conventional methods such as those described in Doronina et al. (2003) Nat. Biotech. 21: 778-784 and U.S. Patent Application Publication No. US2005/0238649A1, and then conjugated to the antibody of interest.

Drug Load

The drug load (loading) is represented by y in formula (I), that is, y represents the average number of drug modules per antibody in the molecule of formula (I). The drug load can range from 1 to 20 drug modules (D) per antibody. The ADC of Formula (I) includes a collection of antibodies conjugated to a range of (1-20) drug modules. The average number of drug modules per antibody in ADC preparation obtained from a coupling reaction can be characterized by conventional means such as mass spectrometry, ELISA assay, and HPLC. It is also possible to determine the quantitative distribution of ADCs with respect to y. In some cases, homogeneous ADCs with certain p values are isolated from ADCs of other drug loads, and then purified and characterized. This can be achieved by means such as reverse phase HPLC or electrophoresis.

For some antibody-drug conjugates, y can be limited by the number of attachment sites on the antibody. For example, if the cysteine thiol is attached, as in the above illustrative embodiment, the antibody can have only one or several cysteine thiol groups, or can have only one or more reactive thiol groups which can be attached to the linker. In certain embodiments, a higher drug load, such as y>5, may cause aggregation, insolubility, toxicity, or loss of cell permeability of certain antibody-drug conjugates. In certain embodiments, the drug load of the ADC of the invention ranges from 1 to about 8; from about 2 to about 6; from about 3 to about 5; from about 3 to about 4; from about 3.1 to about 3.9; from about 3.2 to about 3.8; about 3.2 to about 3.7; about 3.2 to about 3.6; about 3.3 to about 3.8; or about 3.3 to about 3.7. In fact, for some ADCs, it has been shown that the optimal ratio of each drug module to antibody can be less than 8 and can be from about 2 to about 5. See US2005-0238649A1 (its entire content is incorporated herein by reference).

In certain embodiments, less than the theoretical maximum number of drug modules are coupled to the antibody in the coupling reaction. The antibody can comprise, for example, a lysine residue that does not react with a drug-linker intermediate or a linker agent, as discussed below. Only the most reactive lysine groups can react with amine-reactive linker agents. In general, the antibody does not contain a number of free and reactive cysteine thiol groups, which can be linked to a drug module; in fact, most of the cysteine thiol groups in the antibody are present in the form of a disulfide bridge. In certain embodiments, the antibody can be reduced with a reducing agent such as dithiothreitol (DTT) or tricarbonyl ethyl phosphine (TCEP) under partially or completely reductive conditions to produce a reactive cysteine thiol group. In certain embodiments, the antibody is placed under denaturing conditions to expose a reactive nucleophilic group, such as lysine or cysteine.

The drug load (drug/antibody ratio, DAR) of the ADC can be controlled in different ways, for example by: (i) limiting the molar excess of the drug-linker intermediate or linker agent; (ii) limiting the time or temperature of the coupling reaction; (iii) limiting the modification of the cysteine thiol or restricting the reductive condition; (iv) engineered the amino acid sequence of the antibody by recombinant techniques, such that the number and location of cysteine residues are altered in order to control the number and/or position of the linker-drug attachment (such as the thioMab or the thioFab prepared as those described in the present invention and WO2006/034488 (incorporated herein by reference in its entirety)).

It is to be understood that if more than one nucleophilic group is reacted with a drug-linker intermediate or with a linker and subsequent drug module agents, the resulting product is an ADC compound mixture having one or more drug modules attached to a distribution of the antibody. The average number of drugs per antibody can be calculated from the mixture by ELISA assay which involves antibody-specific and drug-specific antibodies. The various ADC molecules in the mixture can be identified by mass spectrometry, and separated by HPLC, for example, by hydrophobic interaction chromatography. In certain embodiments, a homogeneous ADC with a single load value can be isolated from the coupling mixture by electrophoresis or chromatography.

Methods for Preparing Antibody-Cytotoxic Drug Conjugates or Pharmaceutically Acceptable Salts or Solvate Compounds Thereof The ADC of general formula (I) can be prepared by several routes using organic chemical reactions, conditions and agents known to those skilled in the art, including: (1) the nucleophilic group of the antibody reacts with the divalent linker agent via a covalent bond to form Ab-L, followed by reaction with the drug module D; and (2) the nucleophilic group of the drug module reacts with the divalent linker agent via a covalent bond to form D-L, followed by reaction with the nucleophilic group of the antibody. The exemplary method for preparing the ADC of Formula (I) via the latter route is described in US2005-0238649A1, which is expressly incorporated herein by reference.

Nucleophilic groups of antibodies include, but are not limited to: (i) an N-terminal amine group; (ii) a side chain amine group such as lysine; (iii) a side chain thiol group such as cysteine; and (iv) a hydroxyl or amino group of saccharide in the glycosylated antibody. Amines, thiols and hydroxyl groups are nucleophilic and are capable of reacting with the electrophilic groups on the linker module to form covalent bonds, and the linker agents include: (i) active esters such as NHS esters, HOBt esters, haloformates, and acid halides; (ii) hydrocarbyl and benzyl halides, such as haloacetamides; (iii) aldehydes, ketones, carboxyl groups and maleimide groups. Some antibodies have a reducible interchain disulfide, that is a cysteine bridge. The antibody can be completely or partially reduced by treatment with a reducing agent such as DTT (dithiothreitol) or tricarbonyl ethylphosphine (TCEP) to provide coupling reactivity with the linker. Each cysteine bridge will theoretically form two reactive thiol nucleophiles. Alternatively, the sulfhydryl group can be introduced into the antibody via modification of the lysine residue, for example by reacting the lysine residue with 2-imin sulfane (Traut reagent), resulting in the conversion of the amine to the thiol.

The antibody-drug conjugates of the present invention can also be produced by the reaction between an electrophilic group on an antibody (such as an aldehyde or a ketone carbonyl group) and a linker or a nucleophilic group on a drug. Useful nucleophilic groups on the linker include, but are not limited to: hydrazide, oxime, amino, hydrazine, thiosemicarbazone, hydrazine carboxylate and arylhydrazide. In one embodiment, the saccharide of the glycosylated antibody can be oxidized with, for example, a periodate oxidant to form an aldehyde or ketone group that can react with the amine group of the linker or drug module. The resulting imine Schiff base can form a stable linkage or can be reduced with, for example, a borohydride agent to form a stable amine linkage. In one embodiment, the reaction of the carbohydrate moiety of the glycosylated antibody with galactose oxidase or sodium metaperiodate can produce a carbonyl group (aldehyde group and keto group) in the antibody, which can be reacted with a suitable group on the drug (Hermanson, Bioconjugate Techniques). In another embodiment, an antibody comprising an N-terminal serine or threonine residue can react with sodium metaperiodate, resulting in the formation of an aldehyde at the first amino acid (Geoghegan and Stroh, (1992) Bioconjugate Chem. 3: 138-146; U.S. Pat. No. 5,362,852). Such aldehydes can react with the drug module or the linker nucleophile.

Nucleophilic groups on the drug module include, but are not limited to: amine, thiol, hydroxy, hydrazide, oxime, hydrazine, thiosemicarbazone, hydrazine carboxylate and arylhydrazide groups, which can react with the electrophilic groups on the linker module to form covalent bonds. And the linker agents include: (i) active esters such as NHS esters, HOBt esters, haloformates, and acid halides; (ii) hydrocarbyl and benzyl halides, such as haloacetamides; and (iii) aldehydes, ketones, carboxyl groups, and maleimide groups.

The compounds of the present invention clearly cover but are not limited to the ADC prepared by the following crosslinking agents: BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, sulfo-SMPB and SVSB (succinimidyl-(4-vinylsulfone) benzoate), which are commercially available (such as Pierce Biotechnology, Inc., Rockford, Ill., U.S.A, * refer to the 2003-2004 Application Manual and product catalog (2003-2004 Applications Handbook and Catalog) page 467-498).

Antibody-cytotoxic drug conjugates or their pharmaceutically acceptable salts or solvate compounds containing antibodies and cytotoxic agents can also be prepared using a variety of bifunctional protein coupling agents, such as N-succinimidyl 3-(2-pyridyldithio) propionate (SPDP), succinimidyl-4-(N-maleimidomethyl) cyclohexane-1-carboxylate (SMCC), aminosulfane (IT), imidates (such as dimethyl adipamide HCl), active esters (such as disuccinimidyl suberate), aldehydes (such as glutaraldehyde), bis azide compounds (such as bis (p-azidobenzoyl) hexamethylene diamine), bis diazo derivatives (such as bis (p-diazo benzoyl)-ethylenediamine), diisothiocyanate (such as toluene 2,6-Diisocyanate) and dual active fluorine compounds (such as 1,5-difluoro-2,4-dinitrobenzene). For example, ricin immunotoxins can be prepared as described in Vitetta et al., Science 238: 1098 (1987). The carbon-14 labeled 1-isothiocyanate benzyl-3-methyl diethylene triamine pentaacetic acid (MX-DTPA) is an exemplary chelating agent for coupling a radioactive nucleotide to an antibody. See WO 94/11026.

Alternatively, a fusion protein comprising an antibody and a cytotoxic agent can be prepared by, for example, recombinant techniques or peptide synthesis. The recombinant DNA molecule can comprise regions encoding the antibody and cytotoxic moiety of the conjugate respectively, either adjacent to each other or separated by a region encoding a linker peptide, wherein said linker peptide does not destroy the desired properties of the conjugate.

In yet another embodiment, the antibody can be conjugated to a "receptor"; (such as streptavidin) for pre-targeting the tumor, wherein the antibody-receptor conjugate is administered to a patient, followed by the use of a scavenger which removes the unbound conjugates from circulation. Then, a "ligand" (e.g., avidin) coupled to a cytotoxic agent (such as a radioactive nucleotide) is administrated.

The following examples are provided for illustrative purposes only and are not intended to limit the scope of the invention.

DETAILED DESCRIPTION OF THE INVENTION

Hereinafter, the present invention is further described with reference to examples. However, the scope of the present invention is not limited thereto.

In the examples of the present invention, where specific conditions are not described, the experiments are generally conducted under conventional conditions, or under conditions proposed by the manufacturers of material or product. See Sambrook et al., Molecular Cloning, A Laboratory Manual, Cold Spring Harbor Laboratory; Current Protocols in Molecular Biology, Ausubel et al, Greene Publishing Associates, Wiley Interscience, NY. Where the source of the agents is not specifically given, the agents are commercially available.

EXAMPLE

Example 1. Antigenic Antibody Clonal Expression

The antibodies (light and heavy chains) and antigens used in the present invention are constructed by overlapping extension PCR methods known in the art. The DNA fragment obtained by overlapping extension PCR was inserted into the expression vector pEE6.4 (Lonza Biologics) using HindIII/BstBI, and expressed in 293F cells (Invitrogen, Cat # R790-07). The resulting recombinant protein is used for immunization or screening. The c-Met gene template is derived from origene Corporation (article number RC217003). The DNA sequence cloned and expressed is as follows.

Human c-Met extracellular region (ECD) and murine Fc region fusion protein (human c-Met ECD-mFc) DNA sequence:

(SEQ ID NO: 1)
atgaaggccccgctgtgcttgcacctggcatcctcgtgctcctgtttac cttggtgcagaggagcaatggggagtgtaaagaggcactagcaaagtccg agatgaatgtgaatatgaagtatcagcttcccaacttcaccgcggaaaca cccatccagaatgtcattctacatgagcatcacattttccttggtgccac taactacatttatgttttaaatgaggaagaccttcagaaggttgctgagt acaagactgggcctgtgctggaacacccagattgtttcccatgtcaggac tgcagcagcaaagccaatttatcaggaggtgtttggaaagataacatcaa catggctctagttgtcgacacctactatgatgatcaactcattagctgtg gcagcgtcaacagagggacctgccagcgacatgtctttccccacaatcat actgctgacatacagtcggaggttcactgcatattctccccacagataga agagcccagccagtgtcctgactgtgtggtgagcgccctgggagccaaag tcctttcatctgtaaaggaccggttcatcaacttctttgtaggcaatacc ataaattcttcttatttcccagatcatccattgcattcgatatcagtgag aaggctaaaggaaacgaaagatggttttatgttttgacggaccagtcct acattgatgttttacctgagttcagagattcttaccccattaagtatgtc catgcctttgaaagcaacaattttatttacttcttgacggtccaaaggga aactctagatgctcagacttttcacacaagaataatcaggttctgttcca taaactctggattgcattcctacatggaaatgcctctggagtgtattctc acagaaaagagaaaaaagagatccacaaagaaggaagtgtttaatatact tcaggctgcgtatgtcagcaagcctggggcccagcttgctagacaaatag gagccagcctgaatgatgacattcttttcggggtgttcgcacaaagcaag ccagattctgccgaaccaatggatcgatctgccatgtgtgcattccctat caaatatgtcaacgacttatcaacaagatcgtcaacaaaaacaatgtgag atgtctccagcattttacggacccaatcatgagcactgctttaatagga cacttctgagaaattcatcaggctgtgaagcgcgccgtgatgaatatcga acagagtttaccacagctttgcagcgcgttgacttattcatgggtcaatt cagcgaagtcctcttaacatctatatccaccttcattaaaggagacctca ccatagctaatcttgggacatcagagggtcgcttcatgcaggttgtggtt tctcgatcaggaccatcaaccctcatgtgaattttctcctggactccca tccagtgtctccagaagtgattgtggagcatacattaaaccaaatggct acacactggttatcactgggaagaagatcacgaagatcccattgaatggc ttgggctgcagacatttccagtcctgcagtcaatgcctctctgccccacc ctttgttcagtgtggctggtgccacgacaaatgtgtgcgatcggaggaat gcctgagcgggacatggactcaacagatctgtctgcctgcaatctacaag gttttccccaaatagtgcacccttgaaggagggacaaggctgaccatatg tggctgggactttggatttcggaggaataataaatttgatttaaagaaaa ctagagttctccttggaaatgagagctgcaccttgactttaagtgagagc acgatgaatacattgaaatgcacagttggtcctgccatgaataagcattt caatatgtccataattatttcaaatggccacgggacaacacaatacagta cattctcctatgtggatcctgtaataacaagtatttcgccgaaatacggt cctatggctggtggcactttacttactttaactggaaattacctaaacag tgggaattctagacacatttcaattggtggaaaaacatgtacttaaaaa gtgtgtcaaacagtattcttgaatgttatacccccagcccaaaccatttca actgagtttgctgttaaattgaaaattgacttagccaaccgagagacaag catcttcagttaccgtgaagatcccattgtctatgaaattcatccaacca aatctttattagtggtgggagcacaataacaggtgttgggaaaaacctg aattcagttagtgtcccgagaatggtcataaatgtgcatgaagcaggaag gaacttacagtggcatgtcaacatcgctctaattcagagataatctgtt gtaccactccttccctgcaacagctgaatctgcaactcccctgaaaacc aaagccttttcatgttagatgggatccttccaaatactttgatctcat ttatgtacataatcctgtgttaagccttttgaaaagccagtgatgatct caatgggcaatgaaaatgtactggaaattaagggaaatgatattgaccct gaagcagttaaggtgaagtgttaaaagttggaaataagagctgtgagaa tatacacttacattctgaagccgttttatgcacggtccccaatgacctgc tgaaattgaacagcgagctaaatatagagtggaagcaagcaatttcttca accgtccttggaaaagtaatagttcaaccagatcagaatttcaca Human c-Met Extracellular Sema Region and Flag-His Tag (Human c-Met Sema-Flis) DNA Sequence:

(SEQ ID NO: 2)
atgaaggccccgctgtgcttgcacctggcatcctcgtgctcctgtttac cttggtgcagaggagcaatggggagtgtaaagaggcactagcaaagtccg agatgaatgtgaatatgaagtatcagcttcccaacttcaccgcggaaaca cccatccagaatgtcattctacatgagcatcacattttccttggtgccac taactacatttatgttttaaatgaggaagaccttcagaaggttgctgagt acaagactgggcctgtgctggaacacccagattgatcccatgtcaggact gcagcagcaaagccaatttatcaggaggtgtttggaaagataacatcaac atggctctagttgtcgacacctactatgatgatcaactcattagctgtgg cagcgtcaacagagggacctgccagcgacatgtctttccccacaatcata ctgctgacatacagtcggaggttcactgcatattctccccacagatagaa gagcccagccagtgtcctgactgtgtggtgagcgccctgggagccaaagt cctttcatctgtaaaggaccggttcatcaacttattgtaggcaataccat aaatatcttatttcccagatcatccattgcattcgatatcagtgagaag gctaaaggaaacgaaagatggttttatgttttgacggaccagtcctaca ttgatgttttacctgagttcagagattcttaccccattaagtatgtccat gcctttgaaagcaacaattttatttacttcttgacggtccaaagggaaac tctagatgctcagacttttcacacaagaataatcaggttctgttccataa actctggattgcattcctacatggaaatgcctctggagtgtattctcaca gaaaagagaaaaaagagatccacaaagaaggaagtgtttaatatacttca ggctgcgtatgtcagcaagcctggggcccagcttgctagacaaataggag ccagcctgaatgatgacatttattcggggtgttcgcacaaagcaagccag attctgccgaaccaatggatcgatctgccatgtgtgcattccctatcaaa

```
tatgtcaacgacttcttcaacaagatcgtcaacaaaaacaatgtgagatg tctccagcattttttacggacccaatcatgagcactgctttaataggacac ttctgagaaattcatcaggctgtgaagcgcgccgtgatgaatatcgaaca gagtttaccacagctttgcagcgcgttgacttattcatgggtcaattcag cgaagtcctcttaacatctatatccaccttcattaaaggagacctcacca tagctaatcttgggacatcagagggtcgcttcatgcaggttgtggtttct cgatcaggaccatcaacccctcatgtgaattttctcctggactcccatcc agtgtctccagaagtgattgtggagcatacattaaaccaaaatggctaca cactggttatcactgggaagaagatcacgaagatcccattgaatggcttg ggctgcagacatttccagtcctgcagtcaatgcctctctgcccaccctt tgttcagtgtggctggtgccacgacaaatgtgtgcgatcggaggaatgcc tgagcgggacatggactcaacagatctgtctgcctgcaatctacaaggac tacaaggacgacgacaagcatgtccaccatcatcaccatcactgatt cgaa
```

Human c-Met ECD His Tag (Human c-Met ECD-his) Recombinant Protein DNA Sequence:

```
                                        (SEQ ID NO: 3)
atgaaggcccccgctgtgcttgcacctggcatcctcgtgctcctgtttac cttggtgcagaggagcaatggggagtgtaaagaggcactagcaaagtccg agatgaatgtgaatatgaagtatcagcttcccaacttcaccgcggaaaca cccatccagaatgtcattctacatgagcatcacattttcatggtgccact aactacatttatgttttaaatgaggaagaccttcagaaggttgctgagta caagactgggcctgtgctgaacacccagattgtttcccatgtcaggact gcagcagcaaagccaatttatcaggaggtgtttggaaagataacatcaac atggctctagttgtcgacacctactatgatgatcaactcattagctgtgg cagcgtcaacagagggacctgccagcgacatgtattcccacaatcatac tgctgacatacagtcggaggttcactgcatattctccccacagatagaag agcccagccagtgtcctgactgtgtggtgagcgccctgggagccaaagtc ctttcatctgtaaaggaccggttcatcaacttctttgtaggcaataccat aaattcttcttatttcccagatcatccattgcattcgatatcagtgagaa ggctaaaggaaacgaaagatggttaatgttttttgacggaccagtcctaca ttgatgttttacctgagttcagagattatacccccattaagtatgtccatg cctttgaaagcaacaattttatttacttcttgacggtccaaagggaaact ctagatgctcagacttttcacacaagaataatcaggttctgttccataaa ctctggattgcattcctacatggaaatgcctctgagtgtattctcacag aaaagagaaaaaagagatccacaaagaaggaagtgtttaatatacttcag gctgcgtatgtcagcaagcctggggcccagcttgctagacaaataggagc cagcctgaatgatgacattctttttcggggtgacgcacaaagcaagccaga ttctgccgaaccaatggatcgatctgccatgtgtgcattccctatcaaat atgtcaacgacttcttcaacaagatcgtcaacaaaaacaatgtgagatgt ctccagcattttttacggacccaatcatgagcactgctttaataggacact tctgagaaattcatcaggctgtgaagcgcgccgtgatgaatatcgaacag agtttaccacagattgcagcgcgttgacttattcatgggtcaattcagcg aagtcctcttaacatctatatccaccttcattaaaggagacctcaccata gctaatcttgggacatcagagggtcgcttcatgcaggttgtggtttctcg atcaggaccatcaacccctcatgtgaattttctcctggactcccatccag tgtctccagaagtgattgtggagcatacattaaaccaaaatggctacaca ctggttatcactgggaagaagatcacgaagatcccattgaatggcttggg ctgcagacatttccagtcctgcagtcaatgcctctctgcccaccattgt tcagtgtggctggtgccacgacaaatgtgtgcgatcggaggaatgcctga gcgggacatggactcaacagatctgtctgcctgcaatctacaaggttttc ccaaatagtgcacccctttgaaggagggacaaggctgaccatatgtggctg ggactttggatttcggaggaataataaatttgattttaaagaaaactagag ttctccttggaaatgagagctgcaccttgactttaagtgagagcacgatg aatacattgaaatgcacagttggtcctgccatgaataagcatttcaatat gtccataattatttcaaatggccacgggacaacacaatacagtacattct cctatgtggatcctgtaataacaagtatttcgccgaaatacggtcctatg gctggtggcactttacttactttaactggaattacctaaacagtgggaat tctagacacatttcaattggtggaaaaacatgtactttaaaaagtgtgtc aaacagtattcttgaatgttatacccccagcccaaaccatttcaactgagt ttgctgttaaattgaaaattgacttagccaaccgagagacaagcatcttc agttaccgtgaagatcccattgtctatgaaattcatccaaccaaatctttt tattagtggtgggagcacaataacaggtgttgggaaaaacctgaattcag ttagtgtcccgagaatggtcataaatgtgcatgaagcaggaaggaacttt acagtggcatgtcaacatcgctctaattcagagataatctgttgtaccac tccttccctgcaacagctgaatctgcaactcccctgaaaaccaaagcct ttttcatgttagatgggatcctttccaaatactttgatctcatttatgta cataatcctgtgtttaagcctttttgaaaagccagtgatgatctcaatggg caatgaaaatgtactggaaattaagggaaatgatattgaccctgaagcag ttaaaggtgaagtgttaaaagttggaaataagagctgtgagaatatacac ttacattctgaagccgttttatgcacggtccccaatgacctgctgaaatt gaacagcgagctaaatatagagtggaagcaagcaatttcttcaaccgtcc ttggaaaagtaatagttcaaccagatcagaatttcacacaccatcatcac catcactgattcgaa
```

Example 2. Binding Assay of Antibody and Antigen (ELISA)

This experiment uses enzyme linked immunosorbent assay (ELISA) to detect affinity of c-Met antibody to c-Met antigen in vitro (including supernatant of hybridoma or recombinantly expressed monoclonal antibodies).

Experimental procedures: Coating buffer (PBS; Hyclone, Cat No.: SH30256.01B) was used to dilute antigen (human c-Met-His, example 1) to 2 μg/ml, which was added to 96-well plate with 100 μl/well (Costar 9018, Cat No.:

03113024) and incubated overnight at 4'C. The next day, the 96-well plate was restored to room temperature and washed three times with washing buffer (PBS+0.05% Tween 20 (Sigma, Cat No.: P1379). Blocking buffer was added at 200 μl/well (PBS+1% BSA (Roche, Cat No.: 738328), and the plate was incubated at 37° C. for 1 hour. The plate was then washed three times with washing buffer. The anti c-Met antibody to be tested was added to the 96-well plate and was incubated for 1 hour at room temperature. The plate was then washed three times with washing buffer. Secondary antibody (Goat anti-Mouse IgG(H+L)(HRP)(Thermo, No.: 31432) diluted with blocking buffer (10000× dilution) was added to the 96-well plate at 100l/well, and the plate was incubated for 1 hour at room temperature. The plate was then washed three times and TMB chromogenic substrate (eBioscience REF:00-4201-56) was added to the 96-well plate at 100 μl/well. Stop solution 2N $H_2SO_4$ was added to the 96-well plate at 100l/well. The plate was read with plate reader at 450 nm.

Example 3. Production of Murine Monoclonal Antibody Cell Line of Anti-Human c-Met Murine anti-human c-Met monoclonal cell lines were obtained by immunizing mice, fusion of spleen cells, and screening of hybridomas. This method is well-known in this field. Recombinantly expressed antigen (human c-Met ECD-mFc, human c-Met Sema-flis, see example 1) was diluted to 1 mg/ml with PBS (Hyclone, Cat No.: SH30256.01B) and emulsified with Freund's adjuvant (The first immunization was performed with Freund's complete adjuvant, and the other booster immunizations were performed with Freund's incomplete adjuvant) and injected into Balb/C mice subcutaneously (5 mice/group), with each mouse inoculated with 100 μg antigen, and booster immunizations were given every two weeks. After the first booster immunization, mice serum was collected during 7 to 10 days after each booster immunization, and the serum titer was detected by ELISA (Methods as in Example 2).

After immunization, mice with a serum titer higher than $1:10^5$ were selected for fusion. Mouse B-cells and myeloma cells (SP2/0, ATCC number: CRL-1581™) were prepared respectively in aseptic conditions and counted. The two kinds of cells were mixed in a proportion of B-cells: SP2/0 of 1:4 and then were centrifuged (1500 r/min, 7 min). The supernatant was discarded, and 1 ml of 50% polyethylene glycol (Supplier: SIGMA, Catalogue # RNBB306) was added. Next, 1 ml serum-free RPMI1640 (Supplier: GIBCO, Catalogue # C22400) was used for termination, and samples were centrifuged for 10 minutes. The supernatant was then discarded. The pellet was resuspended in RPMI1640 which comprises hybridoma cell growth factor (Supplier: Roche, Catalogue #1363735001), serum (Supplier: GIBCO, Catalogue # C20270) and HAT (Supplier: Invitrogen, Catalogue #21060-017). B-cells were plated on the plate at $10^5$/well and 100 μl/well. The plate was placed in cell incubator at 37'C. 3 days later, 100 μl of RPMI1640, which comprises hybridoma cell growth factor, serum and HT (Supplier: Invitrogen, Catalogue #11067-030) was added to each well. After 2 to 4 days, each well was replaced with 150 μl RPMI1640 comprising hybridoma cell growth factor, serum and HT. The next day, positive clones were detected by ELISA (see Methods in Example 2). The results are shown in Table 1.

TABLE 1

Detection of hybridoma fusion in human c-Met immunized mice

| Clone No. | Detection Results (OD450) |
|---|---|
| Negative control | 0.07 |
| Ab-1 | 1.48 |
| Ab-2 | 1.38 |
| Ab-3 | 1.29 |
| Ab-4 | 1.6 |
| Ab-5 | 1.64 |
| Ab-6 | 1.75 |
| Ab-7 | 1.58 |
| Ab-8 | 1.24 |

Example 4. Inhibitory Effect of Anti-Human c-Met Monoclonal Antibody on Proliferation of MKN45 Gastric Cancer Cells The clones above were selected and further cultured to obtain monoclones. After verification of binding activity by ELISA, monoclones were selected for cultivation, and the resulting supernatant was subjected to a cell viability assay. According to the experiment principle, anti-human c-Met antibodies of the invention are able to inhibit phosphorylation of c-Met expressed on the surface of human gastric cancer cell line MKN45, thereby inhibiting the proliferation of MNK45 cells.

Human gastric cancer cells (MKN45, JCRB, JCRB0254, P11) were added to a 96-well cell culture plate (costar, #3799) at $1\times10^5$ cells/mL and 50 μl/well. The medium was RPMI1640 medium: (GIBCO, cat #11835)+10% FBS (GIBCO-10099141). Anti-human c-Met antibodies to be tested were added at 50 μl/well, and the plate was cultured for 5 days in incubator at 37'C (Manufacture: SANYO; Equipment No. TINC035). CellTiter-Glo® Luminescent Cell Viability Assay (Promega, G7573) was used, and the proliferation of cells was detected according to the instructions. The plate was read by a PerkinElmer plate reader, TREA001-RDA-IBA100. The following formula was used to calculate the percentage proliferation of cells: % proliferation of cells=(1−cell reads in experimental group/cell reads in untreated group)×100%. The results are shown in Table 2.

TABLE 2

Anti-human c-Met mAb cell viability

| Clone No. | MKN45 inhibition percentage (%) |
|---|---|
| Blank Control | 0.01 |
| Ab-1 | 59.2 |
| Ab-2 | 58.4 |
| Ab-3 | 59.6 |
| Ab-4 | 54.9 |
| Ab-5 | 77.4 |
| Ab-6 | 70.8 |
| Ab-7 | 56.4 |
| Ab-8 | 53.8 |

Example 5. Anti c-Met Antibody Sequence Cloning

The cell line Ab-5, having good viability obtained (example 4) was selected for cDNA sequence cloning. The mAb was recombinantly expressed and subjected to various activity tests. The variable regions of the heavy chain and light chain of the antibody gene were amplified by reverse transcription PCR, and ligated to vector to obtain the heavy and light chain sequences of the monoclonal antibody by sequencing. First, an RNA purification kit (Qiagen company, No. 74134, see the instructions for this procedure) was used to extract all cell RNAs of the active single cell line from example 4. Next, single stranded cDNA was prepared by the cDNA synthesis kit (Invitrogen company, No. 18080-051), which involves cDNA reverse transcription using Oligo-dT primers. The product served as a template, and the variable region sequence of the antibody heavy and light chain was synthesized by PCR. The products of PCR were cloned into the TA vector pMD-18T and then sequenced. The obtained heavy and light chain sequences of the antibody were separately cloned to expression vectors (see example 1), and the monoclonal antibody was recombinantly expressed to prove its activity (see examples 2 and 4), followed by humanization. Sequence of mouse hybridoma cell monoclonal antibody Ab-5:

Heavy chain variable region:
(SEQ ID NO: 4)
QVQLKQSGPGLVQPSQSLSITCTVSGFSLPNYGVHWVRQSPGKGLEWLGV

IWSGGSTNYAAAFVSRLRISKDNSKSQVFFEMNSLQADDTAVYYCARNHD

NPYNYAMDYWGQGTTVTVSS

Light chain variable region:
(SEQ ID NO: 5)
DIVLTQSPGSLAVYLGQRATISCRANKSVSTSTYNYLHWYQQKPGQPPKL

LIYLASNLASGVPARFSGSGSGTDFTLNIHPLEEEDAATYYCQHSRDLPP

TFGAGTKLELKR

The amino acid residues of VH/VL CDR of anti-human c-Met antibodies were determined and annotated by the Kabat numbering system.

The CDR sequences of mouse-origin anti-c-Met antibody of the invention are shown in Table 3:

TABLE 3

| CDR sequence of Mouse-origin anti-c-Met antibody | |
|---|---|
| Antibody | Ab-5 |
| Heavy chain CDR1 | NYGVH (SEQ ID NO: 6) |
| Heavy chain CDR2 | VIWSGGSTNYAAAFVS (SEQ ID NO: 7) |
| Heavy chain CDR3 | NHDNPYNYAMDY (SEQ ID NO: 8) |
| Light chain CDR1 | RANKSVSTSTYNYLH (SEQ ID NO: 9) |
| Light chain CDR2 | LASNLAS (SEQ ID NO: 10) |
| Light chain CDR3 | QHSRDLPPT (SEQ ID NO: 11) |

Example 6. Humanization of Anti c-Met Antibody

The mouse-origin anti-c-Met monoclonal antibody heavy and light chain sequences obtained from example 5 were aligned against an antibody database for homology, and a humanized antibody model was established. Depending on the model, the optimal humanized c-Met monoclonal antibody was selected as the preferred molecule of the invention according to reversion mutation, as described below. A crystal structure showing similar homology with the obtained murine candidate molecules was selected from the published database of mice Fab crystal structure models (e.g. PDB database), and a Fab crystal structure with high resolution (such as, less than 2.5 Å) was selected; and the mouse Fab model was established. The murine antibody heavy and light chain sequences of the invention were aligned against the sequences in the model, and the constant sequence was maintained so that the structural model of the mouse antibody of the invention could be obtained. The variable amino acids might be potential sites for reverse mutation. Swiss-pdb viewer software was used to run the mouse antibody structure model to optimize energy (minimization). Reverse mutation was performed at different amino acid sites other than those in CDRs of the model, and the resultant humanized antibody was aligned against that before humanization to detect the activity. A humanized antibody with good activity was maintained. The CDR region was then further optimized, including mutations to prevent glycosylation, deamination, oxidation sites and so on. The CDRs of the optimized humanized anti c-Met antibody are shown in Table 4:

TABLE 4

| CDR sequence of optimized anti c-Met antibody | |
|---|---|
| Antibody | Optimized humanized antibody |
| Heavy Chain CDR1 | NYGVH (SEQ ID NO: 6) |
| Heavy Chain CDR2 | VIWSGGSTNYAAAFVS (SEQ ID NO: 7) |
| Heavy Chain CDR3 | NHDNPYNYAMDY (SEQ ID NO: 8) |
| Light Chain CDR1 | RADKSVSTSTYNYLH (SEQ ID NO: 12) |
| Light Chain CDR2 | LASNLAS (SEQ ID NO: 10) |
| Light Chain CDR3 | QHSRDLPPT (SEQ ID NO: 11) |

Variable regions of the humanized heavy and light chain sequences of the optimized humanized anti c-Met antibodies are shown below:

1. Heavy chain variable region
Ab-9
(SEQ ID NO: 13)
QVTLKESGPVLVKATETLTLTCTVSGFSLPNYGVHWVRQPPGKALEWLAV

IWSGGSTNYAAAFVSRLRISKDTSKSQVVFTMNNDPVDTATYYCARNHDN

PYNYAMDYWGQGTTVTVSS

Ab-10
(SEQ ID NO: 14)
QVQLVESGGGVVQPGRSLRLSCAASGFSLSNYGVHWVRQAPGKGLEWLAV

IWSGGSTNYAAAFVSRLTISKDNSKNTVYLQMNSLRAEDTAVYYCARNHD

NPYNYAMDYWGQGTTVTVSS

Ab-11
(SEQ ID NO: 15)
QVQLVESGGGVVQPGRSLRLSCAASGFTLPNYGVHWVRQAPGKGLEWLAV

IWSGGSTNYAAAFVSRLTISKDNSKNTVYLQMNSLRAEDTAVYYCARNHD

NPYNYAMDYWGQGTTVTVSS

2. Light chain variable regions
Ab-9
(SEQ ID NO: 16)
DIVLTQSPASLAVSPGQRATITCRANKSVSTSTYNYLHWYQQKPGQPPKL
LIYLASNLASGVPARFSGSGSGTDFTLTINPVEANDTANYYC**QHSRDLPP
T**FGQGTKLEIKR Ab-10
(SEQ ID NO: 17)
DIVLTQSPDSLAVSLGERATINCRADKSVSTSTYNYLHWYQQKPGQPPKL
LIYLASNLASGVPDRFSGSGSGTDFTLTISSLQAEDVAVYYC**QHSRDLPP
T**FGQGTKLEIKR Ab-11
(SEQ ID NO: 18)
DIVLTQSPDSLAVSLGERATINCRANKSVSTSTYNYLHWYQQKPGQPPKL
LIYLASNLASGVPDRFSGSGSGTDFTLTISSLQAEDVAVYYC**QHSRDLPP
T**FGQGTKLEIKR The humanized heavy and light chain sequences were recombined with IgG Fc regions to obtain the humanized anti c-Met monoclonal antibody of the invention. The Fc sequence used was selected optionally from the following sequences:
Heavy chain constant region:

Heavy chain constant region:
(SEQ ID NO: 19)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK (SEQ ID NO: 20)
ASTKGPSVFPLAPCSRSTSESTAALGCLVKDYFPEPVTVSWNSGALTSGV

HTFPAVLQSSGLYSLSSVVTVPSSNFGTQTYTCNVDHKPSNTKVDKTVER

KCCVECPPCPAPPVAGPSVFLFPPKPKDTLMISRTPEVTCVVVDVSHEDP

EVQFNWYVDGVEVHNAKTKPREEQFNSTFRVVSVLTVVHQDWLNGKEYKC

KVSNKGLPAPIEKTISKTKGQPREPQVYTLPPSREEMTKNQVSLTCLVKG

FYPSDIAVEWESNGQPENNYKTTPPMLDSDGSFFLYSKLTVDKSRWQQGN

VFSCSVMHEALHNHYTQKSLSLSPGK (SEQ ID NO: 21)
ASTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVES

KYGPPCPPCPAPEFLGGPSVFLFPPKPKDTLMISRTPEVTCVVVDVSQED

PEVQFNWYVDGVEVHNAKTKPREEQFNSTYRVVSVLTVLHQDWLNGKEYK

CKVSNKGLPSSIEKTISKAKGQPREPQVYTLPPSQEEMTKNQVSLTCLVK

GFYPSDIAVEWESNGQPENNYKTTPPVLDSDGSFFLYSRLTVDKSRWQEG

NVESCSVMHEALHNHYTQKSLSLSLGK

Light chain constant region:
(SEQ ID NO: 22)
TVAAPSVFIFPPSDEQLKSGTASVVCLLNNFYPREAKVQWKVDNALQSGN

SQESVTEQDSKDSTYSLSSTLTLSKADYEKHKVYACEVTHQGLSSPVTKS

FNRGEC

The above antibodies were cloned, expressed and purified by gene cloning and recombination expression, respectively. The humanized antibodies with the best activity, Ab-9, Ab-10, and Ab-11 were finally selected by ELISA (Example 2) and in vitro binding activity assay (Example 7). The sequences are shown as below:
Ab-9 humanized antibody:

Heavy chain:
(SEQ ID NO: 23)
QVTLKESGPVLVKPTETLTLTCTVSGFSLPNYGVHWVRQPPGKALEWLAV

IWSGGSTNYAAAFVSRLRISKDTSKSQVVFTMNNMDPVDTATYYCARNHD

NPYNYAMDYWGQGTTVTVSSASTKGPSVFPLAPCSRSTSESTAALGCLVK

DYFPEPVTVSWNSGALTSGVHTFPAVLQSSGLYSLSSVVTVPSSNFGTQT

YTCNVDHKPSNTKVDKTVERKCCVECPPCPAPPVAGPSVFLFPPKPKDTL

MISRTPEVTCVVVDVSHEDPEVQFNWYVDGVEVHNAKTKPREEQFNSTFR

VVSVLTVVHQDWLNGKEYKCKVSNKGLPAPIEKTISKTKGQPREPQVYTL

PPSREEMTKNQVSLTCLVKGFYPSDIAVEWESNGQPENNYKTTPPMLDSD

GSFFLYSKLTVDKSRWQQGNVFSCSVMHEALHNHYTQKSLSLSPGK

Light chain:
(SEQ ID NO: 26)
DIVLTQSPASLAVSPGQRATITCRANKSVSTSTYNYLHWYQQKPGQPPKL

LIYLASNLASGVPARFSGSGSGTDFTLTINPVEANDTANYYCQHSRDLPP

TFGQGTKLEIKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC

Ab-10 Humanized Antibody:

Heavy chain:
(SEQ ID NO: 24)
QVQLVESGGGVVQPGRSLRLSCAASGFSLSNYGVHWVRQAPGKGLEWLAV

IWSGGSTNYAAAFVSRLTISKDNSKNTVYLQMNSLRAEDTAVYYCARNHD

NPYNYAMDYWGQGTTVTVSSASTKGPSVFPLAPCSRSTSESTAALGCLVK

DYFPEPVTVSWNSGALTSGVHTFPAVLQSSGLYSLSSVVTVPSSNFGTQT

YTCNVDHKPSNTKVDKTVERKCCVECPPCPAPPVAGPSVFLFPPKPKDTL

MISRTPEVTCVVVDVSHEDPEVQFNWYVDGVEVHNAKTKPREEQFNSTFR

VVSVLTVVHQDWLNGKEYKCKVSNKGLPAPIEKTISKTKGQPREPQVYTL

PPSREEMTKNQVSLTCLVKGFYPSDIAVEWESNGQPENNYKTTPPMLDS

DGSFFLYSKLTVDKSRWQQGNVFSCSVMHEALHNHYTQKSLSLSPGK

Light chain:
(SEQ ID NO: 27)
DIVLTQSPDSLAVSLGERATINCRADKSVSTSTYNYLHWYQQKPGQPPKL

LIYLASNLASGVPDRFSGSGSGTDFTLTISSLQAEDVAVYYCQHSRDLPP

-continued
TFGQGTKLEIKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC

Ab-11 Humanized Antibody:

Heavy chain:
(SEQ ID NO: 25)
QVQLVESGGGVVQPGRSLRLSCAASGFTLPNYGVHWVRQAPGKGLEWLAV

IWSGGSTNYAAAFVSRLTISKDNSKNTVYLQMNSLRAEDTAVYYCARNHD

NPYNYAMDYWGQGTTVTVSSASTKGPSVFPLAPCSRSTSESTAALGCLVK

DYFPEPVTVSWNSGALTSGVHTFPAVLQSSGLYSLSSVVTVPSSNFGTQT

YTCNVDHKPSNTKVDKTVERKCCVECPPCPAPPVAGPSVFLFPPKPKDTL

MISRTPEVTCVVVDVSHEDPEVQFNWYVDGVEVHNAKTKPREEQFNSTFR

VVSVLTVVHQDWLNGKEYKCKVSNKGLPAPIEKTISKTKGQPREPQVYTL

PPSREEMTKNQVSLTCLVKGFYPSDIAVEWESNGQPENNYKTTPPMLDSD

GSFFLYSKLTVDKSRWQQGNVFSCSVMHEALHNHYTQKSLSLSPGK

Light chain:
(SEQ ID NO: 28)
DIVLTQSPDSLAVSLGERATINCRANKSVSTSTYNYLHWYQQKPGQPPKL

LIYLASNLASGVPDRFSGSGSGTDFTLTISSLQAEDVAVYYCQHSRDLPP

TFGQGTKLEIKRTVAAPSVFIFPPSDEQLKSGTASVVCLLNNFYPREAKV

QVVKVDNALQSGNSQESVTEQDSKDSTYSLSSTLTLSKADYEKHKVYACE

VTHQGLSSPVTKSFNRGEC

Example 7. In Vitro Activity Detection of Binding of Anti c-Met Humanized Antibody Humanized antibodies of the invention were analyzed for their in vitro activity by ELISA (Example 2), and also analyzed for their binding with the cell line MKN45, which overexpresses c-Met, and for their affinity to c-Met antigen (BIACore detection). The results are shown in Table 5 and Table 6.

A FACS method was used to detect the binding activity of c-Met humanized antibodies with the cell line MKN45, which overexpresses c-Met.

MKN45 cells (JCRB, Cat No.: JCRB0254) were resuspended in RPMI1640 medium (GIBCO, Cat No.: 11835-030) which contains 10% (v/v) fetal calf serum (FBS GIBCO, Cat No.: 10099-141) and Penicillin/Streptomycin Solution (GIBCO, Cat No.: 15070-063) to reach 10,000,000 cells/mL. 2 mL of resuspended MKN45 cells was added to 96-well microtiter plate (Corning, Cat No.: 3799) at 150,000 cells/well, and 8 concentrations of c-Met antibody (5× serial dilution, starting from 20 µg/ml) were added to the corresponding wells, and the final volume was 100 µl. The plate was incubated for 1 hour at 4° C. FACS buffer (PBS comprising 2.5% (v/v) FBS (Hyclone, Cat: SH30256.01B)) was added. The plate was centrifuged under 4° C. at 1300 rmp for 4 minutes, and the supernatant was discarded. This procedure was repeated three times. 100 µl of secondary antibodies (Fluorescence labeled goat-anti-mouse secondary antibodies with 1:200 dilution, Biolegend, Cat No. 405307; Fluorescence labeled anti-human secondary antibody with 1:30 dilution, Biolegend, Cat No. 409304) were added to each well, and the plate was incubated for 1 hour at 4° C. FACS buffer was added, the plate was centrifuged under 4° C. at 1300 rpm for 4 minutes, the supernatants were discarded; and this procedure was repeated three times. 200 µl FACS buffer was added to resuspend the cells, and the samples were prepared and detected by flow cytometry (BD FACS Array).

The affinity of c-Met antibody to c-Met antigen Sema-His was detected by surface plasmon resonance (SPR) in the invention.

Anti-mouse IgG (GE Life Sciences catalog # BR-1008-38) or anti-human IgG (GE Life Sciences catalog # BR-1008-39) antibodies were respectively diluted to 30 µg/ml and 50 µg/ml by sodium acetate solution, pH 5.0 (GE Healthcare, Cat # BR-1003-51). An amino coupling kit (GE Life Sciences, Cat # BR100050) was immobilized onto the test channels and control channels on a CM5 chip (GE Life Sciences catalog # BR-1000-12), and the coupling level was set at 15000 RU. Running buffer PBS (Hyclone, Cat # SH30256.01B)+0.05% P20 (GE Life Sciences, Cat # BR-1000-54) was used to dilute the c-Met antibody to 1.5 µg/ml. Antigen Sema-His was diluted to 200 nM with running buffer, and then diluted at a 1:2 dilution with the same buffer until it reached 0.78 nM. The diluted antibody passed through the test channel for 1 minute at a speed of 30 l/min, and the antigen passed through the test channels and control channels for 3 minutes at the same speed. After 10 minutes of dissociation, the flow speed was adjusted to 10 µl/min, and regeneration buffer was passed through test channels and control channels for 3 minutes. Data was fitted by BiaEvaluation 4.1 after double deduction, and the fitting model was a 1:1 Langmuir model.

TABLE 5

Binding activity of humanized anti c-Met antibody

| | Humanized antibody | | |
|---|---|---|---|
| | Ab-9 | Ab-10 | Ab-11 |
| ELISA detection (EC$_{50}$, nM) | 0.13 | 0.39 | 0.2 |

TABLE 6

Binding activity of humanized anti c-Met antibody with MKN45 cells; and affinity of humanized anti c-Met antibody to antigen

| Humanized antibody | MKN45/FACS Binding activity (nM) | affinity to antigen Biacore (nM) |
|---|---|---|
| Ab-9 | 1.6 | 4 |
| Ab-10 | 1.23 | 8 |

The above results show that the binding activity of humanized antibodies with antigen is within 0.13-8 nM, and the results can vary depending on the detection methods used. The results show that humanized anti c-Met antibodies maintain the binding activity of the parent antibodies prior to humanization.

Example 8. In Vitro Function and Cell Viability Evaluation of Anti c-Met Humanized Antibody To detect the function of antibodies of the invention, a test of their ability to block the binding between c-Met ligand (hepatocyte growth factor, HGF) and c-Met, as well as an inhibition test of cell proliferation (Example 4) were performed to evaluate the antibodies in example 7.

Binding of HGF with c-Met results in tyrosine phosphorylation of c-Met molecules and activation of the c-Met signaling pathway. The ability of anti c-Met antibodies of the invention to block HGF from binding with the receptor c-Met protein (i.e. $IC_{50}$) was measured by ELISA.

c-Met ECD-mFc (Example 1) was diluted in PBS (Hyclone, Cat # SH30256.01B) with a final concentration of 2 μg/ml, and then a 96-well ELISA plate (Costar, cat #2592) was coated with c-Met ECD-mFc at room temperature overnight. The plate was washed with PBST (PBS+0.05% tween 20, Simga, Cat # P1379) 3 times on a plate washer (Suppler: BioTex; Model: ELX405; S/N: 251504). 300 μl blocking solution PBS+1% BSA (Roche, Cat #738328) was added to the 96-well plate, and the plate was incubated for 60 minutes at 37° C. After the plate was washed with PBST 3 times, 50 μl of antibody diluted by blocking solution was added to the 96-well plate, and the plate was incubated for 90 minutes at 37° C. 50 μl of human HGF (Sino Biological, #10463-HNAS), which had been diluted with blocking solution to a final concentration of 20 ng/ml, was added to the 96-well plate containing c-Met antibodies, and the plate was incubated for 120 minutes at room temperature. After the plate was washed with PBST 3 times, 100 μl of biotin-labeled anti HGF antibody (R&D, Cat # BAF294), which had been diluted with blocking solution to a final concentration of 100 ng/ml, was added to the 96-well plate and incubated for 90 minutes. After the plate was washed with PBST 3 times, 100 μl of horseradish peroxidase (ebioscience, #18-4100-51) diluted with blocking solution was added to the 96-well plate and incubated for 30 minutes. After the plate was washed with PBST 3 times, 100 μl substrate (ebioscience, cat #00-4201-56) was added to the plate and incubated for 10 minutes at room temperature. 100 μl stop solution ($2N\ H_2SO_4$) was added, and data was read by a 450 nM microplate reader (Supplier: Moleculer Devices; Model: MNR0643; Equip ID: TMRP001). Data analysis was performed by SoftMax Pro v5. The results are shown in Table 7.

TABLE 7 in vitro function and cell viability evaluation of anti c-Met humanized antibodies

| Humanized antibody | Activity of inhibition of HGF/c-Met binding ($IC_{50}$, nM) | Activity of inhibition of MKN45 cell proliferation | |
|---|---|---|---|
| | | $IC_{50}$ (nM) | Maximum inhibition rate (%) |
| Ab-9 | 1.42 | 0.52 | 33 |
| Ab-10 | 1.50 | 0.55 | 30 |

The above results show that humanized antibodies of the invention not only retains the binding activity with antigen, but also block the binding between antigen and ligand. It also shows the inhibition of growth activity of cancer cells.

Example 9. Agonist Activity Evaluation of Anti c-Met Humanized Antibody

An anti c-Met antibody that blocks HGF/c-Met binding may activate c-Met signaling, meaning that the c-Met antibody has agonist activity. The agonist activity of an anti c-Met antibody is not desired in the invention. To determine whether antibodies of the invention have agonist activity, three experiments were performed including c-Met phosphorylation, proliferation of metastatic human clear renal cell carcinoma (caki-1), and human lung cancer H441 cell migration. The detection and evaluation have been done.

The binding of HGF to c-Met activates both tyrosine phosphorylation of the c-Met molecule and the c-Met signaling pathway. Therefore, the activation of c-Met by HGF was used as a positive control of the agonist experiment, and human lung cancer cell line A459 was used to evaluate the induced phophorylation of c-Met tyrosine residue 1349.

A549 cells were suspended in solution containing Ham's F12K, 2 mM glutamine (Invitrogen, #21127-022), and 10% (v/v) FBS (GIBCO, #10099141). 0.2 mL of cell suspension was taken and added to a 96-well plate (Corning, #3599), and the cell concentration was 60000 cells/well. The plate was incubated for 24 hours under 5% $CO_2$ at 37° C. After 24 hours, the media in the 96-well plate was discarded, and 100 μl low serum medium (Ham's F12K+2 mM glutamine+ 0.5% FBS) was added. The cells were starved for 6 hours under 5% $CO_2$ at 37° C. Antibodies were diluted using the above low serum medium to a final concentration of 20 μg/ml. The HGF concentration in the positive control was 200 ng/ml. The plate was incubated for 15 minutes at 37° C. After the media was discarded, 50l cell lysis solution (10 mM Tris, 150 mM NaCl, 2 mM EDTA), 50 nM NaF, 1% (v/v) TRITON-X 100, protease inhibitors (Roche cat #05892791001), phosphatase inhibitors cocktail II (Sigma # P5726) and phosphatase inhibitors cocktail III (Sigma # P0044) were added into the plate. After cell lysis, c-Met tyrosine phosphorylation was detected by ELISA. A c-Met capture antibody (CST, cat #3148s) was diluted with PBS at a 1:1000 dilution, and then added to the 96-well ELISA plate (costar, cat #9018) at 100 μl per well. The plate was incubated at 4° C. overnight. The plate was washed 3 times with TBS-T, 300 μl blocking solution (TBS-T plus 2% (w/v) BSA) was added, and the plate was incubated for 1 hour. The plate was washed 3 times with TBS-T. 75 μl cell blocking solution and 25 μl cell lysate were added, and the plate was incubated at 4° C. overnight. The plate was washed 3 times with TBS-T, and pY1349 c-Met antibody (cell signal, #3133) was diluted with blocking solution at 1:1000 dilution, and added to the plate at 100 μl per well. After a 2-hour incubation at room temperature, the plate was washed 4 times with TBST, and the HRP-labeled goat anti-rabbit polyclonal antibody (cell signaling, cat #7074) was diluted with blocking solution at 1:12000 and added to the plate at 100 μl per well. The plate was incubated for 1 hour at room temperature. The plate was washed with TBS-T 5 times, and 100 μl of TMB (ebioscience # TMB, 004201) was added to each well, then 100 μl of stop solution ($2N\ H_2SO_4$) was added. Data was read by a 450 nM microplate reader (Supplier: Moleculer Devices; Model: MNR0643; Equip ID: TMRP001). SoftMax Pro v5 was used for data analysis. The results are shown in Table 8.

Caki-1 cells express the hepatocyte growth factor receptor c-Met, and HGF can bind c-Met to stimulate Caki-1 cell proliferation. Therefore, agonist activity of anti c-Met antibodies could be evaluated by the proliferation of Caki-1 cells stimulated by the humanized anti c-Met antibodies of the invention compared with the proliferation of Caki-1 cells stimulated by HGF.

Caki-1 cells (Shanghai Branch of Chinese Academy of Science, TCHu135, P12) were added to a 96-well culture plate (costar, #3799) at 1000/well. The medium was McCoy's 5A (invitrogen, #16600)+10% FBS (GIBCO-10099141), and the condition was at 37° C. for 24 hours. Afterwards, cells were starved for 24 hours (The medium for cell starvation is McCoy's 5A and 0.5% FBS). After starvation, cells were treated with serially diluted anti c-Met antibodies (The highest concentration was 20 μg/ml) and positive controls for 5 days, and cell proliferation was detected by a cell proliferation assay kit (CellTiter-Glo® Luminescent Cell Viability Assay (Promega, G7573). The plate was read by a plate reader (Manufacture: PerkinElmer device No.: TREA001-RDA-IBA100). The proliferation percentage of the cell was calculated: proliferation %=reads obtained from cells in test group/reads obtained from cells in untreated group×100%. The results show that anti-c-Met antibodies of the invention have no effect on proliferation of Caki-1 cells; data are shown in Table 8.

If anti c-Met antibodies have agonist activity, the migration ability of cells could be affected. The H441 cell line expressing c-Met is used in the invention to evaluate the ability of c-Met antibodies to affect cell migration. H441 cells (ATCC, Cat No.: HTB-174) were resuspended to 500,000 cells/ml in RPMI 1640 medium (GIBCO, Cat No.: 11835-030) which contains 10% (v/v) FBS (GIBCO, Cat No.: 10099-141) and penicillin-streptomycin (GIBCO, Cat No.: 15070-063). The resuspended H441 cells were added to a 12-well culture plate (Costar, Cat No. 3513) at 1 ml/well, and were cultured for 3 days at 37° C. in 5% $CO_2$. Cells were washed twice with PBS, and RPMI 1640 medium containing 0.5% FBS was added, and the plate was cultured for 16 hours at 37° C. in 5% $CO_2$. The bottom of each well was scratched with 5 ml tips, and the plate was washed once with medium containing low concentration of FBS, and 1 ml of RPMI 1640 medium containing a low concentration of serum was added. The plate was marked, photos were taken for randomly selected scratch areas under an inverted microscope at 4× magnification. This time was set as the starting point. Cells were treated with 10 μg/ml c-Met antibody or HGF control (200 ng/ml) for 16 hours at 37° C. in 5% $CO_2$. After that, photos for the marked scratch areas were taken under an inverted microscope at 4× magnification, and this time was set as the time after migration. The percentage of cell migration was measured as the migration distance relative to the starting point divided by the migration distance of the test group relative to the starting point, and then multiplied by 100. The results are shown in Table 8.

TABLE 8

Evaluation of agonist activity of humanized anti c-Met antibodies

| Humanized antibody | Activation of c-Met phosphorylation (%)* | Stimulation of proliferation of Caki-1 | H441 migration (%)# |
|---|---|---|---|
| Ab-9 | 29.9 | none | 53 |
| Ab-10 | 33.7 | none | 34 |

*Antibody concentration was 20 μg/ml, the activation of c-Met phosphorylation by HGF (200 ng/ml) was set as 100%.
Antibody concentration was 20 μg/ml, H441 migration % affected by HGF (200 ng/ml) was set as 100%.

From the above results, the humanized antibodies showed low (c-Met phosphorylation, H441 migration) or no (Caki-1 proliferation stimulation) agonist activity.

Example 10. Pharmacological Evaluation of Anti c-Met Antibody In Vivo

The human gastric cancer MKN45 cell model, obtained by subcutaneous xenograft into BALB/c nude mice, was used to evaluate the antitumor activity of the antibodies.

MKN45 cells were cultured in a monolayer in RPMI-1640 medium (10%/FBS) at 37° C. in 5% $CO_2$. The cells were counted and collected during the logarithmic phase. The cells were resuspended in PBS to an appropriate concentration, and 0.1 ml 3×10⁶ cells were subcutaneously injected into the right wing of mice (BALB/c nude mouse, female, 10-week old, 22-28 g, from Shanghai SLAC experimental animal ltd. Licence No. 2007000548777; Environment: SPF grade). When the tumors' average volume reached 114 $mm^3$, the tumors' weights and volumes were measured, and mice were then separated into groups for treatment. The control group was treated with PBS, and the antibody therapy group was treated with 5 mg/kg antibody of the invention, and the frequency was once a week and twice per time. The tumors' volumes and weights were measured twice a week, and the experiment was terminated at day 25. The formula for calculating tumor size was: tumor volume ($mm^3$)=0.5×(tumor length×tumor diameter²). The formula for calculating inhibition rate was: inhibition rate= $(V_0-V_T)/V_0 \times 100\%$, and $V_0$, $V_T$ are respectively the volume of tumor at the beginning and at the end of the experiment.

The results shows that the inhibition rate of antibodies Ab-9 and Ab-10 were 56% and 64%, respectively. There was no obvious change in mice weight during the experiment (22-24 g). This results show that the humanized anti c-Met antibodies could inhibit the growth of a tumor in vivo.

Example 11. Endocytosis of Anti c-Met Antibody

Antibodies of the invention could bind to human c-Met, have very good in vitro activity, and inhibit tumor activity in vivo. Additionally, the antibodies do not have, or have very weak, agonist activity. In order to detect whether the antibody could be taken up into the cell along with human c-Met once bound to human c-Met, the human gastric cancer cell line MKN45 (JCRB, Cat No.: JCRB0254) expressing c-Met was used for evaluation.

MKN45 cells were resuspended to 10,000,000 cells/mL in RPMI 1640 medium (GIBCO, Cat No.: 11835-030), which contains 10% (v/v) FBS (GIBCO, Cat No.: 10099-141) and penicillin-streptomycin (GIBCO, Cat No.: 15070-063). 2 mL resuspended MKN45 cells were added to a 96-well microtiter plate at 250,000 cells/well, and 10 μg/ml of c-Met antibody was added to the corresponding wells, and the final volume was 100 μl. The plate was incubated at 4° C. for 1 hour. FACS buffer (phosphate buffer solution including 2.5% fetal bovine serum; Hyclone, Cat: SH30256.01B) was added, and the plate was centrifuged at 4° C., 1300 rpm for 4 minutes. The supernatant was discarded, and this procedure was repeated three times. 100 μl secondary antibody solution (Fluorescence labeled goat anti mouse secondary antibodies at 1:200 dilution, Biolegend, Cat No. 405307; Fluorescence labeled anti-human secondary antibody at 1:30 dilution, Biolegend, Cat No. 409304) was added into each well, and the plate was incubated at 4° C. for 1 hour. FACS buffer was added and the plate was centrifuged at 4° C., 1300 rpm for 4 minutes. The supernatant was discarded, and this procedure was repeated three times. Complete cell culture medium (RPMI 1640 medium with 10% FBS) was added, and the plate was incubated at 37° C. in 5% $CO_2$ for 0, 0.5, 1, 2, or 4 hours. 5 μl 7-AAD (Biolegend, Cat: 420403) was added to 100 μl FACS buffer which was added to each well, and the plate was incubated at 4° C. for 30 minutes. FACS buffer was added and the plate was centrifuged at 4° C., 1300 rpm for 4 minutes. The supernatant was discarded, and this procedure was repeated three times. 200 μl Stripping buffer (0.05 M glycine, pH 3.0; 0.1 M NaCl, mixed in accordance with 1:1 (v/v)) was added to each well. The cells were resuspended and were incubated for 7 minutes at room temperature. The cells were centrifuged at room temperature at 1300 rpm for 4 minutes, and the supernatant was discarded. 200 μl neutralizing wash buffer (0.15M trihydroxymethyl aminomethane, pH 7.4) was added to each well, the cells were resuspended and centrifuged at room temperature at 1300 rpm for 4 minutes, and the supernatant was discarded. 200 μl FACS buffer was added, and the cells were resuspended. Samples were prepared and detected by flow cytometry (BD FACS Calibur). The results are shown in Table 9.

Endocytosis of c-Met antibody %=(intensity of fluorescence at various time points−average intensity of fluorescence at time 0)/average intensity of fluorescence at time 0.

TABLE 9

Evaluation of cell endocytosis of humanized anti c-Met antibodies (endocytosis %)

| Humanized antibody | 0 h | 0.5 h | 1 h | 2 h | 4 h |
|---|---|---|---|---|---|
| hIgG (control)* | 0 | −0.9 | −4.4 | −4.9 | 3.6 |
| Ab-9 | 0 | 26 | 32 | 32 | 31 |
| Ab-10 | 0 | 24 | 38 | 53 | 59 |

*control group: Experimental error was from 4.9% to 3.6%, and was classified as no endocytosis.

Table 9 shows that antibodies of the invention have good endocytosis without agonist activity. Once bound with target cells, both antibodies and receptors were rapidly taken up into target cells, and the maximum value was reached within 2-4 hours.

Example 12. Analysis of the Biophysical Stability of Anti c-Met Antibodies

To evaluate the biophysical stability of the antibodies of the invention, such as the presence of glycosylation and deamination and stability, LC-MS analysis was used.

The molecular weight of the heavy and light chains was detected by LC-MS to analyze glycosylation. Deamination was analyzed by LC-MS at 4° C. for a long time (at least 3 months), or at 40° C. for 21 days under an accelerated condition. Samples treated with different conditions were diluted to 2 mg/ml with pH7.2 Tris-HCl, and added into 10 mM TCEP and 6M urea (AMRESCO, Cat #0378)$_3$, then the samples were incubated for 20 minutes at 7° C. IAA(Sigma-Aldrich, Cat # I1149) with a final concentration of 20 mM was added and was incubated for 15 minutes in darkness to protect the sulfhydryl group. The pH was adjusted using pH7.2 Tris-HCl, and protease (Sigma-Aldrich, Cat # T6567) was added at a proportion by weight of 10:1 (protein: enzyme). The samples were incubated at 37° C. for 25 minutes, and then formic acid with a final concentration of 0.1% (Fluca, Cat #94318) was added to terminate the reactions. Samples were centrifuged and analyzed by LC-MS.

BiopharmaLynx was used to analyze the presence of deamination. An Extracted Ion Chromatogram (EIC) diagram was obtained from LC-MS data by searching native peptides comprising deamination sites and modified product, and then extracting the parent ion. The peak area was obtained by integration, and the percentages of deamination and oxidation were calculated. The results are shown in Table 10.

TABLE 10

Evaluation of physical stability of the humanized anti c-Met antibodies of the invention

| Antibody of the invention | Molecular weight of light chain* | | Analysis of deamination# | |
|---|---|---|---|---|
| | Detected value | Estimated value | 4° C., 3.5 months | 40° C., 21 days |
| Ab-9 | 25940 | 23907 | 0.66 | |
| Ab-10 | 23828 | 23832 | | 0.3 |

*Heavy chains all contain glycosylation, and the molecular weight was as expected.
Proportion of deamination molecules (%).
0.66-1.0% is within the background of detection.

The above results shows that antibodies of the invention are stable and have good physical properties.

Example 13. Anti-c-Met Antibody Ab-10 Conjugated with Toxin MC-MMAF

The anti-c-Met antibodies of the present invention have inhibitory activity against receptor binding, without having agonist activity, show endocytosis activity in targeted cells, and display physical stability. These properties make the antibodies of the invention particularly suitable for the preparation of ADC drugs when conjugated to toxins for the treatment of c-Met expressing cancers. The coupling process is shown below:

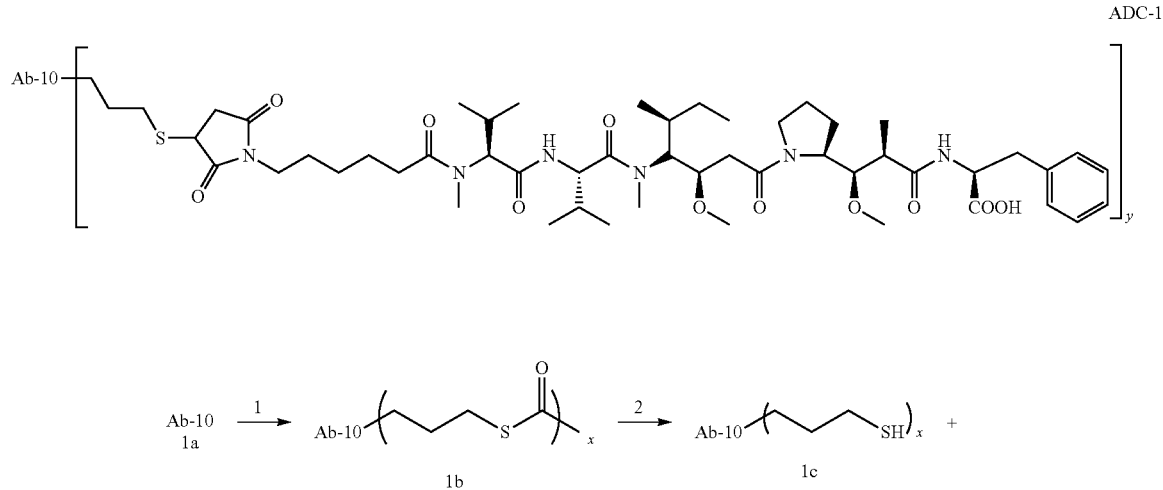

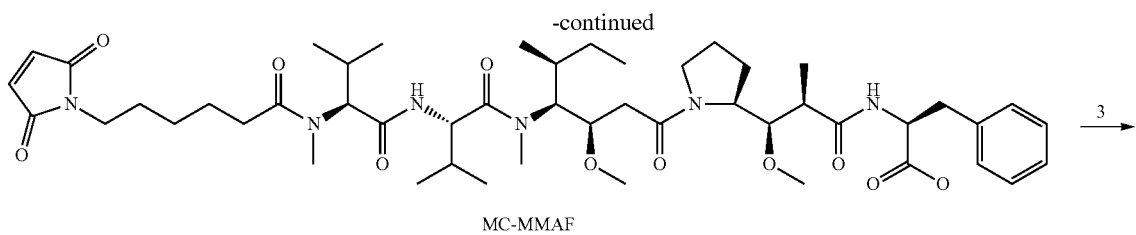

MC-MMAF

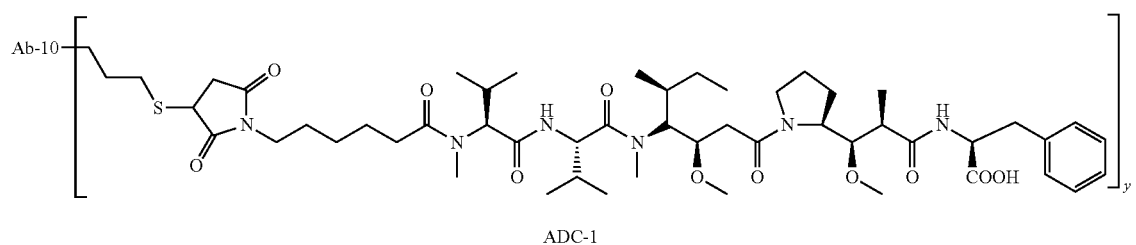

ADC-1

Step 1. Thioacetic acid S-(3-carbonyl propyl) ester (0.7 mg, 5.3 μmol) was dissolved in 0.9 mL acetonitrile solution. The acetonitrile solution of thio acetic acid S-(3-carbonyl propyl) ester prepared above was added into acetic acid/sodium acetate buffer pH 4.3 (10.35 mg/ml, 9.0 ml, 0.97 mmol) containing Ab-10 monoclonal antibody, and 1.0 mL sodium borohydride aqueous solution (14.1 mg, 224 μmol) was added with shaking for 2 hours at 25° C. At the end of the reaction, desalination and purification were done on a Sephadex G25 gel column (Elution phase: 0.05M of PBS solution pH 6.5), and product 1b solution was collected and was concentrated to 10 mg/ml directly for the next reaction.

Step 2. 0.35 ml 2.0M of hydroxylamine hydrochloride solution was added into 11.0 mL of 1b solution with shaking for 30 minutes at 25° C., and then desalination and purification were done on a Sephadex G25 gel column (Elution phase: 0.05M of PBS solution pH 6.5), and the captioned product Ab-10 monoclonal antibody-propyl mercaptan 1c solution was collected (6.17 mg/ml, 14.7 mL).

Step 3. MC-MMAF (1.1 mg, 1.2 μmol; prepared by method published in PCT patent WO2005081711) was dissolved in 0.3 ml acetonitrile and was added to 3.0 ml of Ab-10 monoclonal antibody-propyl mercaptan 1 c solution (6.17 mg/ml) with shaking for 4 hours at 25° C., and then desalination and purification were done on a Sephadex G25 gel column (Elution phase: 0.05M of PBS solution pH 6.5).

The PBS buffer solution of the captioned product ADC-1 (3.7 mg/ml, 4.7 ml) was obtained by filtration through a 0.2 μm filter under aseptic conditions, and then stored at 4° C.

Q-TOF LC/MS: characteristic peak: 148119.2 ($M_{Ab}$+0D), 149278.1 ($M_{Ab}$+1D), 150308.1 ($M_{Ab}$+2D), 151314.1 ($M_{Ab}$+3D). The toxin: antibody ratio (DAR) was calculated by analysis, and the average value was y=1.7.

Example 14. Anti-c-Met Antibody Ab-10 Conjugated with Toxin MC-VC-PAB-MMAE

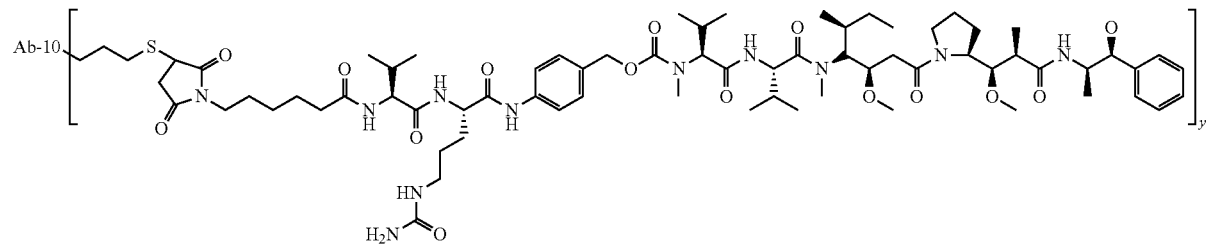

ADC-2

MC-VC-PAB-MMAE (1.6 mg, 1.2 μmol; prepared as method disclosed in PCT patent WO2004010957) was dissolved in 0.3 ml acetonitrile and was added to 3.0 ml of Ab-10 monoclonal antibody-propyl mercaptan 1 c solution (6.17 mg/ml) with shaking for 4 hours at 25° C., and then desalination and purification were done on a Sephadex G25 gel column (Elution phase: 0.05M of PBS solution which pH is 6.5). The PBS buffer solution of captioned product ADC-2 (3.6 mg/ml, 4.8 ml) was obtained by filtration through a 0.2 μm filter under aseptic conditions, and then stored at 4° C.

Q-TOF LC/MS: characteristic peak: 148118.4 ($M_{Ab}$+0D), 149509.2 ($M_{Ab}$+1D), 150903.1 ($M_{Ab}$+2D), 152290.4 ($M_{Ab}$+3D), 153680.7 ($M_{Ab}$+4D). The toxin: antibody ratio (DAR) was calculated by analysis, and the average value was y=1.8.

Example 15. Anti-c-Met Antibody Ab-10 Conjugated with Toxin MC-VC-PAB-MMAF

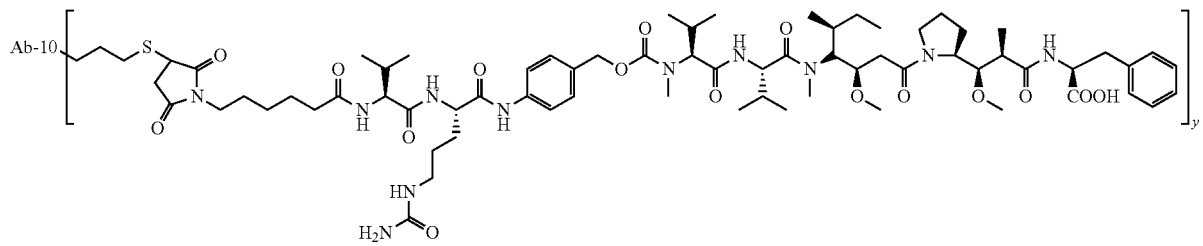

ADC-3

MC-VC-PAB-MMAF (1.6 mg, 1.2 µmol; prepared as method disclosed in PCT patent WO2005081711) was dissolved in 0.3 ml acetonitrile and was added to 3.0 ml Ab-10 monoclonal antibody-propyl mercaptan 1 c solution (6.17 mg/ml) with shaking for 4 hours at 25° C., and then desalination and purification were done on a Sephadex G25 gel column (Elution phase: 0.05M of PBS solution which pH is 6.5). The PBS buffer solution of captioned product ADC-3 (3.5 mg/ml, 4.9 ml) was obtained by filtration through a 0.2 µm filter under aseptic condition, and then stored at 4° C.

Q-TOF LC/MS: characteristic peak: 148119.1 ($M_{Ab}$+0D), 149525.3 ($M_{Ab}$+1D), 150930.7 ($M_{Ab}$+2D), 152335.2 ($M_{Ab}$+3D), 153739.8 ($M_{Ab}$+4D). The toxin: antibody ratio (DAR) was calculated by analysis, and the average value was y=1.6.

Example 16. Anti-c-Met Antibody Ab-10 Conjugated with Toxin MC-MMAE

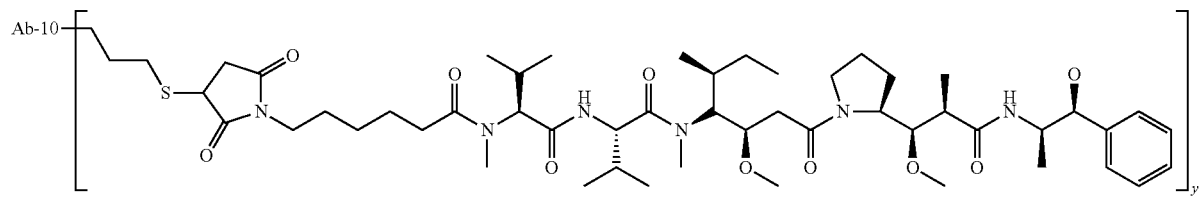

ADC-4

MC-MMAE (1.2 mg, 1.2 µmol; prepared as method disclosed in patent application US7/750/116B1) was dissolved in 0.3 ml acetonitrile and was added to 3.0 ml Ab-10 monoclonal antibody-propyl mercaptan 1 c solution (6.17 mg/ml) with shaking for 4 hours at 25° C., and then desalination and purification were done on a Sephadex G25 gel column (Elution phase: 0.05M of PBS solution which pH is 6.5). The PBS buffer solution of captioned product ADC-4 (3.4 mg/ml, 5.0 ml) was obtained by filtration through a 0.2 µm filter under aseptic condition, and then stored at 4° C.

Q-TOF LC/MS: characteristic peak: 148118.6($M_{Ab}$+0D), 149104.3($M_{Ab}$+1D), 150090.1($M_{Ab}$+2D), 151075.8($M_{Ab}$+3D). The toxin: antibody ratio (DAR) was calculated by analysis, and the average value was y=1.6.

Example 17. Anti-c-Met Antibody Ab-9 Conjugated with Toxin MC-MMAE

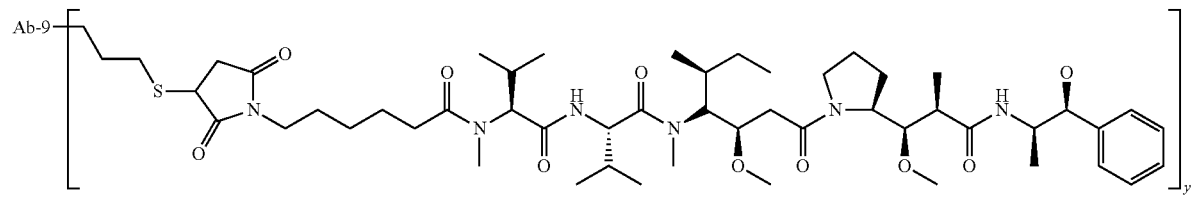

ADC-5

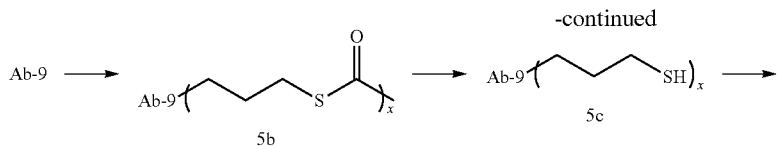

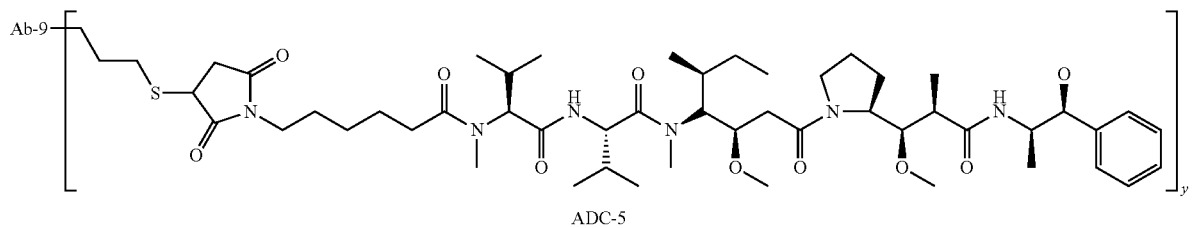

ADC-5

Step 1. Thioacetic acid S-(3-carbonyl propyl) ester (0.7 mg, 5.3 μmol) was dissolved in 0.9 mL acetonitrile solution. The acetonitrile solution of thio acetic acid S-(3-carbonyl propyl) ester prepared above was added into acetic acid/sodium acetate buffer (10.85 mg/ml, 9.0 ml, 0.976 mmol) containing Ab-9 monoclonal antibody, and 1.0 mL sodium borohydride aqueous solution (14.1 mg, 224 μmol) was added with shaking for 2 hours at 25° C. At the end of the reaction, desalination and purification were done on a Sephadex G25 gel column (Elution phase: 0.05M of PBS solution which pH is 6.5), and the product 5b solution was collected and concentrated to 10 mg/ml directly for the next reaction.

Step 2. 0.35 ml 2.0M of hydroxylamine hydrochloride solution was added into 11.0 mL of 5b solution with shaking for 30 minutes at 25° C., and then desalination and purification were done on a Sephadex G25 gel column (Elution phase: 0.05M of PBS solution which pH is 6.5), and the captioned product Ab-9 monoclonal antibody-propyl mercaptan 5c solution was collected (6.2 mg/ml, 15.0 mL).

Step 3. MC-MMAE (1.1 mg, 1.2 μmol) was dissolved in 0.3 ml acetonitrile and was added to 3.0 ml Ab-9 monoclonal antibody-propyl mercaptan 5c solution (6.2 mg/ml) with shaking for 4 hours at 25° C., and then desalination and purification were done on a Sephadex G25 gel column (Elution phase: 0.05M of PBS solution which pH is 6.5). The PBS buffer solution of captioned product ADC-5 (3.8 mg/ml, 4.6 ml) was obtained by filtration through a 0.2 μm filter under aseptic condition, and then stored at 4° C.

Q-TOF LC/MS: characteristic peak: 150530.9($M_{Ab}$+0D), 151915.7($M_{Ab}$+1D), 153333.6($M_{Ab}$+2D), 154763.4($M_{Ab}$+3D), 156271.9($M_{Ab}$+4D). The toxin: antibody ratio (DAR) was calculated by analysis, and the average value was y=1.5.

Example 18. Anti-c-Met Antibody Ab-9 Conjugated with Toxin MC-MMAF

ADC-6

MC-MMAF (1.1 mg, 1.2 μmol) was dissolved in 0.3 ml acetonitrile and was added to 3.0 ml Ab-9 monoclonal antibody-propyl mercaptan 5c solution (6.17 mg/ml) with shaking for 4 hours at 25° C., and then desalination and purification were done on a Sephadex G25 gel column (Elution phase: 0.05M of PBS solution which pH is 6.5). The PBS buffer solution of captioned product ADC-6 (3.8 mg/ml, 4.6 ml) was obtained by filtration through a 0.2 μm filter under aseptic condition, and then stored at 4° C.

Q-TOF LC/MS: characteristic peak: 150537.8($M_{Ab}$+0D), 152087.9($M_{Ab}$+1D), 153486.5($M_{Ab}$+2D), 154911.7($M_{Ab}$+3D), 156499.9($M_{Ab}$+4D). The toxin: antibody ratio (DAR) was calculated by analysis, and the average value was y=1.7.

Example 19. Anti-c-Met Antibody Ab-9 Conjugated with Toxin MC-VC-PAB-MMAF

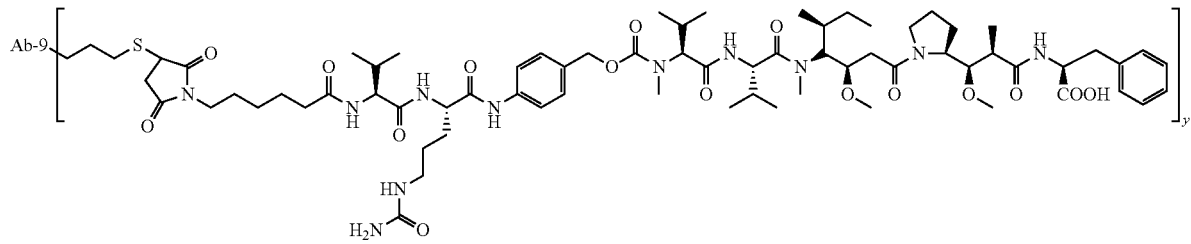

ADC-7

MC-VC-PAB-MMAF (1.6 mg, 1.2 μmol) was dissolved in 0.3 ml acetonitrile and was added to 3.0 ml Ab-9 monoclonal antibody-propyl mercaptan 5c solution (6.2 mg/ml) with shaking for 4 hours at 25° C., and then desalination and purification were done on a Sephadex G25 gel column (Elution phase: 0.05M of PBS solution which pH is 6.5). The PBS buffer solution of captioned product ADC-7 (3.8 mg/ml, 4.6 ml) was obtained by filtration through a 0.2 μm filter under aseptic condition, and then stored at 4° C.

Q-TOF LC/MS: characteristic peak: 150537.8($M_{Ab}$+0D), 152087.9($M_{Ab}$+1D), 153486.5($M_{Ab}$+2D), 154911.7($M_{Ab}$+3D), 156499.9($M_{Ab}$+4D). The toxin: antibody ratio (DAR) was calculated by analysis, and the average value was y=1.8.

Example 20. Anti-c-Met Antibody Ab-9 Conjugated with Toxin MC-VC-PAB-MMAE

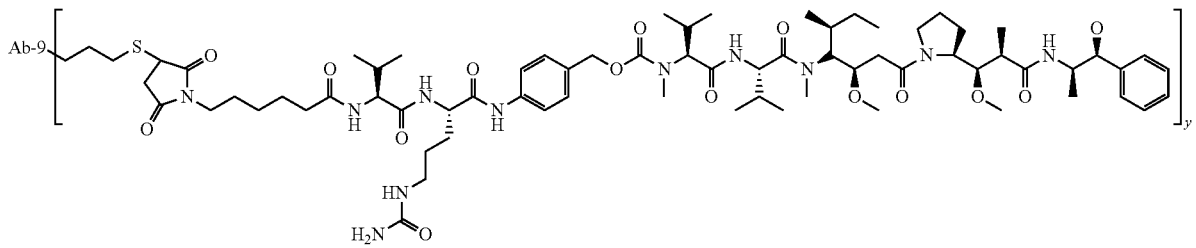

ADC-8

MC-VC-PAB-MMAE (1.6 mg, 1.2 μmol) was dissolved in 0.3 ml acetonitrile and was added to 3.0 ml Ab-9 monoclonal antibody-propyl mercaptan 5c solution (6.2 mg/ml) with shaking for 4 hours at 25° C., and then desalination and purification were done on a Sephadex G25 gel column (Elution phase: 0.05M of PBS solution which pH is 6.5). The PBS buffer solution of captioned product ADC-8 (3.8 mg/ml, 4.6 ml) was obtained by filtration through a 0.2 m filter under aseptic condition, and then stored at 4° C.

Q-TOF LC/MS: characteristic peak: 150508.6($M_{Ab}$+0D), 151903.6($M_{Ab}$+1D), 153314.5($M_{Ab}$+2D), 154747.8($M_{Ab}$+3D), 156039.5$M_{Ab}$+4D). The toxin: antibody ratio (DAR) was calculated by analysis, and the average value was y=1.6.

Example 21. Anti-c-Met Antibody Ab-10 Conjugated with Toxin SMCC-DMI

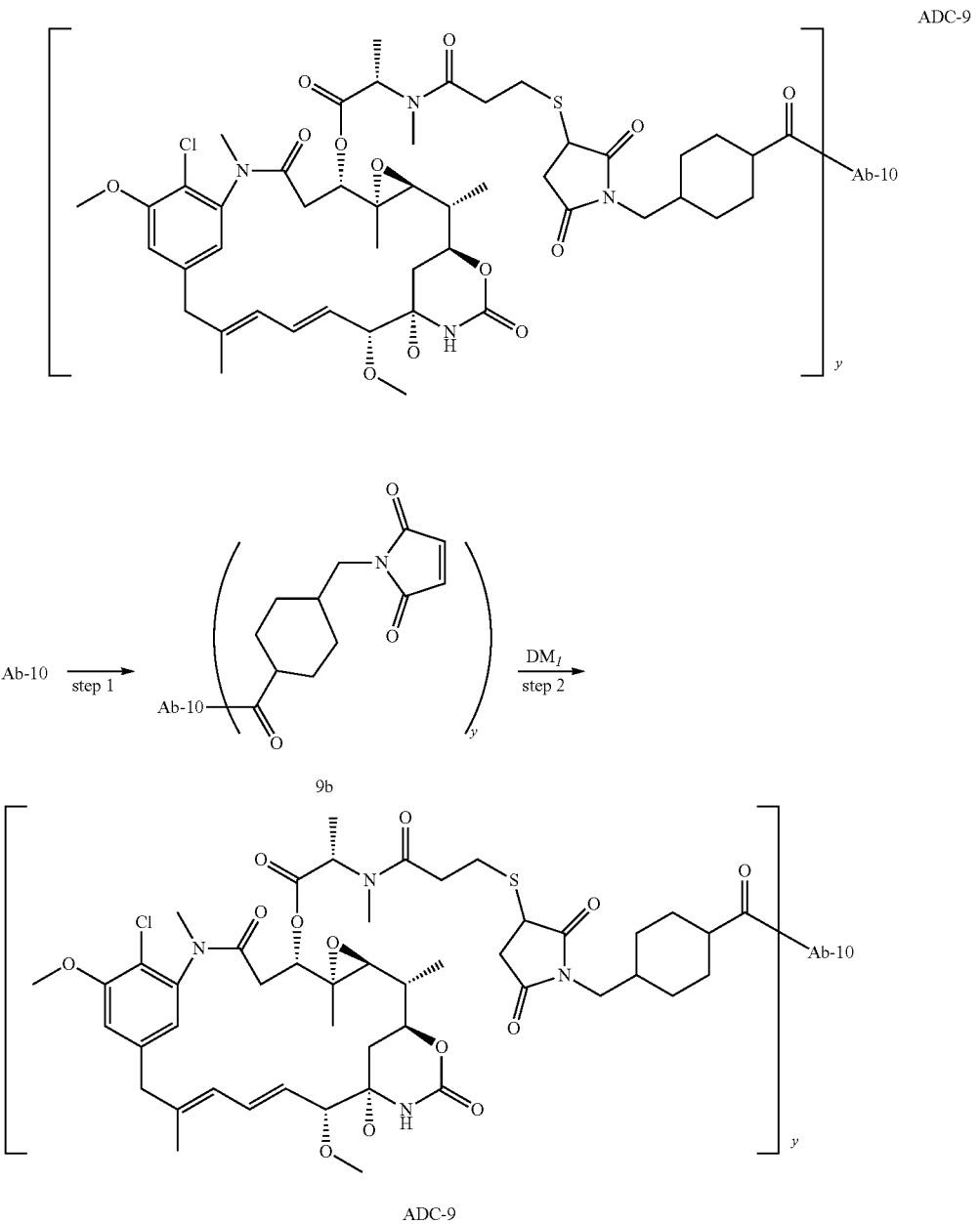

Step 1

SMCC (Succinimidyl 4-(N-Maleimidomethyl)cyclohexane-1-carboxylate; 1.65 mg, 4.94 μmol, purchased from Shanghai Hanhong Biochemical Company, Batch No. BH-4857-111203) was dissolved in 0.9 mL acetonitrile solution. The aceonitrile solution of SMCC prepared above was added into pH 6.5 PBS buffer (10.15 mg/ml, 9.0 mL, 0.62 μmol,) containing Ab-10 monoclonal antibody with shaking for 2 hours at 25° C. After the reaction, desalination and purification were done on a Sephadex G25 gel column (Elution phase: 0.05M of PBS solution which pH is 6.5), and the product 9b solution was collected and was concentrated to 10 mg/ml (8.3 mg/ml, 11 ml) for the next reaction.

Step 2

Ethanol solution of 3.0 mg L-DM1 (3.0 mg L-DM1/1.1 ml ethanol) (prepared by known methods published in *Journal of Medicinal Chemistry.* 2006, 49, 4392-4408) was added to 9b solution (11.0 ml) with shaking for 4 hours at 25° C., and then desalination and purification were done on a Sephadex G25 gel column (Elution phase: 0.05M of PBS solution which pH is 6.5). The product ADC-9 solution was collected (6.3 mg/ml, 14.0 mL) and stored at 4° C.

Q-TOF LC/MS: characteristic peak: 148119.6($M_{Ab}$+0D), 149078.1($M_{Ab}$+1D), 149836.4 ($M_{Ab}$+2D), 150593.7($M_{Ab}$+3D), 151552.5($M_{Ab}$+4D).

The average value was y=2.3.

Example 22. Anti-c-Met Antibody Ab-9 Conjugated with Toxin SMCC-DM1
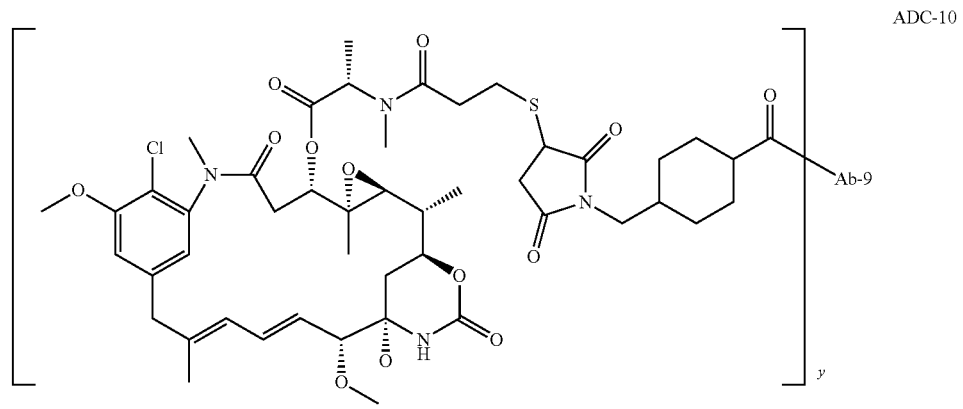
ADC-10
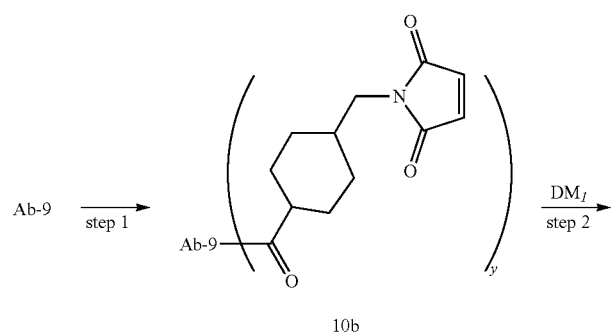
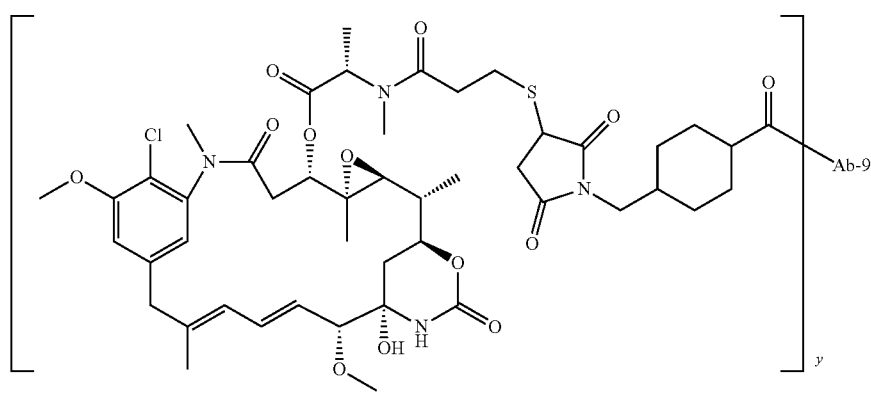
ADC-10

Step 1

SMCC (Succinimidyl 4-(N-Maleimidomethyl)cyclohexane-1-carboxylate; 1.65 mg, 4.94 μmol) was dissolved in 0.9 mL acetonitrile solution. The aceonitrile solution of SMCC prepared above was added into pH 6.5 PBS buffer (10.15 mg/ml, 9.0 mL, 0.62 μmol,) containing Ab-9 monoclonal antibody with shaking for 2 hours at 25° C. After the reaction, desalination and purification were done on a Sephadex G25 gel column (Elution phase: 0.05M of PBS solution which pH is 6.5), and the product 10b solution was collected and was concentrated to 10 mg/ml (8.3 mg/ml, 11 ml) for the next reaction.

Step 2

Ethanol solution of 3.0 mg L-DM1 (3.0 mg L-DM1/1.1 ml ethanol) was added to 9b solution (11.0 ml) with shaking for 4 hours at 25° C., and then desalination and purification were done on a Sephadex G25 gel column (Elution phase: 0.05M of PBS solution which pH is 6.5). The product ADC-10 solution was collected (6.3 mg/ml, 14.0 mL) and stored at 4° C.

Q-TOF LC/MS: characteristic peak: 150534.2($M_{Ab}$+0D), 151492.6($M_{Ab}$+1D), 152451.7($M_{Ab}$+2D), 153409.7($M_{Ab}$+3D), 154368.1($M_{Ab}$+4D).

The average value was y=2.2.

Example 23. Anti-c-Met Antibody Ab-9 Conjugated with Toxin SN-38

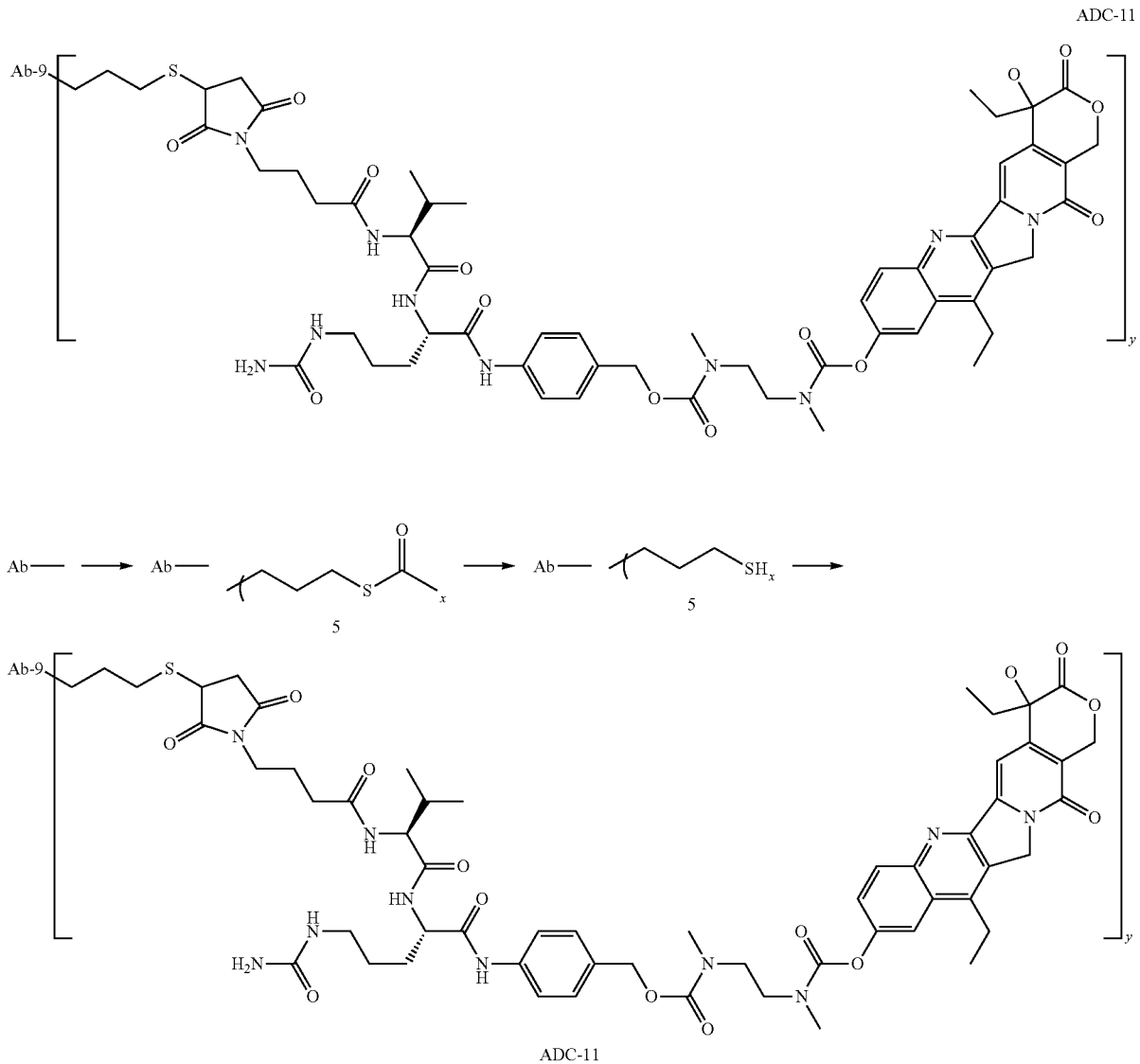

ADC-11

MC-VC-PAB-SN-38 (1.3 mg, 1.2 μmol) was dissolved in 0.3 ml acetonitrile and was added to 3.0 ml Ab-9 monoclonal antibody-propyl mercaptan 5c solution (6.2 mg/ml) with shaking for 4 hours at 25° C., and then desalination and purification were done on a Sephadex G25 gel column (Elution phase: 0.05M of PBS solution which pH is 6.5). The PBS buffer solution of captioned product ADC-11 (3.7 mg/ml, 4.5 ml) was obtained by filtration through a 0.2 μm filter under aseptic condition, and then stored at 4° C.

Q-TOF LC/MS: characteristic peak: 150537.1($M_{Ab}$+0D), 151786.6($M_{Ab}$+1D), 152948.6($M_{Ab}$+2D), 154161.7($M_{Ab}$+3D), 155365.9($M_{Ab}$+4D), 156477.8($M_{Ab}$+5D).

The average value was y=2.6.

Example 24. Anti-c-Met Antibody Ab-10 Conjugated with Toxin
1. Preparation of Toxin
(S)-2-((2R,3R)-3-((1S,3S,5S)-2-((3R,4S,5S)-4-((S)—N,3-dimethyl-2-((S)-3-methyl-2-(methyl amino) butyramide) butyramide)-3-methoxy-5-methylheptanoyl)-2-azabicyclo[3.1.0]hexane-3-yl)-3-methoxy-2-methylpropanamido)-3-(2-fluorophenyl)propionic acid
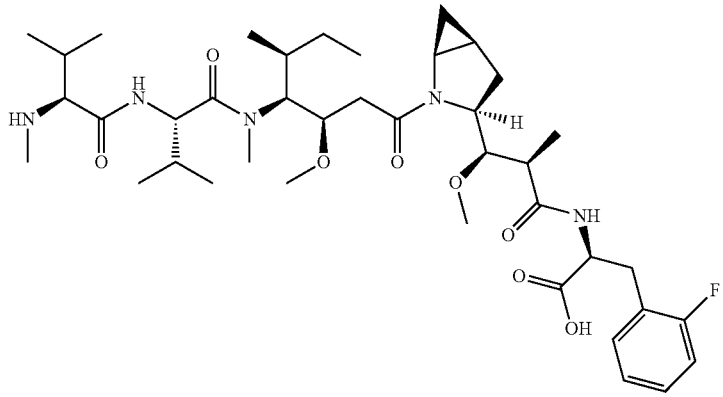
12g
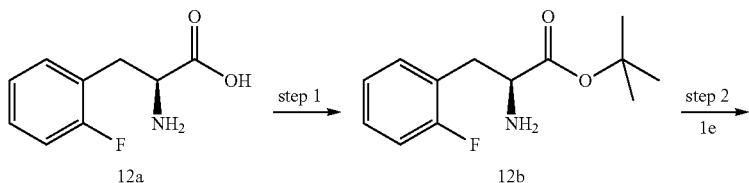
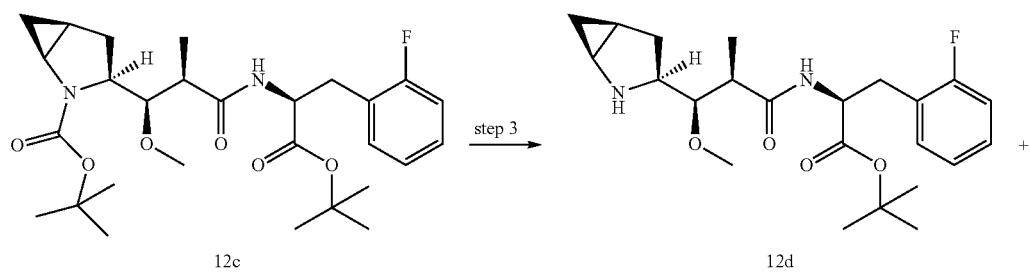
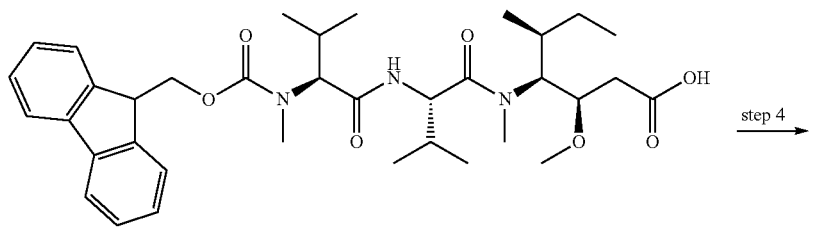

-continued

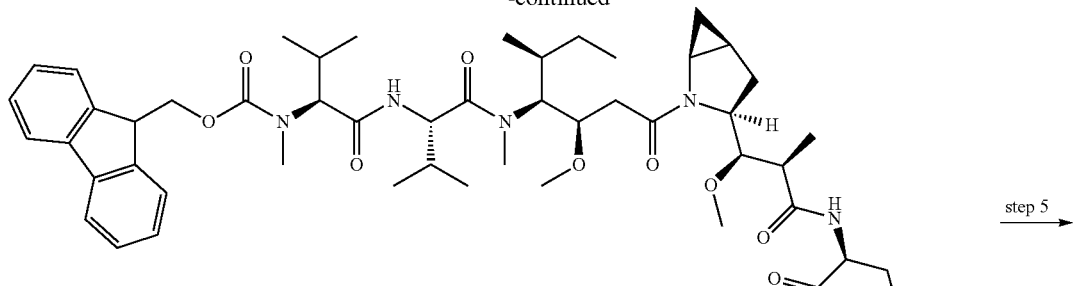

12e

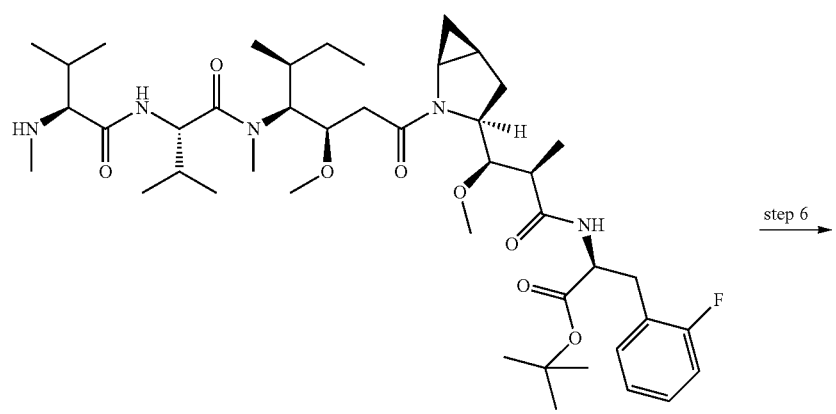

12f

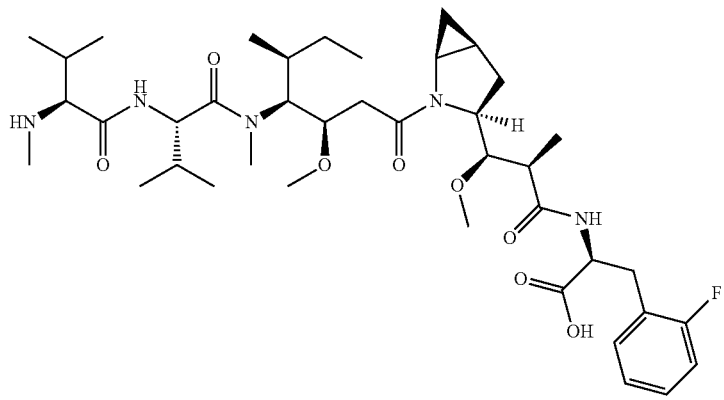

12g

Step 1. (S)-tert-butyl-2-amino-3-(2-fluorophenyl)propanoic acid (S)-2-amino-3-(2-fluorophenyl)propanoic acid 12a (400 mg, 2.18 mmol, prepared according to the known method in "*Advanced Synthesis & Catalysis,* 2012, 354(17), 3327-3332") was dissolved in 10 mL of tert-butyl acetate. Perchloric acid (300 mg (70%), 3.3 mmol) was added and stirred at room temperature for 16 hours. 6 ml of water was added after the reaction, and the solution was separated. The organic phase was washed with saturated sodium bicarbonate solution (5 ml). The aqueous phase was adjusted to pH=8 with saturated sodium bicarbonate solution, and was then extracted with dichloromethane (5 ml×3), and combined with the organic phase. The reaction mixture was washed successively with water (3 ml) and saturated sodium chloride solution (5 ml), dried with anhydrous sodium sulfate, filtered, and the filtrate was concentrated under reduced pressure. The crude product (S)-tert-butyl 2-amino-3-(2-fluorophenyl) propanoic acid 12b was obtained (390 mg, yellow, oily) and was subjected to the next reaction directly without purification.

Step 2.

(1S,3S,5S)-tert-butyl 3-((1R,2R)-3(((S)-1-(t-butoxy)-3-(2-fluorophenyl)-1-carbonylpropyl-2-)amino)-1-methoxy-2-methyl-3-carbonyl propyl)-2-azabicyclo [3.1.0] hexane-2-carboxylic acid (2R,3R)-3-((1S,3S,5S)-2-(tert-butoxycarbonyl)-2-azabicyclo[3.1.0]hexane-3-yl)-3-methoxy-2-methyl propionate 12e (100 mg, 0.334 mmol) was dissolved in 6 ml of the mixture of dichloromethane and dimethylformamide (V/V=5:1), and crude product (S)-tert-butyl 2-amino-3-(2-fluorophenyl) propionate 12b (80 mg, 0.334 mmol) was added. N,N-diisopropylethylamine (0.29 ml, 1.67 mmol) and 2-(7-Azabenzotriazol)-N,N,N',N'-tetramethyluronium hexafluorophosphate (152.3 mg, 0.40 mmol) were added to the mixture. The mixture was stirred for 1 hour under argon atmosphere at room temperature. After the reaction, 10 ml water was added and stirred. The layer of dichloromethane was washed by saturated sodium chloride solution (10 ml), dried with anhydrous sodium sulfate, and filtered, and the filtrate was concentrated under reduced pressure. The residues were purified by silica gel column chromatography using eluent system B to obtain the captioned product of (1S,3S,5S)-tert-butyl-3-((1R,2R)-3-(((S)-1-(t-butoxy)-3(2-fluorophenyl)-1-carbonylpropyl-2-yl)amino)-1-methoxy-2-methyl-3-carbonyl propyl)-2-azabicyclo[3.1.0] hexane-2-carboxylic acid 12c (173 mg, clear liquid). The yield was 99.5%.

MS m/z (ESI): 521.2 [M+1]

Step 3.

(S)-tert-butyl-2-((2R,3R)-3-((1S,3S,5S),-2-azabicyclo[3.1.0]hexane-3-yl)-3-meth oxy-2-methylpropionamide)-3-(2-fluorophenyl) propionic acid (1S,3S,5S)-tert-butyl-3-((1R,2R)-3-(((S)-1-(t-butoxy)-3 (2-fluorophenyl)-1-carbonylpropyl-2-yl)amino)-1-methoxy-2-methyl-3-carbonyl propyl)-2-azabicyclo[3.1.0] hexane-2-carboxylic acid 12c (173 mg, 0.33 mmol) was dissolved in 2 ml dioxane, and 5.6M hydrogen chloride dioxane solution (0.21 ml, 1.16 mmol) was added. The mixture was stirred for 1 hour under argon atmosphere at room temperature, and was placed in a 0° C. refrigerator for 12 hours. After the reaction, the reaction mixture was concentrated under reduced pressure, and 5 ml dichloromethane was added to dilute the reaction mixture. 10 ml saturated sodium bicarbonate solution was added, and the mixture was stirred for 10 minutes. The product was separated, and the aqueous phase was extracted by dichloromethane (5 ml×3). The dichloromethane layer was combined and was washed by saturated sodium chloride solution (10 ml), dried with anhydrous sodium sulfate, and filtered. The filtrate was concentrated under reduced pressure.

The crude product (S)-tert-butyl-2-((2R,3R)-3-((1S,2S,5S)-2-azabicyclo[3.1.0]hexane-3-yl)-3-methoxy-2-methylpropionamide)-3-(2-fluorophenyl) propionic acid 12d (77 mg, yellow liquid) was obtained and directly subjected to the next reaction without purification.

MS m/z (ESI):421.2 [M+1]

Step 4.

(S)-tert-butyl-2-((2R,3R)-3-((1S,3S,5S)-2-((5S,8S,11S,12R)-11-((S)-secbutly)-1-(9H-fluorene-9-yl)-5,8-diisopropyl-12-methoxy-4,10-dimethyl-3,6,9-tricarbonyl-2-oxygen-4,7,10-triazatetradecyl-14-acyl)-2-azabicyclo[3.1.0]hexane-3-yl)-3-methoxy-2-methylpropane amide)-3-(2-fluorophenyl) propionic acid Crude product (S)-tert-butyl-2-((2R,3R)-3-((1S,2S,5S)-2-azabicyclo[3.1.0]hexane-3-yl)-3-methoxy-2-methylpropionamide)-3-(2-fluorophenyl) propionic acid 12d (77 mg, 0.183 mmol) and (5S,8S,11S,12R)-11-((S)-secbutly)-1-(9H-fluorene-9-yl)-5,8-diisopropyl-12-methoxy-4,10-dimethyl-3,6,9-tricarbonyl-2-oxo-4,7,10-triazatetradecyl-14-carboxylic acid 12i (116.8 mg, 0.183 mmol, prepared by methods published in patent application "WO 2013072813") were dissolved in a 6 ml mixture of dichloromethane and dimethylformamide (V/V=5:1). N,N-diisopropylethylamine (0.16 ml, 0.915 mmol) and 2-(7-Azabenzotriazol)-N,N,N',N'-tetramethyluronium hexafluorophosphate (84 mg, 0.22 mmol) were added into that mixture. The reaction mixture was stirred for 1 hour under argon atmosphere at room temperature. After the reaction, 10 ml water was added and stirred. The layer of dichloromethane was washed by saturated sodium chloride solution (10 ml), dried with anhydrous sodium sulfate, and filtered, and the filtrate was concentrated under reduced pressure. The residues were purified by silica gel column chromatography using eluent system B to obtain the captioned product of (S)-tert-butyl-2-((2R,3R)-3-((1S,3S,5S)-2-((5S,8S,11S,12R)-11-((S)-secbutly)-1-(9H-fluorene-9-yl)-5,8-diisopropyl-12-methoxy-4,10-dimethyl-3,6,9-tricarbonayl-2-oxo-4,7,10-triazatetradecyl-14-acyl)-2-azabicyclo[3.1.0]hexane-3-yl)-3-methoxy-2-methylpropionamide)-3-(2-fluorophenyl) propionic acid 12e (190.5 mg, yellow viscous) with yield of 100%.

MS m/z (ESI): 1040.6 [M+1]

Step 5.

(S)-tert-butyl-2-((2R,3R)-3-((1S,3S,5S)-2-((3R,4S,5S)-4-((S)—N,3-dimethyl-2-((S)-3-methyl-2-(methylamino)butanamide)-3-methoxy-5-methylheptanoyl)-2-azabicyclo[3.1.0]hexane-3-yl)-3-methoxy-2-methylpropanamido)-3-(2-fluorophenyl) propionic acid (S)-tert-butyl-2-((2R,3R)-3-((1S,3S,5S)-2-((5S,8S,11S,12R)-11-((S)-secbutly)-1-(9H-fluorene-9-yl)-5,8-diisopropyl-12-methoxy-4,10-dimethyl-3,6,9-tricarbonayl-2-oxo-4,7,10-triazatetradecyl-14-acyl)-2-azabicyclo[3.1.0]hexane-3-yl)-3-methoxy-2-methyl propionamide)-3-(2-fluorophenyl) propionic acid 12e (190.5 mg, 0.183 mmol) was dissolved in 1.5 ml dichloromethane and 2 ml diethylamine was added. The mixture was stirred for 3 hours under argon atmosphere at room temperature. After the reaction, the reaction mixture was concentrated under reduced pressure and the crude captioned product (S)-tert-butyl-2-((2R,3R)-3-((1S,3S,5S)-2-((3R,4S,5S)-4-((S)—N,3-dimethyl-2-((S)-3-methyl-2-(methylamino)butanamide)butanamide)-3-methoxy-5-methylheptanoyl)-2-azabicyclo[3.1.0]hexane-3-yl)-3-methoxy-2-methylpropanamido)-3-(2-fluorophenyl) propionic acid 12f (150 mg, yellow viscous) was obtained. Products were directly subjected to the next reaction without purification.

MS m/z (ESI): 818.5 [M+1]

Step 6.

(S)-2-((2R,3R)-3-((1S,3S,5S)-2-((3R,4S,5S)-4-((S)—N,3-dimethyl-2-((S)-3-methyl-2-(m ethylamino)butanamide)butanamide)-3-methoxy-5-methylheptanoyl)-2-azabicyclo[3.10]hexane-3-yl)-3-methoxy-2-methylpropanamido)-3-(2-fluorophenyl)propionic acid The crude product (S)-tert-butyl-2-((2R,3R)-3-((1S,3S,5S)-2-((3R,4S,5S)-4-((S)—N,3-dimethyl-2-((S)-3-methyl-2-(methylamino)butanamide)butanamide)-3-methoxy-5-methylheptanoyl)-2-azabicyclo[3.1.0]hexane-3-yl)-3-methoxy-2-methylpropanamido)-3-(2-fluorophenyl)propionic acid 12f (150 mg, 0.183 mmol) was dissolved in 1 ml dioxane and 3 ml of 5.6M hydrogen chloride dioxane. The mixture was stirred for 12 hours under argon atmosphere at room temperature. After the reaction, the reaction solution was concentrated under reduced pressure with ether solvent. The residues were purified by high performance liquid chromatography to obtain the captioned product (S)-2-((2R,3R)-3-((1S,3S,5S)-2-((3R,4S,5S)-4-((S)—N,3-dimethyl-2-((S)-3-methyl-2-(methylamino)butanamide)butanamide)-3-methoxy-5-methylheptanoyl)-2-azabicyclo[3.1.0]hexane-3-yl)-3-methoxy-2- methylpropanamido)-3-(2-fluorophenyl) propionic acid 12 g (28 mg, white powder) with yield of 20%.

MS m/z (ESI): 762.7[M+1]

methyl hexanamide)-3-methyl butanamide)-N,3-dimethyl butanamide)-3-methoxy-5-methylheptanoyl)-2-azabicyclo[3.1.0]hexane-3-yl)-3-methoxy-2-methylpropanamido)-3-(2-fluorophenyl)propionic acid

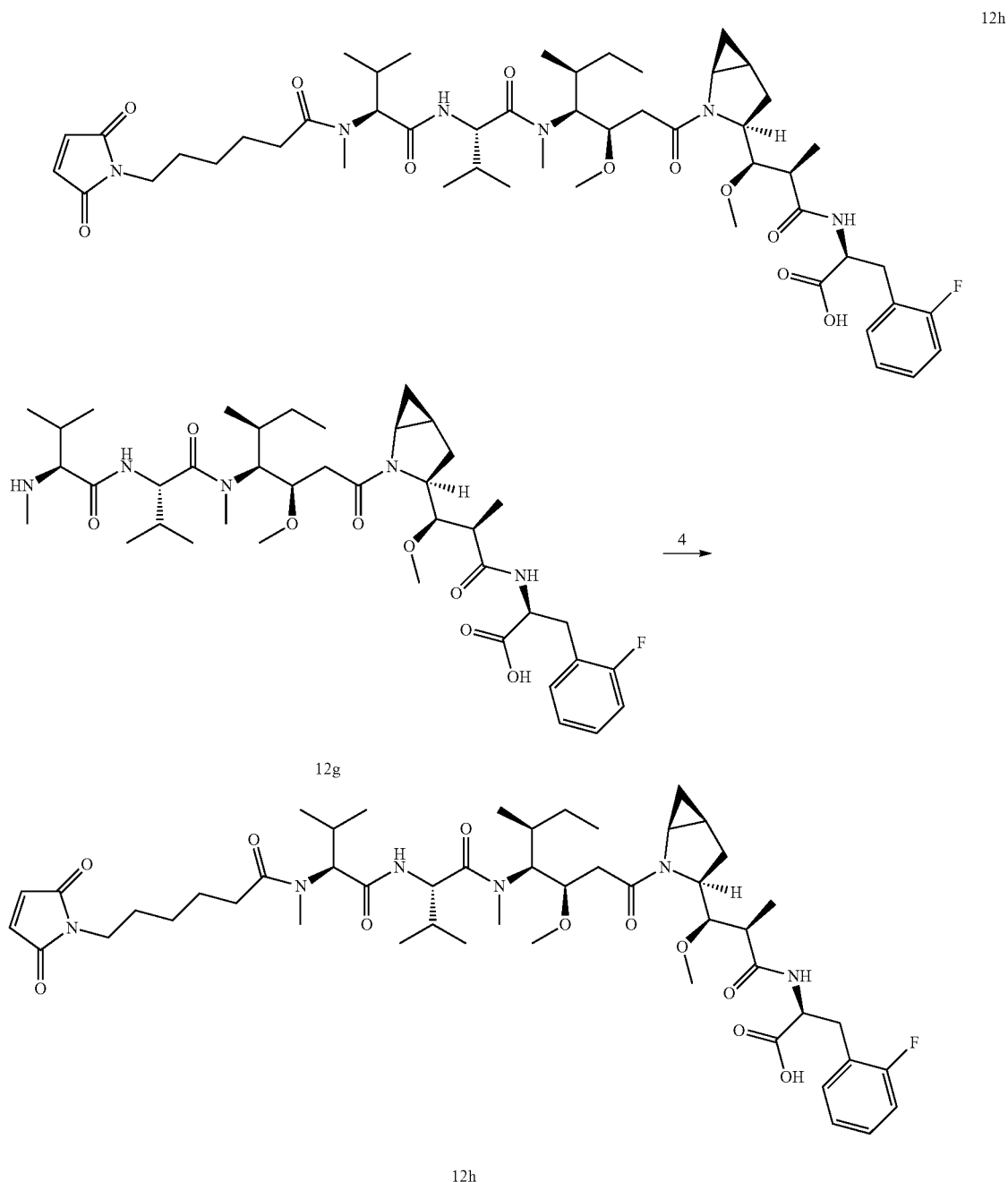

¹H NMR (400 MHz, CD₃OD): δ 7.38-7.18 (m, 2H), 7.13-7.01 (m, 2H), 4.80-4.67 (m, 2H), 4.30-4.15 (m, 1H), 4.13-4.01 (m, 1H), 3.96-3.83 (m, 2H), 3.75-3.60 (m. 2H), 3.42-3.11 (m, 9H), 3.06-2.95 (m, 1H), 2.70-2.58 (m, 4H), 2.28-2.01 (m, 4H), 1.88-1.70 (m, 3H), 1.57-1.25 (m, 41H), 1.22-0.95 (m, 18H), 0.92-0.80 (m, 4H), 0.78-0.65 (m, 1H).

2. Preparation of Toxin Intermediates (S)-2-((2R,3R)-3-((1S,3S,5S)-2-((3R,4S,5S)-4-((S)-2-((S)-2-(6-(2,5-dicarbonyl-2,5-dihydro-1H-pyrrol-1-yl)-N-(S)-2-((2R,3R)-3-((1S,3S,5S)-2-((3R,4S,5S)-4-((S)—N,3-dimethyl-2-((S)-3-methyl-2-(methylamino)butanamide) butanamide)-3-methoxy-5-methylheptanoyl)-2-azabicyclo[3.1.0]hexane-3-yl)-3-methoxy-2-methylpropanamido)-3-(2-fluorophenyl)propionic acid 12 g (25 mg, 0.033 mmol) was dissolved in 3 ml dichloromethane and N,N-diisopropylethylamine (0.029 ml, 0.164 mmol) was added. The reaction system was under argon atmosphere, and the dichloromethane solution of 6-(2,5-dicarbonyl-2,5-dihydro- 1H-pyrrol-1-yl)hexanoyl chloride 4b (11.3 mg, 0.049 mmol) prepared above was added dropwise into the mixture in an ice-bath, and the reaction was performed for 3 hours at room temperature. After the reaction, 5 ml water was added, and the mixture was stirred for 20 minutes. The mixture was allowed to stand until layers formed, and the organic layer phase was dried with anhydrous sodium sulfate and filtered, and the filtrate was concentrated under reduced pressure. The residues were purified by high performance liquid chromatography to obtain the captioned product, (S)-2-((2R, 3R)-3-((1S,3S,5S)-2-((3R,4S,5S)-4-((S)-2-((S)-2-(6-(2,5-dicarbonyl-2,5-dihydro-1H-pyrrol-1-yl)-N-methyl hexanamide)-3-methyl butanamide)-N,3-dimethyl butanamide)-3-methoxy-5-methylheptanoyl)-2-azabicyclo[3.1.0]hexane-3-yl)-3-meth oxy-2-methylpropanamido)-3-(2-fluorophenyl) propionic acid 12h (7 mg, yellow viscous). The yield was 22.4%.

MS m/z (ESI): 955.4 [M+1]

$^1$H NMR (400 MHz, CD$_3$OD): δ 7.36-7.30 (m, 1H), 7.29-7.21 (m, 1H), 7.17-7.02 (m, 2H), 6.83-6.79 (m, 2H), 4.81-4.71 (m, 2H), 4.69-4.55 (m, 2H), 4.25-4.15 (m, 1H), 4.13-4.04 (m, 1H), 3.96-3.85 (m, 2H), 3.70-3.61 (m, 1H), 3.55-3.46 (m, 3H), 3.40-3.21 (m, 4H), 3.18-3.10 (m, 2H), 3.07-2.96 (m, 4H), 2.67-2.56 (m, 2H), 2.54-2.34 (m, 3H), 2.29-2.17 (m, 2H), 2.10-1.99 (m, 1H), 1.89-1.57 (m, 7H), 1.52-1.28 (m, 6H), 1.21-1.11 (m, 4H), 1.07-0.96 (m, 6H), 0.95-0.81 (m, 12H), 0.80-0.69 (m, 1H).

3. Preparation of Antibody-Toxin Conjugate

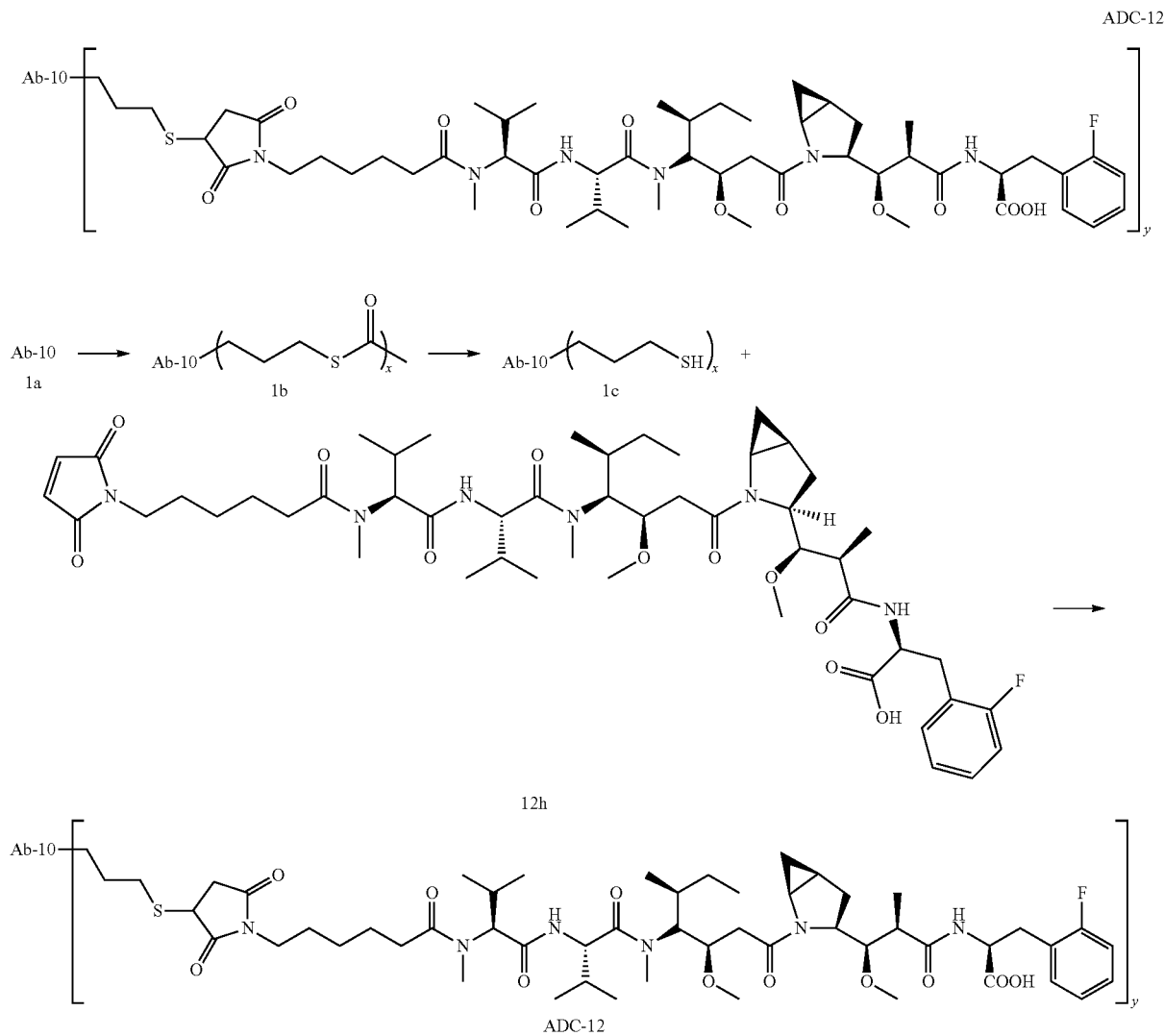

Compound 12h (1.2 mg, 1.2 µmol) was dissolved in 0.3 ml acetonitrile. Ab-10 monoclonal antibody-propylmercaptan 1c solution (6.17 mg/ml) was added with shaking for 4 hours at 25° C., and then desalination and purification were done on a Sephadex G25 gel column (Elution phase: 0.05M of PBS solution which pH is 6.5). The PBS buffer solution of captioned product ADC-12 (3.3 mg/ml, 5.0 ml) was obtained by filtration through a 0.2 µm filter under aseptic condition, and then stored at 4° C.

Q-TOF LC/MS: characteristic peak: 148119.6($M_{Ab}$+0D), 149150.5 ($M_{Ab}$+1D), 150221.1 ($M_{Ab}$+2D), 151265.1 ($M_{Ab}$+3D), 152314.3($M_{Ab}$+4D).

The average value was: y=1.6.

Referring to examples 13-24, ADC compounds of examples 25-27 were prepared.

Example 25

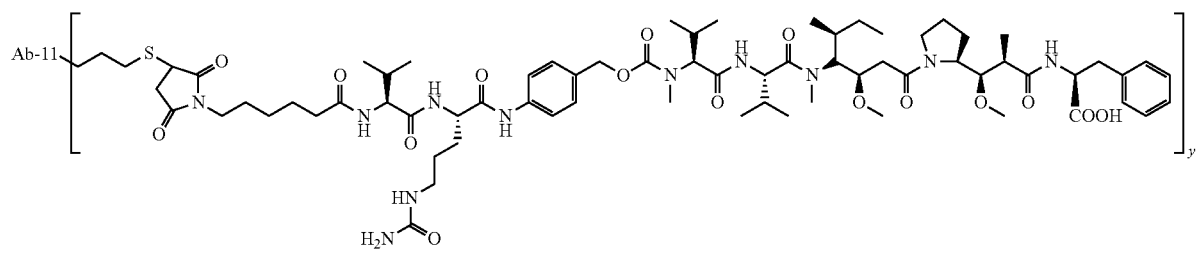

Anti-c-Met antibody Ab-11 conjugated toxin MC-VC-PAB-MMAF

Example 26

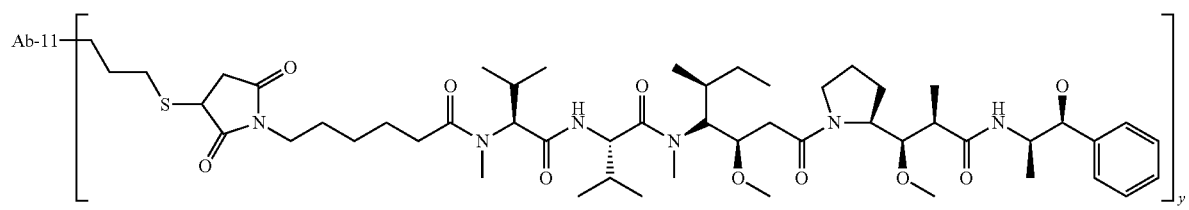

Anti-c-Met antibody Ab-11 conjugated toxin MC-MMAE

Example 27

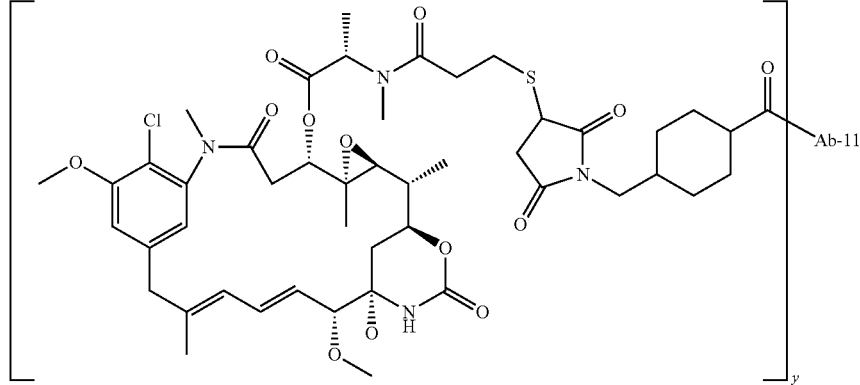

Anti-c-Met antibody Ab-11 conjugated toxin SMCC-DM1

Test Examples of Anti-c-Met Antibody-Toxin Conjugate (ADC) Molecules

Test Example 1. Stability Evaluation of Anti-c-Met Antibody Toxin Conjugate (ADC) Molecules The toxin intermediates and toxins of the ADC molecules of the invention or other c-Met antibody-toxin conjugates (e.g., LY-2875358-ADC) with endocytosis were evaluated for the stability of free toxins in PBS and in human and monkey plasma.

The toxin intermediates and toxins of the example compounds ADC-1 and ADC-12 were diluted to 500 μg/mL with PBS, or human or monkey plasma (Suzhou Xishan Zhongke Pharmaceutical Research and Development Co., Ltd., animal production license number: SCXK (Su) 2012-0009), samples were incubated at 37° C. for 7 days, and concentrations of free toxins and toxin intermediates were measured at days 0, 3, and 7. 20 μl of internal control (camptothecin, Shanghai Ronghe Pharmaceutical Technology Development Co., Ltd., batch number 090107, 100 ng/ml) and 150 μl acetonitrile were added to 50 μl of human or monkey plasma or PBS sample containing drug, the samples were vortexed for 3 min and centrifuged at 15000 rpm for 10 min, 80 μL of the supernatant was taken and mixed with 80 μL of 0.2% formic acid, and then 10 μL of the sample was taken for injection. A standard curve method was performed as follows: 50 μl of blank human or monkey plasma or PBS sample was added into 50 μl of working solution, respectively; 20 μl of internal control (camptothecin, 100 ng/ml) and 100 μl acetonitrile were added, the samples were vortexed for 3 min and then centrifuged at 15000 rpm for 10 min; 80 μL of the supernatant was taken and mixed with 80 μL of 0.2% formic acid; 10 μL of the sample was taken for injection.

The Shimadzu LC-30AD ultra-high performance liquid chromatography system (Shimadzu Corporation), UPLC-MS/MS mass spectrometer API4000 triple quadrupole tandem mass spectrometer (AB SCIEX) were used, with the following chromatographic column condition settings:

Waters XBridge™ BEH300 C18 (100 mm×4.6 mm i.d., 3.5 mm), the mobile phase was 0.2% formic acid-acetonitrile (gradient elution). The results are shown in Table 11 and Table 12.

TABLE 11

Evaluation of plasma stability of toxin intermediates and toxin drugs of ADC-1 of the present invention

| Free toxin/ | MC-MMAF | | | MMAF | | |
|---|---|---|---|---|---|---|
| Solvent | Day 0 | Day 3 | Day 7 | Day 0 | Day 3 | Day 7 |
| PBS | 0.02* | 0.03 | 0.19 | ND | ND | ND |
| human plasma | ND | 0.05 | 0.1 | ND | ND | ND |
| Monkey plasma | ND | ND | ND | ND | ND | ND |

*The test value is the percentage of free toxins in the sample. 0.01-0.19% is within the range of detection background;
ND: Not detectable, undetectable.

TABLE 12

Evaluation of plasma stability of toxin intermediates and toxin drugs of ADC-12 of the present invention

| Free toxin/ | Toxin intermediates 12h | | | Toxin 12g | | |
|---|---|---|---|---|---|---|
| Solvent | Day 0 | Day 3 | Day 7 | Day 0 | Day 3 | Day 7 |
| PBS | ND | ND | ND | ND | ND | ND |
| human plasma | ND | ND | ND | ND | ND | ND |
| Monkey plasma | ND | ND | ND | ND | ND | ND |

ND: Not detectable, undetectable.

The above results show that the toxin intermediates and toxins of ADC-1 and ADC-12 in the present invention are stable in various solvents (PBS, human plasma, monkey plasma, etc.). No degradation products, free toxins or toxin intermediates (toxin-linker) were detected after incubation at 37° C. for 0 day, 3 days and 7 days.

Test Example 2. Evaluation of the Activity In Vitro of Anti-c-Met Antibody Toxin Conjugates (ADC)

The in vitro activity of ADC-1 and ADC-12 of the present invention was evaluated by FACS (detection of the binding activity with c-Met positive cells) and endocytosis (method see Example 11). The result is shown in Table 13.

TABLE 13

The in vitro activity of ADC molecules of the present invention

| Humanized antibody | MKN45/FCAS binding activity (nM) | Endocytosis of cell (%)* |
|---|---|---|
| Ab-10 | 1.01 | 32.7 |
| ADC-1 | 1.22 | 32.9 |
| ADC-12 | 0.48 | 31.8 |

*The data is expressed as the endocytosis ratio at 1 hour.

The above results show that antibodies of the invention conjugated to toxin still maintain the binding activity and endocytosis activity of the antibodies.

Test Example 3. Cytotoxicity Test of Anti-c-Met Antibody Toxin Conjugates (ADC)

In order to assess the toxic effects of the ADC molecules of the present invention on cells, the ATP toxicity test was performed. ATP is an indicator of the metabolism of living cells, and the detection of ATP can reflect the effect of the toxicity of molecules on cells.

HepG2 cells (Chinese Academy of Sciences cell bank, Cat # TCHu 72) were cultivated in EMEM complete medium containing 10% FBS, and MKN45 cells were cultivated in RPMI1640 complete medium containing 10% FBS. Trypsinization was performed for 2-3 min by adding 2-3 ml trypsin, 10-15 ml complete medium was added to elute the trypsinized cells when the trypsinization was complete, and the cells were centrifuged at 1000 rpm for 3 min. The supernatant was discarded, 10-20 ml complete medium was added to resuspend the cells to obtain a single cell suspension, and the cell density was adjusted to $4 \times 10^4$ cells/ml. 0.1 ml of the above cell suspension was added to each well of a 96-well cell culture plate and cultivated in an incubator at 37° C. in 5% $CO_2$. After 24 hours, the medium was removed, and 90 μl of EMEM medium containing 2% FBS or RPMI1640 medium containing 2% FBS was added to each well, the test sample (the compound and toxin of Example 13) was diluted with PBS to a gradient of different concentrations, 10 μl of the sample was added to each well, and the plate was incubated in a incubator at 37° C. in 5% $CO_2$ for 72 hours. Detection was performed according to the instructions of CellTiter-Glo® Luminescent Cell Viability Assay kit (Promega, Cat # G7571). The chemiluminescence was measured by a microplate reader (VICTOR 3, PerkinElmer), and the result was analyzed by GraphPad Prism (version 5.0) software. The result is shown in Table 14.

TABLE 14

Cytotoxicity of ADC molecules of the invention and corresponding free toxins

| Test sample | $IC_{50}$ (nM) in MKN45 cell | $IC_{50}$ (nM) in HepG2 cell |
|---|---|---|
| ADC-1 | 0.51 | ND |
| MMAF | 0.85 | 4.88 |
| ADC-12 | 0.59 | ND |
| 12 g | 79.4 | 400.8 |

ND: No activity was detected; NA: Not applicable.

Discussion: The above results show that the cytotoxicity of ADC-1 and ADC-12 to c-Met positive cells MKN45 is the same ($IC_{50}$ is 0.51 nM and 0.59 nM, respectively).

However, the cytotoxicity effect of each toxin moiety on c-Met positive cells was different, and there is a 93-fold difference between the toxin moieties of these two ADCs (79.4/0.85).

The ADC-1 and ADC-12 of the present invention have no cytotoxic effect on c-Met-negative HepG2 cells, indicating that the ADC compound has a specific targeting effect. However, the cytotoxicity effect of each toxin moiety on c-Met-negative HepG2 cells was different, and there is an 82-fold difference between the toxin moieties of these two ADCs (400.8/4.88).

These results show that ADC-1 and ADC-12 have a specific targeting effect and can inhibit the proliferation of c-Met positive cells without toxic effect on non-specific (normal cells) cells. The difference between ADC-1 and ADC-12 is that the toxicity of free toxins of ADC-1 and ADC 12 on target cells and that on non target cells is different. The cytotoxicity of the toxin moiety of ADC-12 on c-Met positive cells and negative HepG2 cells is 93-times and 82-times lower than that of ADC-1, respectively. Thus, when the molecule reaches the target cells, the non-specific toxic effect of ADC-12 is weaker than that of ADC-1, if free toxin is released. Therefore, the toxic side effect is smaller and the safety is good.

Test Example 4. Proliferation Inhibition Effect of an Anti-c-Met Antibody Toxin Conjugate (ADC) Molecule on Tumor Cells These results indicate that ADC-1 (example 13) can specifically kill tumor target cells expressing c-Met. In order to detect the proliferation inhibition of toxic effects on tumor cell, the molecules of the present invention were tested on a variety of tumor cells; the inhibitory effect of the sample on cell proliferation was measured by a CCK method, and the in vitro cell activity of an ADC molecule of the present invention was evaluated according to its $IC_{50}$ value.

The cells used and the corresponding medium are shown in Table 15 below. Cell proliferation was measured using the Cell Counting Kit (Dojindo chem Co. Cat # CK04) (according to the instructions).

Trypsinization was performed for 2-3 min by adding 2-3 ml trypsin, 10-15 ml complete medium was added to elute the trypsinized cells when the trypsinization was complete, and the cells were centrifuged at 1000 rpm for 3 min. The supernatant was discarded, 10-20 ml complete medium was added to resuspend the cells to obtain a single cell suspension, and the cell density was adjusted to $4 \times 10^4$ cells/ml. 0.1 ml of the above cell suspension was added to each well of a 96-well cell culture plate and cultivated in an incubator at 37° C. in 5% $CO_2$. After 24 hours, the medium was removed, and 90 µl of medium containing 2% FBS was added to each well. The test sample was diluted with PBS to a gradient of different concentrations, 10l of the sample was added to each well, and the plate was incubated in a incubator at 37° C. in 5% $CO_2$ for 72 hours. 10 µl of CCK8 was added to each well and incubated for 2 hours in an incubator. OD450 was detected by a microplate reader (VICTOR 3, PerkinElmer), and data was analyzed using GraphPad Prism (version 5.0) software. The results are shown in Table 16.

TABLE 15

Culture media used in this example

| Cell line | Medium | Manufacturer, No |
|---|---|---|
| MKN45 | RPMI1640 + 10% FBS | JCRB, JCRB0254 |
| SNU5 | IMDM + 10% FBS | ATCC, Cat# CRL-5973 ™ |
| BxPC3 | RPMI1640 + 10% FBS | Chinese Academy of Sciences cell bank (Cat# TCHu 12) |
| Caki-1 | McCOY's 5A + 10% FBS | Chinese Academy of Sciences cell bank, Cat# TCHu135 |
| NCI-H1993 | RPMI1640 + 10% FBS | ATCC, Cat# CRL-5909 ™ |
| PC9 | DMEM + 10% FBS | Shanghai bioleaf Biological Technology Co., Ltd |
| NCI-H596 | DMEM + 10% FBS | Shanghai bioleaf Biological Technology Co., Ltd |

TABLE 16

Inhibitory effect of molecules of present invention on proliferation of different cancer cells

| | | ADC-1 | | Ab-10 | |
|---|---|---|---|---|---|
| Cell line | Tumor type | $IC_{50}$ (nM) | Maximum inhibition rate (%) | $IC_{50}$ (nM) | Maximum inhibition rate (%) |
| MKN45 | gastric cancer | 0.17 | 67 | 0.15 | 41 |
| SNU5 | gastric cancer | 0.24 | 75 | 0.10 | 70 |
| BxPC3 | Pancreatic cancer | 6.9 | 71 | >1000 | 0 |
| Caki-1 | Renal cell carcinoma | 6.5 | 61 | >1000 | 0 |
| PC9 | Non-small cell lung cancer | 5.6 | 37 | >1000 | 0 |
| NCI-H596 | Non-small cell lung cancer | 103.9 | 56 | 13.7 | 13 |
| NCI-H1993 | Non-small cell lung cancer | 2.8 | 60 | 1.1 | 40 |

The results of Table 16 show that an anti-c-Met antibody of the present invention has a relatively good activity on the gastric cancer cell lines MKN45 and SUN. However, for other tumor cells expressing low levels of c-Met or with an absence of c-Met expression, such as lung cancer cells, the activity is very weak, or absent. Because an ADC-1 of the present invention additionally comprises a toxin, it has a good activity on tumor cells expressing c-Met, including the gastric cancer cell lines MKN45 and SUN, and also on lung cancer, pancreatic cancer and renal cell carcinoma cells on which c-Met antibodies have no or very weak effects.

Test Example 5. Evaluation of the Efficacy In Vivo of Anti-c-Met Antibody Toxin Conjugate (ADC) Molecules 1. Test Purpose In order to better evaluate the antitumor efficacy of an anti-c-Met antibody and ADC molecule of the present invention, a parallel comparison experiment of antibody Ab-10 and ADC-1 was performed using the method of example 10. In contrast to Example 10, this test was performed by administration of a single dose. This experiment would not be terminated, until the tumor, which was inhibited by compounds, recovered to grow.

2. The Antibody to be Tested

Ab-10 (5 mg/kg), the stock solution (2.18 mg/ml) was diluted with PBS to a final concentration of 0.5 mg/ml.
Ab-10 (10 mg/kg), the stock solution (2.18 mg/ml) was diluted with PBS to a final concentration of 1 mg/ml.
Ab-10 (30 mg/kg), the stock solution (2.18 mg/ml) was diluted with PBS to a final concentration of 3 mg/ml.
ADC-1 (2.5 mg/kg), the stock solution (10 mg/ml) was diluted with PBS to a final concentration of 0.25 mg/ml.
ADC-1 (5 mg/kg), the stock solution (10 mg/ml) was diluted with PBS to a final concentration of 0.5 mg/ml.
ADC-1 (10 mg/kg), the stock solution (10 mg/ml) was diluted with PBS to a final concentration of 1 mg/ml.
All animals were administrated by tail vein injection, and the administration volume was 0.2 ml/mouse.

3. Test Procedures

Nude mice were inoculated subcutaneously in the right rib with MKN-45 cells ($1 \times 10^6$/mouse). When the average volume of tumors reached (150.19+8.44) $mm^3$, animals were randomly divided into different administration groups with each group having 8 mice. The specific dosing regimen is shown in Table 17.

Mice were measured for tumor volume and body weight twice a week, and data was recorded.

Excel statistical software: mean value is calculated as avg; SD is calculated as STDEV; SEM is calculated as STDEV/SQRT; P value between different groups is calculated as TTEST.

Tumor volume (V) was calculated as:

$$V = \tfrac{1}{2} \times L_{length} \times L_{width}^2$$

$$\text{Tumor Inhibition Rate (\%)} = (V_0 - V_T)/V_0 \times 100\%$$

Wherein $V_0$ and $V_T$ represent the tumor volume at the beginning of the experiment and at the end of the experiment, respectively.

4. Result

2. Drug Preparation

ADC-12 was dissolved at 20 mg/ml with injection water, aliquoted and stored in a freezer at −80° C. The sample was diluted with normal saline containing 0.1% BAS to the corresponding concentration before use. The stock concentration of Ab-10 was 16.3 mg/ml, which was diluted with normal saline containing 0.1% BAS, and then aliquoted and stored in a −80° C. freezer.

3. Experimental Animals

BALB/cA-nude mice, 6-7 weeks, ♀, purchased from Shanghai Ling Chang Biological Technology Co., Ltd. Production license number: SCXK (Shanghai) 2013-0018; animal certificate number 2013001814303. Feeding environment: SPF grade.

TABLE 17

Therapeutic efficacy of administering compounds to MKN-45 nude mice

| Compound Group | Mean tumor volume (mm³) D0 | SEM | Mean tumor volume (mm³) D28 | SEM | Relative tumor volume (mm³) D18 | SEM | Relative tumor volume (mm³) D28 | SEM | Tumor Inhibition Rate D18% | P Value (d18) (vs blank) | Tumor Inhibition Rate D28% | P Value (d28) (vs blank) |
|---|---|---|---|---|---|---|---|---|---|---|---|---|
| Solvent | 150.13 | 9.84 | 1123.71 | 128.33 | 5.89 | 0.88 | 7.71 | 0.91 | — | — | — | — |
| Ab-10 (5 mg/kg) | 149.42 | 8.73 | 904.68 | 75.30 | 3.34 | 0.38 | 6.13 | 0.55 | *43.32 | 0.0188 | 20.54 | 0.1575 |
| Ab-10 (10 mg/kg) | 149.66 | 8.46 | 827.75 | 90.31 | 4.12 | 0.44 | 5.58 | 0.63 | 29.98 | 0.0943 | 27.62 | 0.0755 |
| Ab-10 (30 mg/kg) | 157.84 | 9.66 | 551.96 | 79.43 | 3.42 | 0.40 | 3.47 | 0.39 | *41.94 | 0.0230 | **55.02 | 0.00075 |
| ADC-1 (2.5 mg/kg) | 149.83 | 9.08 | 661.41 | 88.25 | 2.05 | 0.16 | 4.38 | 0.53 | **65.23 | 0.0015 | **43.23 | 0.0094 |
| ADC-1 (5 mg/kg) | 150.10 | 7.99 | 656.60 | 192.02 | 1.54 | 0.11 | 4.35 | 1.27 | **73.85 | 0.0002 | *43.54 | 0.04915 |
| ADC-1 (10 mg/kg) | 143.92 | 6.49 | 228.44 | 32.31 | 1.15 | 0.11 | 1.57 | 0.20 | **80.49 | 0.0001 | **79.63 | 0.00001 |

**$p < 0.01$
*$p < 0.05$

Conclusion: An antibody and ADC compound of the invention have an obvious effect on nude mice with MKN-45 xenograft tumor.

ADC-1 and ADC-12 were compared in parallel with the same test method described above in order to evaluate the in vivo efficacy of ADC-12 of the present invention. A single dose of 3 mg/kg was administered. The result is shown in Table 18.

TABLE 18

The inhibition effect of ADC-1 and ADC-12 on a tumor

| Inhibition Rate (%) | Day 11 | Day 15 | Day 18 | Day 21 |
|---|---|---|---|---|
| ADC-1 | 42.8 | 44.7 | 35.4 | 27.1 |
| ADC-12 | 44.6 | 54.5 | 50.5 | 50.4 |

The result above shows that the tumor inhibition rate of ADC-1 and ADC-12 was similar on day 11, but the efficiency of ADC-1 was decreased 15 days later (27.1% on day 21), while the antitumor effect of ADC-12 was maintained at the level of the eleventh day (50.4%).

Test Example 6. Effect of ADC-12 on Nude Mice with Subcutaneous Tumor Xenograft of Human Lung Cancer NCI-H1993

1. Test Purpose

Evaluation and comparison of the efficacy of ADC-12 and Ab-10 antibody solutions on nude mice with a subcutaneous tumor xenograft of human lung cancer NCI-H1993.

4. Test Procedures

Nude mice were injected subcutaneously with human lung cancer cell line NCI-H1993. When the volume of tumor reached 100-150 mm³, animals were randomly divided into groups (D0). The administration regimen and dosage are shown in Table 19. Mice were measured for tumor volume and body weight 2-3 times a week, and the data was recorded. The tumor volume (V) was calculated as:

$$V = \tfrac{1}{2} \times a \times b^2,$$

wherein a and b represent the length and width, respectively.

$$T/C\ (\%) = (T - T_0)/(C - C_0) \times 100,$$

wherein T and C represent the tumor volume at the end of the experiment. $T_0$ and $C_0$ represent the tumor volume at the beginning of the experiment.

5. Result

ADC-12 is an anti-c-Met antibody-toxin conjugate. ADC-12 (1, 3, 10 mg/kg, IV, D0) inhibited the growth of a subcutaneous xenograft tumor of c-Met over-expressing human lung cancer cell line NCI-H1993 in nude mice in a dose-dependent manner, and the tumor inhibition rates were 45%, 63%, and 124%, respectively. 70% of mice of the 10 mg/kg dose group exhibited partial regression (D21). The Ab-10 antibody stock solution was the antibody used for the preparation of ADC-12. The tumor inhibitory rate of Ab-10 antibody (30 mg/kg, IV, twice a week for 6 times) was 42% for NCI-H1993. The tumor bearing mice tolerated the above drugs well, and no symptoms such as loss of weight were observed. The effect of ADC-12 on NCI-H1993 was clearly stronger than that of Ab-10 antibody stock solution.

TABLE 19

Effect of ADC-12 and Ab-10 antibody stock solution on a subcutaneous xenograft tumor of human lung cancer cell line NCI-H1993 in nude mice

| Compound Group | Administration | Mean tumor volume (mm³) D0 | SEM | Mean tumor volume (mm³) D21 | SEM | % T/C D21 | Tumor Inhibition Rate D21% | P Value (d21) (vs blank) | partial regression |
|---|---|---|---|---|---|---|---|---|---|
| Solvent | D0 | 136.7 | ±3.4 | 1851.3 | ±116.4 | — | — | — | 0 |
| ADC-12 (1 mg/kg) | D0 | 132.5 | ±5.3 | 1075.1 | ±56.8 | 55 | 45 | 0.000 | 0 |
| ADC-12 (3 mg/kg) | D0 | 127.3 | ±3.1 | 760.8 | ±96.6 | 37 | 63 | **0.000 | 0 |
| ADC-12 (10 mg/kg) | D0 | 132.7 | ±2.9 | 100.6 | ±16.3 | −24 | 124 | **0.000 | 7 |
| Ab-10 (10 mg/kg) | D0, 3, 7, 10, 14, 17 | 129.7 | ±3.8 | 1124.0 | ±63.3 | 58 | 42 | 0.000 | 0 |

D0: time for the first administration;
P value, as compared with solvent;
**P < 0.01, as compared with that of 30 mg/kg group of Ab-10 antibody solution;
Student's t test was used. The number of mice at the beginning of the experiment: n = 10.

Discussion: ADC-12 (1, 3, 10 mg/kg, IV, D0) inhibited the growth of a subcutaneous xenograft tumor of c-Met over-expressing human lung cancer cell line NCI-H1993 in nude mice in a dose-dependent manner, resulting in partial tumor regression; Ab-10 antibody stock solution (30 mg/kg, IV, twice a week for 6 times) was also effective for NCI-H1993. The effect of ADC-12 on NCI-H1993 was clearly stronger than that of Ab-10 antibody stock solution. The tumor bearing mice tolerated the above drugs well.

The invention claimed is:

1. An antibody or antigen-binding fragment thereof that specifically binds to c-Met, comprising an antibody heavy chain variable region comprising an HCDR1 of SEQ ID NO: 6, an HCDR2 of SEQ ID NO: 7 and an HCDR3 of SEQ ID NO: 8;
and
an antibody light chain variable region comprising an LCDR1 of SEQ ID NO: 9 or SEQ ID NO:12, an LCDR2 of SEQ ID NO: 10 and an LCDR3 of SEQ ID NO: 11.

2. The antibody or antigen-binding fragment thereof that specifically binds to c-Met receptor according to claim 1, wherein the antibody or the antigen-binding fragment thereof is a murine antibody or a fragment thereof.

3. The antibody or antigen-binding fragment thereof that specifically binds to c-Met receptor according to claim 2, wherein the heavy chain variable region of the murine antibody comprises SEQ ID NO: 4 and the light chain variable region of the murine antibody comprises SEQ ID NO: 5.

4. The antibody or antigen-binding fragment thereof that specifically binds to c-Met receptor according to claim 1, wherein the antibody or the antigen-binding fragment thereof is a chimeric antibody or a humanized antibody, or a fragment thereof.

5. The antibody or antigen-binding fragment thereof that specifically binds to c-Met receptor according to claim 4 being a humanized antibody, wherein the humanized antibody heavy chain variable region comprises heavy chain framework regions having FR1, FR2, FR3 and FR4 of the human germline heavy chain IGHV 3-33*01.

6. The antibody or antigen-binding fragment thereof that specifically binds to c-Met receptor according to claim 5, wherein the humanized antibody comprises a heavy chain variable region having an amino acid sequence selected from the group consisting of SEQ ID NOs: 13, 14 and 15.

7. The antibody or antigen-binding fragment thereof that specifically binds to c-Met receptor according to claim 4 being a humanized antibody, wherein the humanized antibody light chain variable region comprises light chain framework regions having FR1, FR2, FR3 and FR4 of the human germline light chain IGKV085 or IGKV4-1*01.

8. The antibody or antigen-binding fragment thereof that specifically binds to c-Met receptor according to claim 7, wherein the humanized antibody comprises a light chain variable region having an amino acid sequence selected from the group consisting of SEQ ID NOs: 16, 17 and 18.

9. The antibody or antigen-binding fragment thereof that specifically binds to c-Met receptor according to claim 1, comprising a combination of a heavy chain variable region amino acid sequence and a light chain variable region amino acid sequence selected from any one of (a) to (c):
(a) Heavy chain variable region sequence of SEQ ID NO: 13, and light chain variable region sequence of SEQ ID NO: 16;
(b) Heavy chain variable region sequence of SEQ ID NO: 14, and light chain variable region sequence of SEQ ID NO: 17; and
(c) Heavy chain variable region sequence of SEQ ID NO: 15, and light chain variable region sequence of SEQ ID NO: 18.

10. The antibody or antigen-binding fragment thereof that specifically binds to c-Met receptor according to claim 4 being a humanized antibody, wherein the heavy chain constant region of the humanized antibody comprises a constant region derived from human IgG1, or a variant thereof, human IgG2, or a variant thereof, human IgG3, or a variant thereof, or human IgG4, or a variant thereof.

11. The antibody or antigen-binding fragment thereof that specifically binds to c-Met receptor according to claim 10, comprising a full length heavy chain sequence selected from the group consisting of SEQ ID NOs: 23, 24 and 25.

12. The antibody or antigen-binding fragment thereof that specifically binds to c-Met receptor according to claim 4 being a humanized antibody, wherein the light chain constant region of the humanized antibody comprises a constant region selected from the group consisting of human κ and human λ, or a variant thereof.

13. The antibody or antigen-binding fragment thereof that specifically binds to c-Met receptor according to claim 12, comprising a full-length light chain sequence selected from the group consisting of SEQ ID NOs: 26, 27 and 28.

14. The antibody or antigen-binding fragment thereof that specifically binds to c-Met receptor according claim 4 being a humanized antibody, wherein the humanized antibody comprises a combination of a full-length light chain sequence and a full-length heavy chain selected from the group consisting of:
Ab-9, comprising a heavy chain amino acid sequence of SEQ ID NO: 23 and a light chain amino acid sequence of SEQ ID NO: 26;
Ab-10, comprising a heavy chain amino acid sequence of SEQ ID NO: 24 and a light chain amino acid sequence of SEQ ID NO: 27; and
Ab-11, comprising a heavy chain amino acid sequence of SEQ ID NO: 25 and a light chain amino acid sequence of SEQ ID NO: 28.

15. A nucleic acid molecule encoding the antibody or antigen-binding fragment thereof that specifically binds to c-Met receptor according to claim 1.

16. An expression vector comprising the nucleic acid molecule according to claim 15.

17. A host cell transformed with the expression vector according to claim 16.

18. A pharmaceutical composition comprising the antibody or the antigen-binding fragment thereof that specifically binds to c-Met receptor according to claim 1, and one or more pharmaceutically acceptable excipients, diluents or carriers.

19. An antibody-cytotoxic drug conjugate of formula (I) or a pharmaceutically acceptable salt or solvate thereof:

$$Ab-[(L_2)t-L_1-D)]y \qquad (I)$$

wherein:
D is a drug unit;
$L_1$ and $L_2$ are linker units;
t is 0 or 1;
y is 1-8; and
Ab is the antibody or antigen-binding fragment thereof that specifically binds to c-Met receptor according to claim 1.

20. The antibody-cytotoxic drug conjugate of formula (I) or the pharmaceutically acceptable salt or solvate thereof according to claim 19, wherein -$L_2$-comprises formula (-$L_2$-):

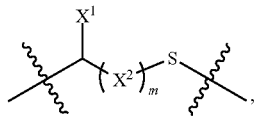

wherein:
$X^1$ is selected from the group consisting of hydrogen, halogen, hydroxyl, cyano, alkyl, alkoxy and cycloalkyl;
$X^2$ is selected from the group consisting of alkyl, cycloalkyl and heterocyclyl;
m is 0, 1, 2, 3, 4 or 5; and
S is a sulfur atom.

21. The antibody-cytotoxic drug conjugate of formula (I) or the pharmaceutically acceptable salt or solvate thereof according to claim 19, wherein the drug unit D is a cytotoxic agent selected from the group consisting of toxins, chemotherapeutic agents, antibiotics, radioisotopes and nucleolytic enzymes.

22. The antibody-cytotoxic drug conjugate of formula (I) or the pharmaceutically acceptable salt or solvate thereof according to claim 19, wherein D is formula (D):

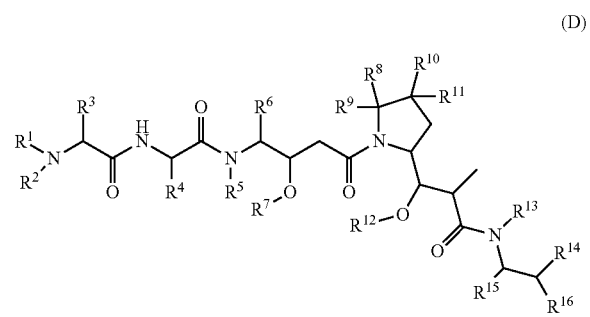

(D)

or a tautomer, mesomer, racemate, enantiomer, or diastereomer thereof, or mixtures thereof, or a pharmaceutically acceptable salt thereof;
wherein:
$R^1$-$R^7$ are each selected from the group consisting of hydrogen, halogen, hydroxyl, cyano, alkyl, alkoxy and cycloalkyl;

the group consisting of hydrogen, halogen, hydroxy, alkyl, alkoxy and cycloalkyl;
$R^{15}$ is selected from the group consisting of halogen, alkenyl, alkyl, cycloalkyl and $COOR^{17}$;
$R^{16}$ is selected from the group consisting of hydrogen, halogen, hydroxy, cyano, alkyl, alkoxy and cycloalkyl; and
$R^{17}$ is selected from the group consisting of hydrogen, alkyl and alkoxy.

23. The antibody-cytotoxic drug conjugate of formula (I) or the pharmaceutically acceptable salt or solvate thereof according to claim 22, wherein $L_2$ comprises a linker selected from the group consisting of valine-citrulline, 6-maleimido-caproyl, P-aminobenzyloxycarbonyl and 6-maleimido-caproyl-P-aminobenzyloxycarbonyl.

24. The antibody-cytotoxic drug conjugate of formula (I) or the pharmaceutically acceptable salt or solvate thereof according to claim 19, wherein D is a maytansinoid alkaloid.

25. The antibody-cytotoxic drug conjugate or the pharmaceutically acceptable salt or solvate thereof according to claim 24, wherein $L_2$ is selected from the group consisting of N-succinimidyl 4-(2-pyridylthio) valerate (SPP), N-succinimidyl 4-(N-maleimidomethyl)-cyclohexane-1-Carboxylic acid ester (SMCC), and N-succinimidyl (4-iodo-acetyl) aminobenzoate (SIAB).

26. The antibody-cytotoxic drug conjugate of formula (I) or the pharmaceutically acceptable salt or solvate thereof according to claim 19, wherein D is a camptothecin alkaloid.

27. The antibody-cytotoxic drug conjugate of formula (I) or the pharmaceutically acceptable salt or solvate thereof according to claim 26, wherein $L_2$ is a linker selected from the group consisting of valine-citrulline, 6-maleimido-caproyl, P-aminobenzyloxycarbonyl or 6-maleimido-caproyl-P-aminobenzyloxycarbonyl.

28. The antibody-cytotoxic drug conjugate of formula (I) or the pharmaceutically acceptable salt or solvate thereof according to claim 19, which is a conjugated drug of formula (II) or a pharmaceutically acceptable salt or solvate thereof:

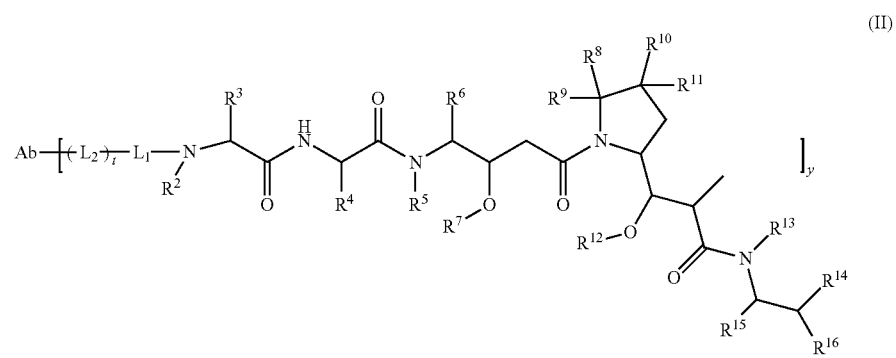

(II)

wherein:
$R^2$-$R^7$ are each selected from the group consisting of hydrogen, halogen, hydroxyl, cyano, alkyl, alkoxy and cycloalkyl;
$R^8$-$R^{11}$ are each optionally selected from the group consisting of hydrogen, halogen, alkenyl, alkyl, alkoxy and cycloalkyl;
or any two of $R^8$-$R^{11}$ form a cycloalkyl, and the rest are each selected from the group consisting of hydrogen, alkyl and cycloalkyl;
$R^{12}$-$R^{13}$ are each selected from the group consisting of hydrogen, alkyl and halogen;

$R^8$-$R^{11}$ are each optionally selected from the group consisting of hydrogen, halogen, alkenyl, alkyl, alkoxy and cycloalkyl;
or any two of $R^8$-$R^{11}$ form a cycloalkyl, and the rest are each selected from the group consisting of hydrogen, alkyl and cycloalkyl;
$R^{12}$-$R^{13}$ are each selected from the group consisting of hydrogen, alkyl and halogen;
$R^{14}$ is selected from the group consisting of aryl and heteroaryl, wherein the aryl or heteroaryl is optionally further substituted by a substituent group selected from $R^{14}$ is selected from the group consisting of aryl and heteroaryl, wherein the aryl or heteroaryl is optionally further substituted by a substituent group selected from the group consisting of hydrogen, halogen, hydroxy, alkyl, alkoxy and cycloalkyl;

$R^{15}$ is selected from the group consisting of halogen, alkenyl, alkyl, cycloalkyl and $COOR^{17}$;

$R^{16}$ is selected from the group consisting of hydrogen, halogen, hydroxy, cyano, alkyl, alkoxy and cycloalkyl; and $R^{17}$ is selected from the group consisting of hydrogen, alkyl and alkoxy.

29. The antibody-cytotoxic drug conjugate of formula (I) or the pharmaceutically acceptable salt or solvate thereof according to claim 19, which is a conjugated drug of formula (III) or a pharmaceutically acceptable salt or solvate thereof:

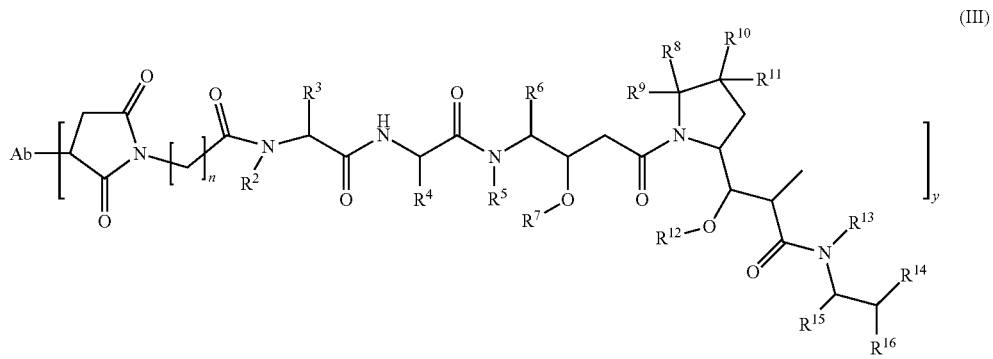

(III)

wherein:
$R^2$-$R^7$ are each selected from the group consisting of hydrogen, halogen, hydroxyl, cyano, alkyl, alkoxy and cycloalkyl;

$R^8$-$R^{11}$ are each optionally selected from the group consisting of hydrogen, halogen, alkenyl, alkyl, alkoxy and cycloalkyl; or any two of $R^8$-$R^{11}$ form a cycloalkyl, and the rest are each selected from the group consisting of hydrogen, alkyl and cycloalkyl;

$R^{12}$-$R^{13}$ are each selected from the group consisting of hydrogen, alkyl and halogen;

$R^{14}$ is selected from the group consisting of aryl and heteroaryl, wherein the aryl or heteroaryl is optionally further substituted by a substituent group selected from the group consisting of hydrogen, halogen, hydroxy, alkyl, alkoxy and cycloalkyl;

$R^{15}$ is selected from the group consisting of halogen, alkenyl, alkyl, cycloalkyl and $COOR^{17}$;

$R^{16}$ is selected from the group consisting of hydrogen, halogen, hydroxy, cyano, alkyl, alkoxy and cycloalkyl;

$R^{17}$ is selected from the group consisting of hydrogen, alkyl and alkoxy; and n is 3, 4, 5 or 6.

30. The antibody-cytotoxic drug conjugate of formula (I) or the pharmaceutically acceptable salt or solvate thereof according to claim 19, which is a conjugated drug of formula (IV) or a pharmaceutically acceptable salt or solvate thereof:

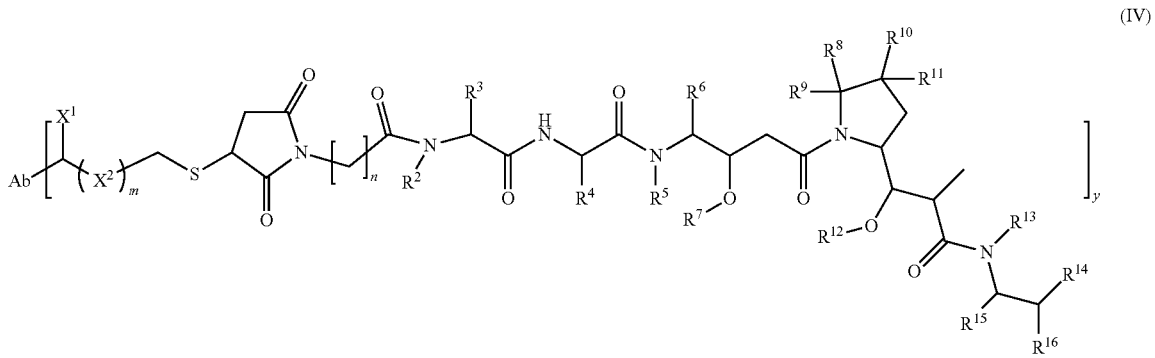

(IV)

wherein:

$R^2$-$R^7$ are each selected from the group consisting of hydrogen, halogen, hydroxyl, cyano, alkyl, alkoxy and cycloalkyl;

$R^8$-$R^{11}$ are each optionally selected from the group consisting of hydrogen, halogen, alkenyl, alkyl, alkoxy and cycloalkyl;

or any two of $R^8$-$R^{11}$ form a cycloalkyl, and the rest are each selected from the group consisting of hydrogen, alkyl and cycloalkyl;

$R^{12}$-$R^{13}$ are each selected from the group consisting of hydrogen, alkyl and halogen;

$R^{14}$ is selected from the group consisting of aryl and heteroaryl, wherein the aryl or heteroaryl is optionally further substituted by a substituent group selected from the group consisting of hydrogen, halogen, hydroxy, alkyl, alkoxy and cycloalkyl;

$R^{15}$ is selected from the group consisting of halogen, alkenyl, alkyl, cycloalkyl and $COOR^{17}$;

$R^{16}$ is selected from the group consisting of hydrogen, halogen, hydroxy, cyano, alkyl, alkoxy and cycloalkyl;

$R^{17}$ is selected from the group consisting of hydrogen, alkyl and alkoxy;

n is 3, 4, 5 or 6;

$X^1$ is selected from the group consisting of hydrogen, halogen, hydroxyl, cyano, alkyl, alkoxy and cycloalkyl;

$X^2$ is selected from the group consisting of alkyl, cycloalkyl and heterocyclyl; and m is 0, 1, 2, 3, 4 or 5.

31. The antibody-cytotoxic drug conjugate of formula (I) or the pharmaceutically acceptable salt or solvate thereof according to claim 19, which is a conjugated drug of formula (V) or a pharmaceutically acceptable salt or solvate thereof:

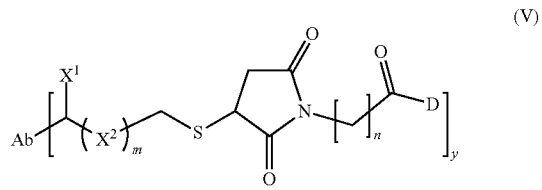

(V)

wherein:

n is 3, 4, 5 or 6;

$X^1$ is selected from the group consisting of hydrogen, halogen, hydroxyl, cyano, alkyl, alkoxy and cycloalkyl;

$X^2$ is selected from the group consisting of alkyl, cycloalkyl and heterocyclyl; and m is 0, 1, 2, 3, 4 or 5.

32. An antibody-cytotoxic drug conjugate selected from the group consisting of:

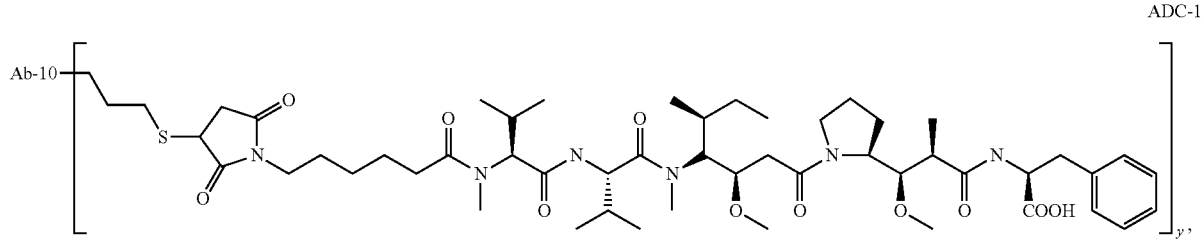

ADC-1

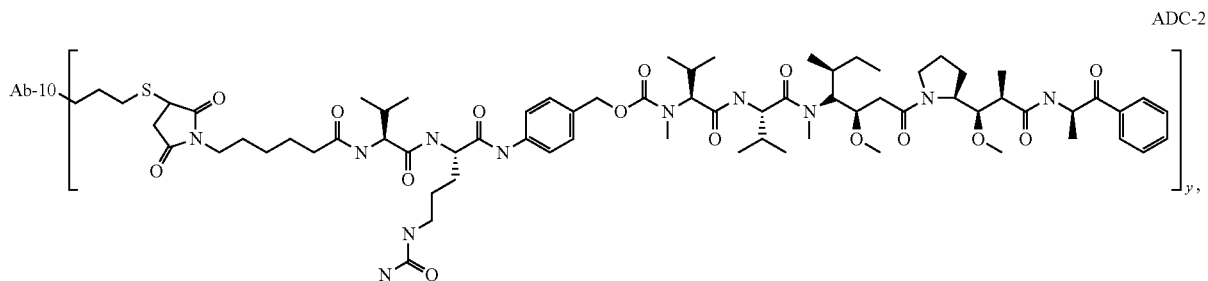

ADC-2

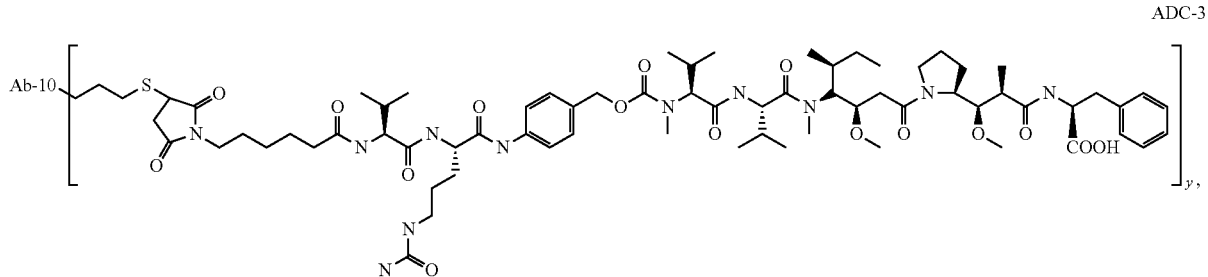

ADC-3

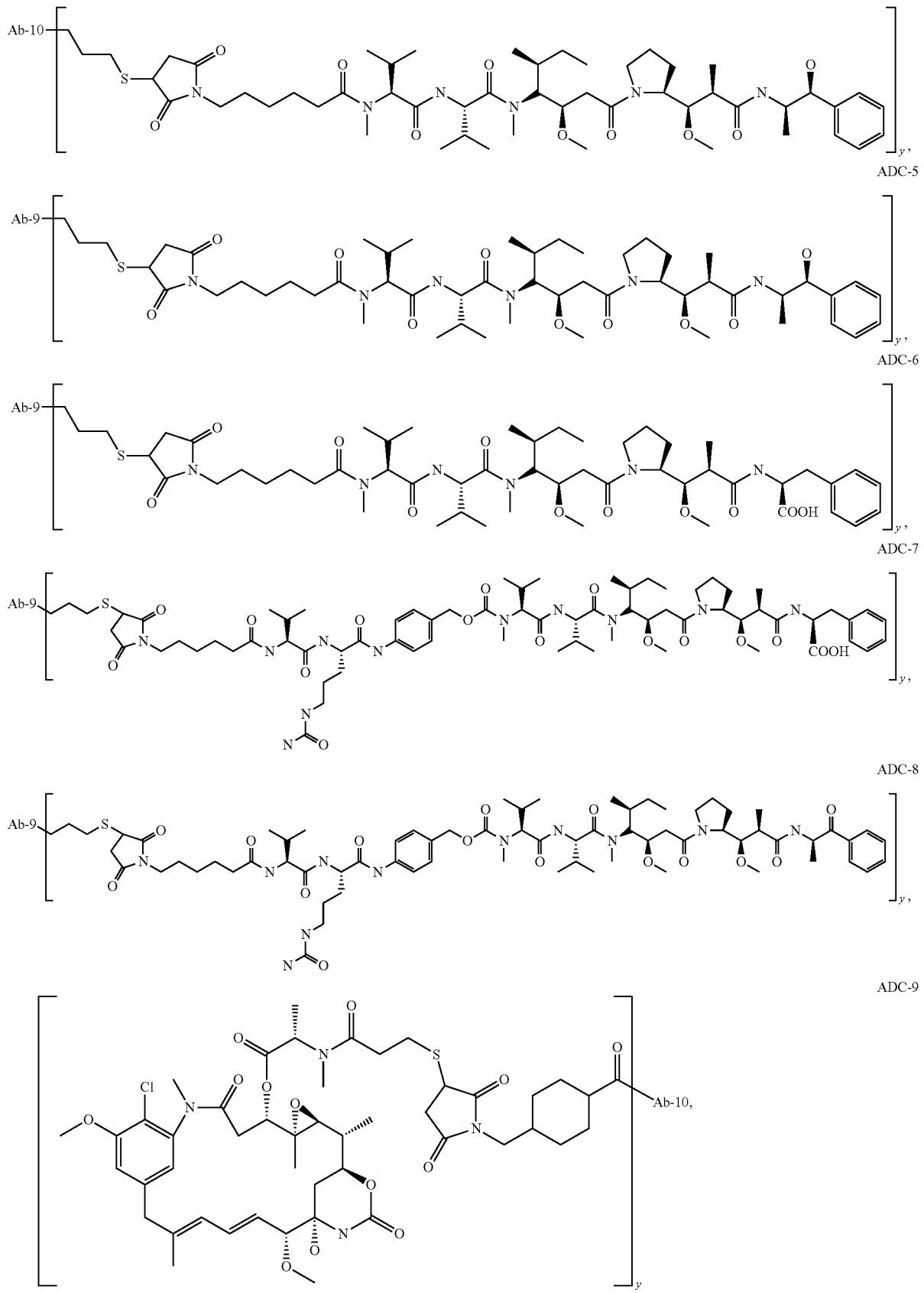

ADC-10
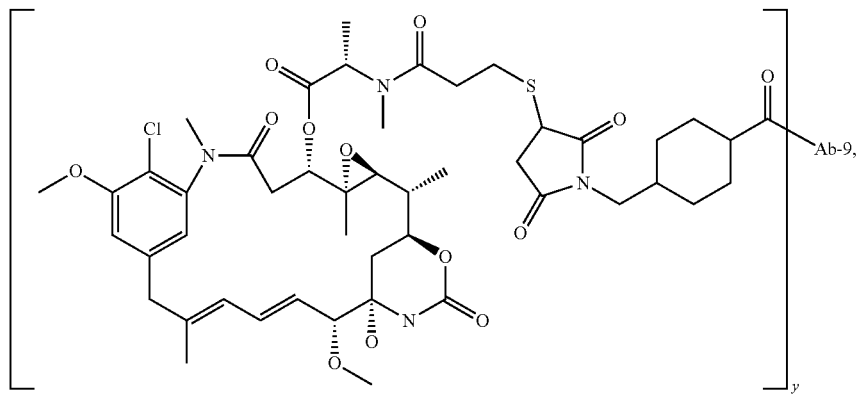
ADC-11
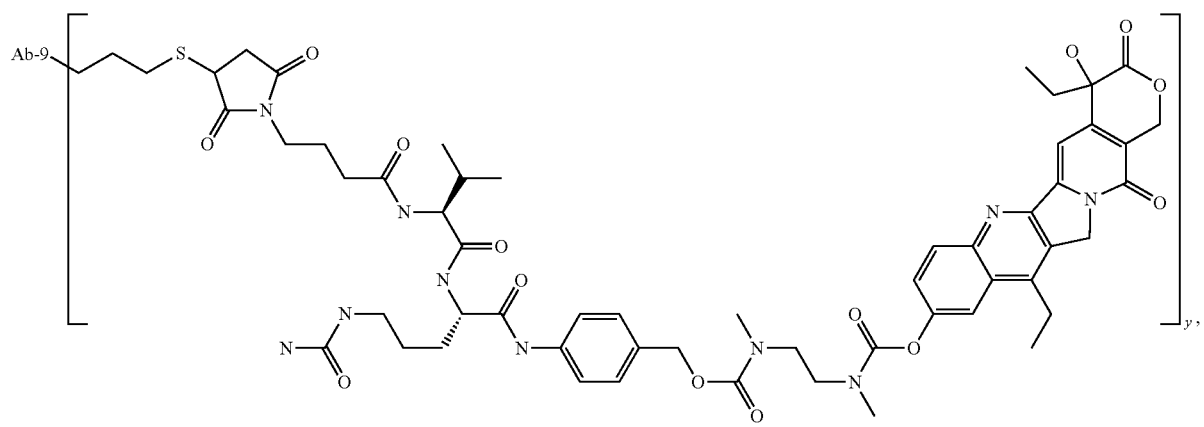
ADC-12
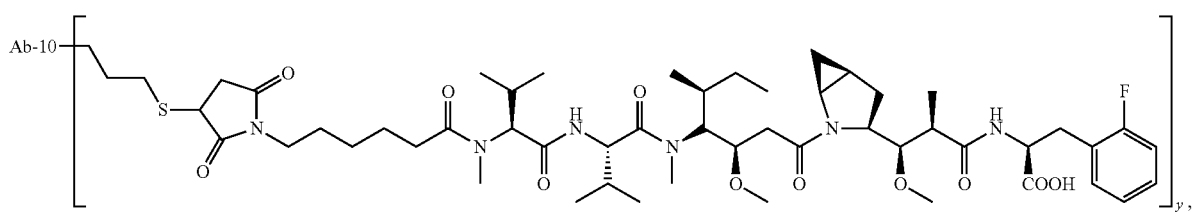
ADC-13
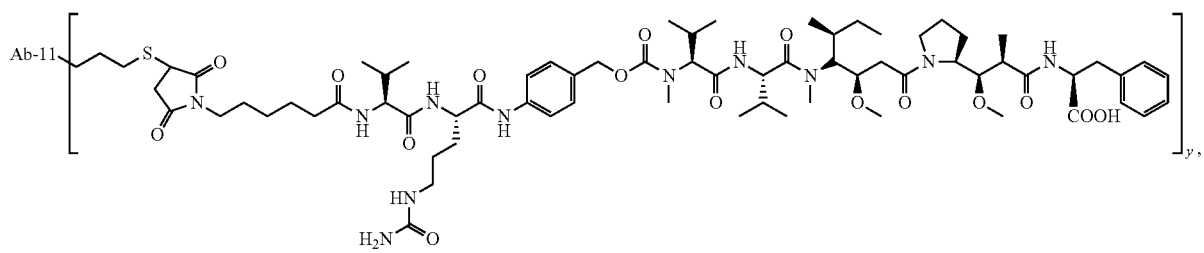
ADC-14
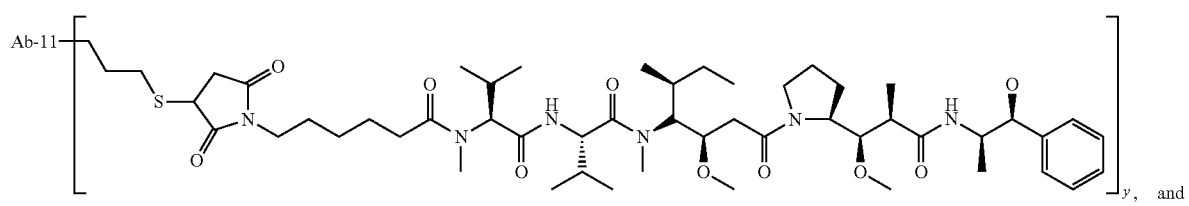
and

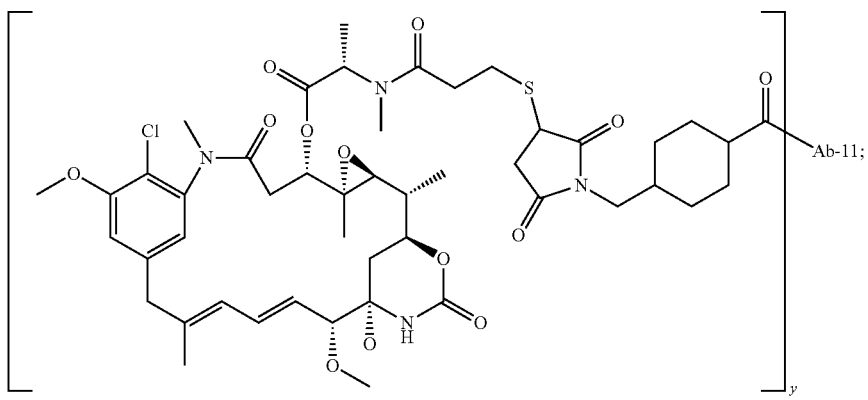

ADC-15 or a pharmaceutically acceptable salt or solvate thereof, wherein y is 1-8;

Ab-9 is a humanized antibody comprising a heavy chain amino acid sequence of SEQ ID NO: 23 and a light chain amino acid sequence of SEQ ID NO: 26;

Ab-10 is a humanized antibody comprising a heavy chain amino acid sequence of SEQ ID NO: 24 and a light chain amino acid sequence of SEQ ID NO: 27; and Ab-11 is a humanized antibody comprising a heavy chain amino acid sequence of SEQ ID NO: 25 and a light chain amino acid sequence of SEQ ID NO: 28.

33. A process of preparing the conjugated drug of formula (V) or the pharmaceutically acceptable salt or solvate thereof according to claim 31, comprising:

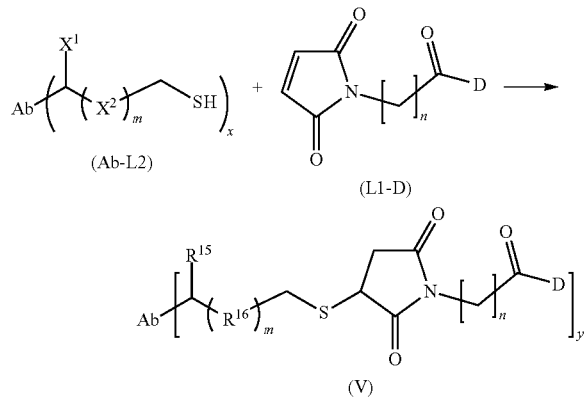

wherein a compound of the general formula (Ab-L2) is reacted with a compound of the general formula (L1-D) in an organic solvent to obtain a compound of the general formula (V);

wherein x is 0-5.

34. A pharmaceutical composition comprising the antibody-cytotoxic drug conjugate of formula (I) or the pharmaceutically acceptable salt or solvate thereof according to claim 19, and one or more pharmaceutically acceptable excipients, diluents or carriers.

35. A method of treating a c-Met-mediated disease or condition, the method comprising administering to a subject in need thereof a pharmaceutical composition according to claim 18, wherein the c-Met-mediated disease or condition is a cancer selected from the group consisting of gastric cancer, pancreatic cancer, lung cancer, intestinal cancer, kidney cancer, and melanoma.

36. A method of treating a c-Met-mediated disease or condition, the method comprising administering to a subject in need thereof a pharmaceutical composition according to claim 34, wherein the c-Met-mediated disease or condition is a cancer selected from the group consisting of gastric cancer, pancreatic cancer, lung cancer, intestinal cancer, kidney cancer, and melanoma.

\* \* \* \* \*

```
SEQUENCE LISTING

<160> NUMBER OF SEQ ID NOS: 28

<210> SEQ ID NO 1
<211> LENGTH: 2796
<212> TYPE: DNA
<213> ORGANISM: Artificial sequence
<220> FEATURE:
<223> OTHER INFORMATION: human cMet extracellular domain (ECD) and
      murine Fc region fusion protein (human cMet ECD-mFc) DNA sequence

<400> SEQUENCE: 1
atgaaggccc ccgctgtgct tgcacctggc atcctcgtgc tcctgtttac cttggtgcag      60
aggagcaatg gggagtgtaa agaggcacta gcaaagtccg agatgaatgt gaatatgaag     120
tatcagcttc caacttcac cgcggaaaca cccatccaga atgtcattct acatgagcat     180
cacattttcc ttggtgccac taactacatt tatgttttaa atgaggaaga ccttcagaag     240
gttgctgagt acaagactgg gcctgtgctg gaacacccag attgtttccc atgtcaggac     300
tgcagcagca aagccaattt atcaggaggt gtttggaaag ataacatcaa catggctcta     360
gttgtcgaca cctactatga tgatcaactc attagctgtg gcagcgtcaa cagagggacc     420
tgccagcgac atgtctttcc ccacaatcat actgctgaca tacagtcgga ggttcactgc     480
atattctccc cacagataga agagcccagc cagtgtcctg actgtgtggt gagcgccctg     540
ggagccaaag tcctttcatc tgtaaaggac cggttcatca acttctttgt aggcaatacc     600
ataaattctt cttatttccc agatcatcca ttgcattcga tatcagtgag aaggctaaag     660
gaaacgaaag atggttttat gttttggacg gaccagtcct acattgatgt tttacctgag     720
ttcagagatt cttaccccat taagtatgtc catgcctttg aaagcaacaa ttttatttac     780
ttcttgacgg tccaaaggga aactctagat gctcagactt tcacacaag aataatcagg     840 ttctgttcca taaactctgg attgcattcc tacatggaaa tgcctctgga gtgtattctc     900
acagaaaaga gaaaaagag atccacaaag aaggaagtgt taatatact tcaggctgcg     960 tatgtcagca agcctggggc ccagcttgct agacaaatag gagccagcct gaatgatgac    1020 attctttcg gggtgttcgc acaaagcaag ccagattctg ccgaaccaat ggatcgatct    1080
```

```
gccatgtgtg cattccctat caaatatgtc aacgacttct tcaacaagat cgtcaacaaa    1140
aacaatgtga gatgtctcca gcattttac  ggacccaatc atgagcactg ctttaatagg    1200
acacttctga gaaattcatc aggctgtgaa gcgcgccgtg atgaatatcg aacagagttt    1260
accacagctt tgcagcgcgt tgacttattc atgggtcaat tcagcgaagt cctcttaaca    1320
tctatatcca ccttcattaa aggagacctc accatagcta atcttgggac atcagagggt    1380
cgcttcatgc aggttgtggt ttctcgatca ggaccatcaa cccctcatgt gaattttctc    1440
ctggactccc atccagtgtc tccagaagtg attgtggagc atacattaaa ccaaaatggc    1500
tacacactgg ttatcactgg gaagaagatc acgaagatcc cattgaatgg cttgggctgc    1560
agacatttcc agtcctgcag tcaatgcctc tctgccccac cctttgttca gtgtggctgg    1620
tgccacgaca aatgtgtgcg atcggaggaa tgcctgagcg gacatggac  tcaacagatc    1680 tgtctgcctg caatctacaa ggttttccca aatagtgcac cccttgaagg agggacaagg    1740
ctgaccatat gtggctggga ctttggattt cggaggaata taaatttga  tttaaagaaa    1800 actagagttc tccttggaaa tgagagctgc accttgactt taagtgagag cacgatgaat    1860
acattgaaat gcacagttgg tcctgccatg aataagcatt tcaatatgtc cataattatt    1920
tcaaatggcc acgggacaac acaatacagt acattctcct atgtggatcc tgtaataaca    1980
agtatttcgc cgaaatacgg tcctatggct ggtggcactt tacttacttt aactggaaat    2040
tacctaaaca gtgggaattc tagacacatt tcaattggtg gaaaaacatg tactttaaaa    2100
agtgtgtcaa acagtattct tgaatgttat accccagccc aaaccatttc aactgagttt    2160
gctgttaaat tgaaaattga cttagccaac cgagagacaa gcatcttcag ttaccgtgaa    2220
gatcccattg tctatgaaat tcatccaacc aaatctttta ttagtggtgg agcacaata    2280 acaggtgttg gaaaaacct  gaattcagtt agtgtcccga gaatggtcat aaatgtgcat    2340
gaagcaggaa ggaactttac agtggcatgt caacatcgct ctaattcaga gataatctgt    2400
tgtaccactc cttccctgca acagctgaat ctgcaactcc ccctgaaaac caaagccttt    2460
ttcatgttag atgggatcct ttccaaatac tttgatctca tttatgtaca taatcctgtg    2520
tttaagcctt ttgaaaagcc agtgatgatc tcaatgggca atgaaaatgt actgaaaatt    2580
aagggaaatg atattgaccc tgaagcagtt aaaggtgaag tgttaaaagt tggaaataag    2640
agctgtgaga atatacactt acattctgaa gccgttttat gcacggtccc caatgacctg    2700
ctgaaattga acagcgagct aaatatagag tggaagcaag caatttcttc aaccgtcctt    2760
ggaaaagtaa tagttcaacc agatcagaat ttcaca                              2796
```

<210> SEQ ID NO 2
<211> LENGTH: 1758
<212> TYPE: DNA
<213> ORGANISM: Artificial sequence
<220> FEATURE:
<223> OTHER INFORMATION: human cMet extracellular Sema domain and
      Flag-His tag (Human cMet Sema-Flis) DNA sequence

<400> SEQUENCE: 2

```
atgaaggccc ccgctgtgct tgcacctggc atcctcgtgc tcctgtttac cttggtgcag      60
aggagcaatg gggagtgtaa agaggcacta gcaaagtccg agatgaatgt gaatatgaag     120
tatcagcttc ccaacttcac cgcggaaaca cccatccaga tgtcattct  acatgagcat     180 cacattttcc ttggtgccac taactacatt tatgttttaa atgaggaaga ccttcagaag     240
gttgctgagt acaagactgg gcctgtgctg gaacacccag attgtttccc atgtcaggac     300
```

```
tgcagcagca aagccaattt atcaggaggt gtttggaaag ataacatcaa catggctcta    360
gttgtcgaca cctactatga tgatcaactc attagctgtg gcagcgtcaa cagagggacc    420
tgccagcgac atgtctttcc ccacaatcat actgctgaca tacagtcgga ggttcactgc    480
atattctccc cacagataga agagcccagc cagtgtcctg actgtgtggt gagcgccctg    540
ggagccaaag tcctttcatc tgtaaaggac cggttcatca acttctttgt aggcaatacc    600
ataaattctt cttatttccc agatcatcca ttgcattcga tatcagtgag aaggctaaag    660
gaaacgaaag atggttttat gtttttgacg gaccagtcct acattgatgt tttacctgag    720
ttcagagatt cttaccccat taagtatgtc catgcctttg aaagcaacaa ttttatttac    780
ttcttgacgg tccaaaggga aactctagat gctcagactt ttcacacaag aataatcagg    840
ttctgttcca taaactctgg attgcattcc tacatggaaa tgcctctgga gtgtattctc    900
acagaaaaga gaaaaagag atccacaaag aaggaagtgt taatatact tcaggctgcg    960 tatgtcagca agcctggggc ccagcttgct agacaaatag gagccagcct gaatgatgac   1020
attcttttcg gggtgttcgc acaaagcaag ccagattctg ccgaaccaat ggatcgatct   1080
gccatgtgtg cattccctat caaatatgtc aacgacttct tcaacaagat cgtcaacaaa   1140
aacaatgtga gatgtctcca gcattttttac ggacccaatc atgagcactg ctttaatagg   1200
acacttctga gaaattcatc aggctgtgaa gcgcgccgtg atgaatatcg aacagagttt   1260
accacagctt tgcagcgcgt tgacttattc atgggtcaat tcagcgaagt cctcttaaca   1320
tctatatcca ccttcattaa aggagacctc accatagcta atcttgggac atcagagggt   1380
cgcttcatgc aggttgtggt ttctcgatca ggaccatcaa cccctcatgt gaattttctc   1440
ctggactccc atccagtgtc tccagaagtg attgtggagc atacattaaa ccaaaatggc   1500
tacacactgg ttatcactgg gaagaagatc acgaagatcc cattgaatgg cttgggctgc   1560
agacatttcc agtcctgcag tcaatgcctc tctgccccac cctttgttca gtgtggctgg   1620
tgccacgaca aatgtgtgcg atcggaggaa tgcctgagcg gacatggac tcaacagatc   1680 tgtctgcctg caatctacaa ggactacaag gacgacgacg acaagcatgt ccaccatcat   1740
caccatcact gattcgaa                                                 1758

<210> SEQ ID NO 3
<211> LENGTH: 2823
<212> TYPE: DNA
<213> ORGANISM: Artificial sequence
<220> FEATURE:
<223> OTHER INFORMATION: human c-Met ECD his tag (Human cMet ECD-His)
      recombinant protein DNA sequence

<400> SEQUENCE: 3
atgaaggccc ccgctgtgct tgcacctggc atcctcgtgc tcctgtttac cttggtgcag     60
aggagcaatg gggagtgtaa agaggcacta gcaaagtccg agatgaatgt gaatatgaag    120
tatcagcttc ccaacttcac cgcggaaaca cccatccaga atgtcattct acatgagcat    180
cacattttcc ttggtgccac taactacatt tatgttttaa atgaggaaga ccttcagaag    240
gttgctgagt acaagactgg gcctgtgctg gaacacccag attgtttccc atgtcaggac    300
tgcagcagca aagccaattt atcaggaggt gtttggaaag ataacatcaa catggctcta    360
gttgtcgaca cctactatga tgatcaactc attagctgtg gcagcgtcaa cagagggacc    420
tgccagcgac atgtctttcc ccacaatcat actgctgaca tacagtcgga ggttcactgc    480
atattctccc cacagataga agagcccagc cagtgtcctg actgtgtggt gagcgccctg    540
```

```
ggagccaaag tcctttcatc tgtaaaggac cggttcatca acttctttgt aggcaatacc      600
ataaattctt cttatttccc agatcatcca ttgcattcga tatcagtgag aaggctaaag      660
gaaacgaaag atggttttat gttttttgacg gaccagtcct acattgatgt tttacctgag     720
ttcagagatt cttaccccat taagtatgtc catgcctttg aaagcaacaa ttttatttac      780
ttcttgacgg tccaaaggga aactctagat gctcagactt tcacacaag aataatcagg       840 ttctgttcca taaactctgg attgcattcc tacatggaaa tgcctctgga gtgtattctc      900
acagaaaaga gaaaaagag atccacaaag aaggaagtgt taatatact tcaggctgcg        960 tatgtcagca agcctggggc ccagcttgct agacaaatag gagccagcct gaatgatgac     1020
attcttttcg gggtgttcgc acaaagcaag ccagattctg ccgaaccaat ggatcgatct     1080
gccatgtgtg cattccctat caaatatgtc aacgacttct tcaacaagat cgtcaacaaa     1140
aacaatgtga gatgtctcca gcattttttac ggacccaatc atgagcactg ctttaatagg    1200
acacttctga gaaattcatc aggctgtgaa gcgcgccgtg atgaatatcg aacagagttt     1260
accacagctt tgcagcgcgt tgacttattc atgggtcaat tcagcgaagt cctcttaaca     1320
tctatatcca ccttcattaa aggagacctc accatagcta atcttgggac atcagagggt     1380
cgcttcatgc aggttgtggt ttctcgatca ggaccatcaa cccctcatgt gaattttctc     1440
ctggactccc atccagtgtc tccagaagtg attgtggagc atacattaaa ccaaaatggc     1500
tacacactgg ttatcactgg gaagaagatc acgaagatcc cattgaatgg cttgggctgc     1560
agacatttcc agtcctgcag tcaatgcctc tctgccccac cctttgttca gtgtggctgg     1620
tgccacgaca aatgtgtgcg atcggaggaa tgcctgagcg ggacatggac tcaacagatc     1680
tgtctgcctg caatctacaa ggttttccca aatagtgcac ccttgaagg agggacaagg       1740 ctgaccatat gtggctggga ctttggatttt cggaggaata ataaatttga tttaaagaaa    1800
actagagttc tccttggaaa tgagagctgc accttgactt taagtgagag cacgatgaat     1860
acattgaaat gcacagttgg tcctgccatg aataagcatt tcaatatgtc cataattatt     1920
tcaaatggcc acgggacaac acaatacagt acattctcct atgtggatcc tgtaataaca     1980
agtatttcgc cgaaatacgg tcctatggct ggtggcactt tacttacttt aactggaaat     2040
tacctaaaca gtgggaattc tagacacatt tcaattggtg aaaaacatg tactttaaaa      2100 agtgtgtcaa acagtattct tgaatgttat accccagccc aaaccatttc aactgagttt     2160
gctgttaaat tgaaaattga cttagccaac cgagagacaa gcatcttcag ttaccgtgaa     2220
gatcccattg tctatgaaat tcatccaacc aaatctttta ttagtggtgg agcacaata     2280 acaggtgttg ggaaaaacct gaattcagtt agtgtcccga gaatggtcat aaatgtgcat    2340
gaagcaggaa ggaactttac agtggcatgt caacatcgct ctaattcaga gataatctgt   2400
tgtaccactc cttccctgca acagctgaat ctgcaactcc ccctgaaaac caaagccttt   2460
ttcatgttag atgggatcct ttccaaatac tttgatctca tttatgtaca taatcctgtg   2520
tttaagcctt ttgaaaagcc agtgatgatc tcaatgggca atgaaaatgt actggaaatt   2580
aagggaaatg atattgaccc tgaagcagtt aaaggtgaag tgttaaaagt tggaaataag   2640
agctgtgaga atatacactt acattctgaa gccgttttat gcacggtccc caatgacctg   2700
ctgaaattga acagcgagct aaatatagag tggaagcaag caatttcttc aaccgtcctt   2760
ggaaaagtaa tagttcaacc agatcagaat ttcacacacc atcatcacca tcactgattc   2820
gaa                                                                  2823
```

<210> SEQ ID NO 4
<211> LENGTH: 120
<212> TYPE: PRT
<213> ORGANISM: Murine

<400> SEQUENCE: 4

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Pro Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Ser Thr Asn Tyr Ala Ala Ala Phe Val
    50                  55                  60

Ser Arg Leu Arg Ile Ser Lys Asp Asn Ser Lys Ser Gln Val Phe Phe
65                  70                  75                  80

Glu Met Asn Ser Leu Gln Ala Asp Asp Thr Ala Val Tyr Tyr Cys Ala
                85                  90                  95

Arg Asn His Asp Asn Pro Tyr Asn Tyr Ala Met Asp Tyr Trp Gly Gln
            100                 105                 110

Gly Thr Thr Val Thr Val Ser Ser
        115                 120

<210> SEQ ID NO 5
<211> LENGTH: 112
<212> TYPE: PRT
<213> ORGANISM: Murine

<400> SEQUENCE: 5

Asp Ile Val Leu Thr Gln Ser Pro Gly Ser Leu Ala Val Tyr Leu Gly
1               5                   10                  15

Gln Arg Ala Thr Ile Ser Cys Arg Ala Asn Lys Ser Val Ser Thr Ser
            20                  25                  30

Thr Tyr Asn Tyr Leu His Trp Tyr Gln Gln Lys Pro Gly Gln Pro Pro
        35                  40                  45

Lys Leu Leu Ile Tyr Leu Ala Ser Asn Leu Ala Ser Gly Val Pro Ala
    50                  55                  60

Arg Phe Ser Gly Ser Gly Ser Gly Thr Asp Phe Thr Leu Asn Ile His
65                  70                  75                  80

Pro Leu Glu Glu Glu Asp Ala Ala Thr Tyr Tyr Cys Gln His Ser Arg
                85                  90                  95

Asp Leu Pro Pro Thr Phe Gly Ala Gly Thr Lys Leu Glu Leu Lys Arg
            100                 105                 110

<210> SEQ ID NO 6
<211> LENGTH: 5
<212> TYPE: PRT
<213> ORGANISM: Murine

<400> SEQUENCE: 6

Asn Tyr Gly Val His
1               5

<210> SEQ ID NO 7
<211> LENGTH: 16
<212> TYPE: PRT
<213> ORGANISM: Murine

<400> SEQUENCE: 7

```
Val Ile Trp Ser Gly Gly Ser Thr Asn Tyr Ala Ala Ala Phe Val Ser
1               5                   10                  15

<210> SEQ ID NO 8
<211> LENGTH: 12
<212> TYPE: PRT
<213> ORGANISM: Murine

<400> SEQUENCE: 8

Asn His Asp Asn Pro Tyr Asn Tyr Ala Met Asp Tyr
1               5                   10

<210> SEQ ID NO 9
<211> LENGTH: 15
<212> TYPE: PRT
<213> ORGANISM: Murine

<400> SEQUENCE: 9

Arg Ala Asn Lys Ser Val Ser Thr Ser Thr Tyr Asn Tyr Leu His
1               5                   10                  15

<210> SEQ ID NO 10
<211> LENGTH: 7
<212> TYPE: PRT
<213> ORGANISM: Murine

<400> SEQUENCE: 10

Leu Ala Ser Asn Leu Ala Ser
1               5

<210> SEQ ID NO 11
<211> LENGTH: 9
<212> TYPE: PRT
<213> ORGANISM: Murine

<400> SEQUENCE: 11

Gln His Ser Arg Asp Leu Pro Pro Thr
1               5

<210> SEQ ID NO 12
<211> LENGTH: 15
<212> TYPE: PRT
<213> ORGANISM: Artificial sequence
<220> FEATURE:
<223> OTHER INFORMATION: optimized light chain CDR1

<400> SEQUENCE: 12

Arg Ala Asp Lys Ser Val Ser Thr Ser Thr Tyr Asn Tyr Leu His
1               5                   10                  15

<210> SEQ ID NO 13
<211> LENGTH: 120
<212> TYPE: PRT
<213> ORGANISM: Artificial sequence
<220> FEATURE:
<223> OTHER INFORMATION: Ab-9 heavy chain variable region

<400> SEQUENCE: 13

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Pro Asn Tyr
            20                  25                  30

Gly Val His Trp Val Arg Gln Pro Pro Gly Lys Ala Leu Glu Trp Leu
        35                  40                  45
```

Ala Val Ile Trp Ser Gly Gly Ser Thr Asn Tyr Ala Ala Phe Val
            50                  55                  60

Ser Arg Leu Arg Ile Ser Lys Asp Thr Ser Lys Ser Gln Val Val Phe
 65                  70                  75                  80

Thr Met Asn Asn Met Asp Pro Val Asp Thr Ala Thr Tyr Tyr Cys Ala
                85                  90                  95

Arg Asn His Asp Asn Pro Tyr Asn Tyr Ala Met Asp Tyr Trp Gly Gln
                100                 105                 110

Gly Thr Thr Val Thr Val Ser Ser
            115                 120

<210> SEQ ID NO 14
<211> LENGTH: 120
<212> TYPE: PRT
<213> ORGANISM: Artificial sequence
<220> FEATURE:
<223> OTHER INFORMATION: Ab-10 heavy chain variable region

<400> SEQUENCE: 14

Gln Val Gln Leu Val Glu Ser Gly Gly Gly Val Val Gln Pro Gly Arg
 1               5                   10                  15

Ser Leu Arg Leu Ser Cys Ala Ala Ser Gly Phe Ser Leu Ser Asn Tyr
                20                  25                  30

Gly Val His Trp Val Arg Gln Ala Pro Gly Lys Gly Leu Glu Trp Leu
            35                  40                  45

Ala Val Ile Trp Ser Gly Gly Ser Thr Asn Tyr Ala Ala Phe Val
            50                  55                  60

Ser Arg Leu Thr Ile Ser Lys Asp Asn Ser Lys Asn Thr Val Tyr Leu
 65                  70                  75                  80

Gln Met Asn Ser Leu Arg Ala Glu Asp Thr Ala Val Tyr Tyr Cys Ala
                85                  90                  95

Arg Asn His Asp Asn Pro Tyr Asn Tyr Ala Met Asp Tyr Trp Gly Gln
                100                 105                 110

Gly Thr Thr Val Thr Val Ser Ser
            115                 120

<210> SEQ ID NO 15
<211> LENGTH: 120
<212> TYPE: PRT
<213> ORGANISM: Artificial sequence
<220> FEATURE:
<223> OTHER INFORMATION: Ab-11 heavy chain variable region

<400> SEQUENCE: 15

Gln Val Gln Leu Val Glu Ser Gly Gly Gly Val Val Gln Pro Gly Arg
 1               5                   10                  15

Ser Leu Arg Leu Ser Cys Ala Ala Ser Gly Phe Thr Leu Pro Asn Tyr
                20                  25                  30

Gly Val His Trp Val Arg Gln Ala Pro Gly Lys Gly Leu Glu Trp Leu
            35                  40                  45

Ala Val Ile Trp Ser Gly Gly Ser Thr Asn Tyr Ala Ala Phe Val
            50                  55                  60

Ser Arg Leu Thr Ile Ser Lys Asp Asn Ser Lys Asn Thr Val Tyr Leu
 65                  70                  75                  80

Gln Met Asn Ser Leu Arg Ala Glu Asp Thr Ala Val Tyr Tyr Cys Ala
                85                  90                  95

Arg Asn His Asp Asn Pro Tyr Asn Tyr Ala Met Asp Tyr Trp Gly Gln

```
              100                 105                 110
Gly Thr Thr Val Thr Val Ser Ser
        115                 120

<210> SEQ ID NO 16
<211> LENGTH: 112
<212> TYPE: PRT
<213> ORGANISM: Artificial sequence
<220> FEATURE:
<223> OTHER INFORMATION: Ab-9 light chain variable region

<400> SEQUENCE: 16

Asp Ile Val Leu Thr Gln Ser Pro Ala Ser Leu Ala Val Ser Pro Gly
1               5                   10                  15

Gln Arg Ala Thr Ile Thr Cys Arg Ala Asn Lys Ser Val Ser Thr Ser
            20                  25                  30

Thr Tyr Asn Tyr Leu His Trp Tyr Gln Gln Lys Pro Gly Gln Pro Pro
        35                  40                  45

Lys Leu Leu Ile Tyr Leu Ala Ser Asn Leu Ala Ser Gly Val Pro Ala
    50                  55                  60

Arg Phe Ser Gly Ser Gly Ser Gly Thr Asp Phe Thr Leu Thr Ile Asn
65                  70                  75                  80

Pro Val Glu Ala Asn Asp Thr Ala Asn Tyr Tyr Cys Gln His Ser Arg
                85                  90                  95

Asp Leu Pro Pro Thr Phe Gly Gln Gly Thr Lys Leu Glu Ile Lys Arg
            100                 105                 110

<210> SEQ ID NO 17
<211> LENGTH: 112
<212> TYPE: PRT
<213> ORGANISM: Artificial sequence
<220> FEATURE:
<223> OTHER INFORMATION: Ab-10 light chain variable region

<400> SEQUENCE: 17

Asp Ile Val Leu Thr Gln Ser Pro Asp Ser Leu Ala Val Ser Leu Gly
1               5                   10                  15

Glu Arg Ala Thr Ile Asn Cys Arg Ala Asp Lys Ser Val Ser Thr Ser
            20                  25                  30

Thr Tyr Asn Tyr Leu His Trp Tyr Gln Gln Lys Pro Gly Gln Pro Pro
        35                  40                  45

Lys Leu Leu Ile Tyr Leu Ala Ser Asn Leu Ala Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Arg
                85                  90                  95

Asp Leu Pro Pro Thr Phe Gly Gln Gly Thr Lys Leu Glu Ile Lys Arg
            100                 105                 110

<210> SEQ ID NO 18
<211> LENGTH: 112
<212> TYPE: PRT
<213> ORGANISM: Artificial sequence
<220> FEATURE:
<223> OTHER INFORMATION: Ab-11 light chain variable region

<400> SEQUENCE: 18

Asp Ile Val Leu Thr Gln Ser Pro Asp Ser Leu Ala Val Ser Leu Gly
1               5                   10                  15
```

```
Glu Arg Ala Thr Ile Asn Cys Arg Ala Asn Lys Ser Val Ser Thr Ser
                20                  25                  30

Thr Tyr Asn Tyr Leu His Trp Tyr Gln Gln Lys Pro Gly Gln Pro Pro
            35                  40                  45

Lys Leu Leu Ile Tyr Leu Ala Ser Asn Leu Ala Ser Gly Val Pro Asp
 50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Arg
                85                  90                  95

Asp Leu Pro Pro Thr Phe Gly Gln Gly Thr Lys Leu Glu Ile Lys Arg
            100                 105                 110

<210> SEQ ID NO 19
<211> LENGTH: 330
<212> TYPE: PRT
<213> ORGANISM: Homo sapiens

<400> SEQUENCE: 19

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
```

```
                    275                 280                 285
Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 20
<211> LENGTH: 326
<212> TYPE: PRT
<213> ORGANISM: Homo sapiens

<400> SEQUENCE: 20

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320
```

Ser Leu Ser Pro Gly Lys
                325

<210> SEQ ID NO 21
<211> LENGTH: 327
<212> TYPE: PRT
<213> ORGANISM: Homo sapiens

<400> SEQUENCE: 21

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 22
<211> LENGTH: 106
<212> TYPE: PRT
<213> ORGANISM: Homo sapiens

<400> SEQUENCE: 22

```
Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105
```

<210> SEQ ID NO 23
<211> LENGTH: 446
<212> TYPE: PRT
<213> ORGANISM: Artificial sequence
<220> FEATURE:
<223> OTHER INFORMATION: Ab-9 heavy chain

<400> SEQUENCE: 23

```
Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Pro Asn Tyr
            20                  25                  30

Gly Val His Trp Val Arg Gln Pro Pro Gly Lys Ala Leu Glu Trp Leu
        35                  40                  45

Ala Val Ile Trp Ser Gly Gly Ser Thr Asn Tyr Ala Ala Phe Val
50                  55                  60

Ser Arg Leu Arg Ile Ser Lys Asp Thr Ser Lys Ser Gln Val Val Phe
65                  70                  75                  80

Thr Met Asn Asn Met Asp Pro Val Asp Thr Ala Thr Tyr Tyr Cys Ala
                85                  90                  95

Arg Asn His Asp Asn Pro Tyr Asn Tyr Ala Met Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
210                 215                 220

Glu Cys Pro Pro Cys Pro Ala Pro Pro Val Ala Gly Pro Ser Val Phe
225                 230                 235                 240
```

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Phe Arg Val Val Ser Val
    290                 295                 300

Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 24
<211> LENGTH: 446
<212> TYPE: PRT
<213> ORGANISM: Artificial sequence
<220> FEATURE:
<223> OTHER INFORMATION: Ab-10 heavy chain

<400> SEQUENCE: 24

Gln Val Gln Leu Val Glu Ser Gly Gly Val Val Gln Pro Gly Arg
1               5                   10                  15

Ser Leu Arg Leu Ser Cys Ala Ala Ser Gly Phe Ser Leu Ser Asn Tyr
            20                  25                  30

Gly Val His Trp Val Arg Gln Ala Pro Gly Lys Gly Leu Glu Trp Leu
        35                  40                  45

Ala Val Ile Trp Ser Gly Gly Ser Thr Asn Tyr Ala Ala Phe Val
    50                  55                  60

Ser Arg Leu Thr Ile Ser Lys Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asn His Asp Asn Pro Tyr Asn Tyr Ala Met Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Phe Arg Val Val Ser Val
290                 295                 300

Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 25
<211> LENGTH: 446
<212> TYPE: PRT
<213> ORGANISM: Artificial sequence
<220> FEATURE:
<223> OTHER INFORMATION: Ab-11 heavy chain

<400> SEQUENCE: 25

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Leu Pro Asn Tyr
            20                  25                  30

Gly Val His Trp Val Arg Gln Ala Pro Gly Lys Gly Leu Glu Trp Leu
        35                  40                  45

Ala Val Ile Trp Ser Gly Gly Ser Thr Asn Tyr Ala Ala Ala Phe Val
    50                  55                  60

Ser Arg Leu Thr Ile Ser Lys Asp Asn Ser Lys Asn Thr Val Tyr Leu
65                  70                  75                  80

```
Gln Met Asn Ser Leu Arg Ala Glu Asp Thr Ala Val Tyr Tyr Cys Ala
                85                  90                  95

Arg Asn His Asp Asn Pro Tyr Asn Tyr Ala Met Asp Tyr Trp Gly Gln
            100                 105                 110

Gly Thr Thr Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
            195                 200                 205

Pro Ser Asn Thr Lys Val Asp Lys Thr Val Glu Arg Lys Cys Cys Val
            210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
            275                 280                 285

Lys Pro Arg Glu Glu Gln Phe Asn Ser Thr Phe Arg Val Val Ser Val
290                 295                 300

Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
            325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 26
<211> LENGTH: 218
<212> TYPE: PRT
<213> ORGANISM: Artificial sequence
<220> FEATURE:
<223> OTHER INFORMATION: Ab-9 light chain

<400> SEQUENCE: 26
```

```
Asp Ile Val Leu Thr Gln Ser Pro Ala Ser Leu Ala Val Ser Pro Gly
 1               5                  10                  15

Gln Arg Ala Thr Ile Thr Cys Arg Ala Asn Lys Ser Val Ser Thr Ser
            20                  25                  30

Thr Tyr Asn Tyr Leu His Trp Tyr Gln Gln Lys Pro Gly Gln Pro Pro
        35                  40                  45

Lys Leu Leu Ile Tyr Leu Ala Ser Asn Leu Ala Ser Gly Val Pro Ala
 50                  55                  60

Arg Phe Ser Gly Ser Gly Ser Gly Thr Asp Phe Thr Leu Thr Ile Asn
 65                  70                  75                  80

Pro Val Glu Ala Asn Asp Thr Ala Asn Tyr Tyr Cys Gln His Ser Arg
            85                  90                  95

Asp Leu Pro Pro Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
            210                 215
```

<210> SEQ ID NO 27
<211> LENGTH: 218
<212> TYPE: PRT
<213> ORGANISM: Artificial sequence
<220> FEATURE:
<223> OTHER INFORMATION: Ab-10 light chain

<400> SEQUENCE: 27

```
Asp Ile Val Leu Thr Gln Ser Pro Asp Ser Leu Ala Val Ser Leu Gly
 1               5                  10                  15

Glu Arg Ala Thr Ile Asn Cys Arg Ala Asp Lys Ser Val Ser Thr Ser
            20                  25                  30

Thr Tyr Asn Tyr Leu His Trp Tyr Gln Gln Lys Pro Gly Gln Pro Pro
        35                  40                  45

Lys Leu Leu Ile Tyr Leu Ala Ser Asn Leu Ala Ser Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln His Ser Arg
            85                  90                  95

Asp Leu Pro Pro Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
    130                 135                 140
```

```
Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 28
<211> LENGTH: 218
<212> TYPE: PRT
<213> ORGANISM: Artificial sequence
<220> FEATURE:
<223> OTHER INFORMATION: Ab-11 light chain

<400> SEQUENCE: 28

Asp Ile Val Leu Thr Gln Ser Pro Asp Ser Leu Ala Val Ser Leu Gly
1               5                   10                  15

Glu Arg Ala Thr Ile Asn Cys Arg Ala Asn Lys Ser Val Ser Thr Ser
                20                  25                  30

Thr Tyr Asn Tyr Leu His Trp Tyr Gln Gln Lys Pro Gly Gln Pro Pro
            35                  40                  45

Lys Leu Leu Ile Tyr Leu Ala Ser Asn Leu Ala Ser Gly Val Pro Asp
        50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Arg
                85                  90                  95

Asp Leu Pro Pro Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```